(12) United States Patent
Esteves et al.

(10) Patent No.: US 10,370,432 B2
(45) Date of Patent: Aug. 6, 2019

(54) HETEROLOGOUS TARGETING PEPTIDE GRAFTED AAVS

(71) Applicant: University of Massachusetts, Boston, MA (US)

(72) Inventors: Miguel Sena Esteves, Westford, MA (US); Sourav Roy Choudhury, Newton, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/516,582

(22) PCT Filed: Oct. 2, 2015

(86) PCT No.: PCT/US2015/053798
§ 371 (c)(1),
(2) Date: Apr. 3, 2017

(87) PCT Pub. No.: WO2016/054554
PCT Pub. Date: Apr. 7, 2016

(65) Prior Publication Data
US 2018/0265571 A1    Sep. 20, 2018

Related U.S. Application Data

(60) Provisional application No. 62/059,738, filed on Oct. 3, 2014.

(51) Int. Cl.
| | |
|---|---|
| *C07K 14/005* | (2006.01) |
| *C07K 14/775* | (2006.01) |
| *C07K 7/00* | (2006.01) |
| *C07K 14/00* | (2006.01) |
| *C12N 15/86* | (2006.01) |
| *A61K 48/00* | (2006.01) |
| *C07K 7/04* | (2006.01) |
| *C07K 14/075* | (2006.01) |
| *C07K 19/00* | (2006.01) |
| *C12N 15/79* | (2006.01) |

(52) U.S. Cl.
CPC ........ *C07K 14/775* (2013.01); *A61K 48/0025* (2013.01); *A61K 48/0058* (2013.01); *C07K 7/00* (2013.01); *C07K 7/04* (2013.01); *C07K 14/00* (2013.01); *C07K 14/005* (2013.01); *C07K 14/075* (2013.01); *C07K 19/00* (2013.01); *C12N 15/79* (2013.01); *C12N 15/86* (2013.01); *C07K 2319/01* (2013.01); *C07K 2319/30* (2013.01); *C07K 2319/33* (2013.01); *C12N 2750/14145* (2013.01); *C12N 2810/85* (2013.01)

(58) Field of Classification Search
CPC ......... C07K 7/00; C07K 14/00; C07K 14/005
See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,177,403 B1 | 1/2001 | Stedman |
| 6,251,677 B1 | 6/2001 | Wilson et al. |
| 6,485,966 B2 | 11/2002 | Gao et al. |
| 6,498,244 B1 | 12/2002 | Patel et al. |
| 6,544,786 B1 | 4/2003 | Xiao et al. |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,217,155 B2 | 12/2015 | Gao et al. |
| 9,249,424 B2 | 2/2016 | Wolf et al. |
| 2001/0016355 A1 | 8/2001 | Samulski et al. |
| 2002/0164783 A1 | 11/2002 | Feldhaus |
| 2003/0103939 A1 | 6/2003 | Engelhardt et al. |
| 2003/0110526 A1 | 6/2003 | Brown et al. |
| 2003/0138772 A1 | 7/2003 | Gao et al. |
| 2004/0101514 A1 | 5/2004 | Liu et al. |
| 2005/0014262 A1 | 1/2005 | Gao et al. |
| 2005/0032219 A1 | 2/2005 | Aubourg et al. |
| 2005/0037988 A1 | 2/2005 | Zamore et al. |
| 2005/0137153 A1 | 6/2005 | McSwiggen et al. |
| 2005/0255086 A1 | 11/2005 | Davidson et al. |

(Continued)

FOREIGN PATENT DOCUMENTS

| | | |
|---|---|---|
| EP | 2261242 A1 | 12/2010 |
| EP | 2468891 A2 | 6/2012 |

(Continued)

OTHER PUBLICATIONS

BLAST Protein Sequence. NCBI; RID-09JSKF33114. Alignment of Seq ID Nos. 87, 179. 2016.
Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.
Adachi et al., Drawing a high-resolution functional map of adeno-associated virus capsid by massively parallel sequencing. Nat Commun. 2014;5:3075. doi: 10.1038/ncomms4075.

(Continued)

*Primary Examiner* — Prema M Mertz
(74) *Attorney, Agent, or Firm* — Wolf, Greenfield & Sacks, P.C.

(57) ABSTRACT

The disclosure in some aspects relates to recombinant adeno-associated viruses having distinct tissue targeting capabilities. In some aspects, the disclosure relates to gene transfer methods using the recombinant adeno-associated viruses. In some aspects, the disclosure relates to isolated AAV capsid proteins and isolated nucleic acids encoding the same.

18 Claims, 28 Drawing Sheets

Specification includes a Sequence Listing.

(56) References Cited

U.S. PATENT DOCUMENTS

| | | |
|---|---|---|
| 2005/0255089 A1 | 11/2005 | Chiorini et al. |
| 2005/0287122 A1 | 12/2005 | Bartlett et al. |
| 2006/0018841 A1 | 1/2006 | Arbetman et al. |
| 2006/0063174 A1 | 3/2006 | Turner et al. |
| 2006/0093589 A1 | 5/2006 | Warrington et al. |
| 2006/0189515 A1 | 8/2006 | Beliveau et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2007/0253936 A1 | 11/2007 | Kay et al. |
| 2008/0292595 A1 | 11/2008 | Arbetman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0197338 A1 | 8/2009 | Vandenberghe et al. |
| 2009/0215879 A1 | 8/2009 | DiPrimio et al. |
| 2009/0239240 A1 | 9/2009 | Chu |
| 2010/0104561 A1 | 4/2010 | Zhong et al. |
| 2010/0186103 A1 | 7/2010 | Gao et al. |
| 2010/0227909 A1 | 9/2010 | Cleary et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0041048 A1 | 2/2012 | Weinberg et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0281516 A1 | 10/2013 | Gao et al. |
| 2013/0323226 A1 | 12/2013 | Wilson et al. |
| 2014/0010861 A1 | 1/2014 | Bancel et al. |
| 2014/0142161 A1 | 5/2014 | Flotte et al. |
| 2014/0142288 A1 | 5/2014 | Davidson et al. |
| 2014/0179770 A1 | 6/2014 | Zhang et al. |
| 2014/0205599 A1 | 7/2014 | Willemsen et al. |
| 2014/0335054 A1 | 11/2014 | Gao et al. |
| 2015/0065560 A1 | 3/2015 | Bjorklund et al. |
| 2015/0258180 A1 | 9/2015 | Mahuran et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar et al. |
| 2017/0029785 A1 | 2/2017 | Zhao et al. |
| 2017/0114340 A1 | 4/2017 | Mueller et al. |
| 2017/0165377 A1 | 6/2017 | Gao et al. |

FOREIGN PATENT DOCUMENTS

| | | |
|---|---|---|
| WO | WO 2003/042397 | 5/2003 |
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2007/000668 A2 | 1/2007 |
| WO | WO 2007/027775 A2 | 3/2007 |
| WO | WO 2008/091703 | 7/2008 |
| WO | WO 2008/125846 A2 | 10/2008 |
| WO | WO 2008/147839 A1 | 12/2008 |
| WO | WO 2008/150897 A2 | 12/2008 |
| WO | WO 2009/043936 | 4/2009 |
| WO | WO 2009/109665 A1 | 9/2009 |
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 11/2014 |
| WO | WO 2015/121501 A1 | 8/2015 |
| WO | WO 2015/164786 A1 | 10/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Bals et al., Transduction of well-differentiated airway epithelium by recombinant adeno-associated virus is limited by vector entry. J Virol. Jul. 1999;73(7):6085-8.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.

Brown et al., A microRNA-regulated lentiviral vector mediates stable correction of hemophilia B mice. Blood. Dec. 15, 2007;110(13):4144-52. Epub Aug. 28, 2007.

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.

Brown et al., Endogenous microRNA regulation suppresses transgene expression in hematopoietic lineages and enables stable gene transfer. Nat Med. May 2006;12(5):585-91. Epub Apr. 23, 2006.

Buning et al., Receptor targeting of adeno-associated virus vectors. Gene Ther. Jul. 2003;10(14):1142-51.

Bussing et al., let-7 microRNAs in development, stem cells and cancer. Trends Mol Med. Sep. 2008;14(9):400-9. doi: 10.1016/j.molmed.2008.07.001. Epub Jul. 31, 2008.

(56) References Cited

OTHER PUBLICATIONS

Calcedo et al., Worldwide epidemiology of neutralizing antibodies to adeno-associated viruses. J Infect Dis. Feb. 1, 2009;199(3):381-90.
Carter et al., Adeno-associated virus gene expression and regulation. CRC Handbook of parvoviruses. 1990:227-54.
Carter, In "Handbook of Parvoviruses", ed., P. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Chen et al., Regulation of immune responses and tolerance: the microRNA perspective. Immunol Rev. May 2013;253(1):112-28. doi:10.1111/imr.12060.
Choudhury et al., Identification of Novel vectors capable of CNS transduction in adult mice after single round selection using DNA shuffled AAV capsid library. Mol Ther. May 1, 2013;21(1):S1.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Cideciyan et al., Human RPE65 gene therapy for Leber congenital amaurosis: persistence of early visual improvements and safety at 1 year. Hum Gene Ther. Sep. 2009;20(9):999-1004.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conlon et al., Ribozyme Approaches towards Down-Regulation of Pi*Z Mutant Human a-1 Anti-Trypsin. Mol. Therapy. 2004;9:S333. Abstract 875.
Conrad et al., Safety of single-dose administration of an adeno-associated virus (AAV)-CFTR vector in the primate lung. Gene Ther. Aug. 1996;3(8):658-68.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Csak et al., microRNA-122 regulates hypoxia-inducible factor-1 and vimentin in hepatocytes and correlates with fibrosis in diet-induced steatohepatitis. Liver Int. Feb. 2015;35(2):532-41. doi: 10.1111/liv.12633. Epub Jul. 28, 2014.
Czech, MicroRNAs as therapeutic targets. N Engl J Med. Mar. 16, 2006;354(11):1194-5.

Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Ebert et al., MicroRNA sponges: competitive inhibitors of small RNAs in mammalian cells. Nat Methods. Sep. 2007;4(9):721-6. Epub Aug. 12, 2007.
Ehlert et al., Cellular toxicity following application of adeno-associated viral vector-mediated RNA interference in the nervous system. BMC Neurosci. Feb. 18, 2010;11:20.
Elmen et al., LNA-mediated microRNA silencing in non-human primates. Nature. Apr. 2008;452(17): 896-900.
Elmen et al.,Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fischer et al., Successful transgene expression with serial doses of aerosolized rAAV2 vectors in rhesus macaques. Mol Ther. Dec. 2003;8(6) 918-26.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Fu et al., Self-complementary adeno-associated virus serotype 2 vector: global distribution and broad dispersion of AAV-mediated transgene expression in mouse brain. Mol Ther. Dec. 2003;8(6):911-7.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.

(56) References Cited

OTHER PUBLICATIONS

Gao et al., Adeno-associated viruses undergo substantial evolution in primates during natural infections. Proc Natl Acad Sci U S A. May 13, 2003;100(10):6081-6. Epub Apr. 25, 2003.

Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.

Gao et al., Biology of AAV serotype vectors in liver-directed gene transfer to nonhuman primates. Mol Ther. Jan. 2006;13(1):77-87. Epub Oct. 10, 2005.

Gao et al., Erythropoietin gene therapy leads to autoimmune anemia in macaques. Blood. May 1, 2004;103(9):3300-2. Epub Dec. 24, 2003.

Gao et al., Inadvertent gene transfer of co-packaged rep and cap sequences during the production of AAV vector and its potential impact on vector performance. Molecular Therapy. May 2008;16(Suppl. 1):S105-S106. Abstract 279.

Gao et al., New recombinant serotypes of AAV vectors. Curr Gene Ther. Jun. 2005;5(3):285-97.

Gao et al., Novel adeno-associated viruses from rhesus monkeys as vectors for human gene therapy. Proc Natl Acad Sci USA. Sep. 3, 2002;99(18):11854-9. Epub Aug. 21, 2002.

Gao et al., RAAV-mediated targeting in adult mice and its potential in generating animal models of tissue-specific somatic transgenics or knock down. Molecular Therapy. May 2008;16(1):S118-S119. Abstract 316.

Genbank Submission; Accession No. ADZ26851; Wilson et al.; Jun. 30, 2005.

Genbank Submission; Accession No. AF028705.1; Rutledge et al.; Jan. 12, 1998.

Genbank Submission; NCBI, Accession No. AAB95450; Rutledge et al.; Jan. 12, 1998.

Genbank Submission; NCBI, Accession No. AAS99264; Gao et al.; Jun. 24, 2004.

Genbank Submission; NCBI, Accession No. ABA71701; Schmidt et al.; May 10, 2006.

Genbank Submission; NCBI, Accession No. ACB55301; Vandenberghe et al.; Jul. 31, 2008.

Genbank Submission; NCBI, Accession No. ACB55310; Vandenberghe et al.; Jul. 31, 2008.

Genbank Submission; NCBI, Accession No. NP_049542; Xiao et al.; Mar. 11, 2010.

Genbank Submission; NCBI, Accession No. YP_680426; Ruffing et al.; Nov. 19, 2010.

Gentner et al., Stable knockdown of microRNA in vivo by lentiviral vectors. Nat Methods. Jan. 2009;6(1):63-6. doi: 10.1038/nmeth.1277. Epub Nov. 30, 2008.

Girard et al., miR-122, a paradigm for the role of microRNAs in the liver. J Hepatol. Apr. 2008;48(4):648-56. doi: 10.1016/j.jhep.2008.01.019. Epub Feb. 12, 2008.

Gramantieri et al., Cyclin G1 is a target of miR-122a, a microRNA frequently down-regulated in human hepatocellular carcinoma. Cancer Res. Jul. 1, 2007;67(13):6092-9.

Grimm et al., Fatality in mice due to oversaturation of cellular microRNA/short hairpin RNA pathways. Nature. May 25, 2006;441(7092):537-41.

Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.

Haussecker et al., miR-122 continues to blaze the trail for microRNA therapeutics. Mol Ther. Feb. 2010;18(2):240-2. doi: 10.1038/mt.2009.313.

Hernandez et al., Latent adeno-associated virus infection elicits humoral but not cell-mediated immune responses in a nonhuman primate model. J Virol. Oct. 1999;73(10):8549-58.

Hildinger et al., Hybrid vectors based on adeno-associated virus serotypes 2 and 5 for muscle-directed gene transfer. J Virol. Jul. 2001;75(13):6199-203.

Hsu et al., Essential metabolic, anti-inflammatory, and anti-tumorigenic functions of miR-122 in liver. J Clin Invest. Aug. 2012;122(8):2871-83. doi:10.1172/JCI63539. Epub Jul. 23, 2012.

Hutvágner et al., Sequence-specific inhibition of small RNA function. PLoS Biol. Apr. 2004;2(4):E98. Epub Feb. 24, 2004.

Iida et al., Systemic Delivery of Tyrosine-Mutant AAV Vectors Results in Robust Transduction of Neurons in Adult Mice. BioMed Res Int. 2013;2013.

Jakobsson et al., Lentiviral vectors for use in the central nervous system. Mol Ther. Mar. 2006;13(3):484-93. Epub Jan. 3, 2006.

Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.

Johnson et al., RAS is regulated by the let-7 microRNA family. Cell. Mar. 11, 2005;120(5):635-47.

Kaspar et al., Retrograde viral delivery of IGF-1 prolongs survival in a mouse ALS model. Science. Aug. 8, 2003;301(5634):839-42.

Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.

Kota et al., Therapeutic microRNA delivery suppresses tumorigenesis in a murine liver cancer model. Cell. Jun. 12, 2009;137(6):1005-17. doi: 10.1016/j.cell.2009.04.021.

Kotin et al., Organization of adeno-associated virus DNA in latently infected Detroit 6 cells. Virology. Jun. 1989;170(2):460-7.

Kotin et al., Site-specific integration by adeno-associated virus. Proc Natl Acad Sci U S A. Mar. 1990;87(6):2211-5.

Krutzfeldt et al., Silencing of microRNAs in vivo with 'antagomirs'. Nature. Dec. 1, 2005;438(7068):685-9. Epub Oct. 30, 2005.

Kutay et al., Downregulation of miR-122 in the rodent and human hepatocellular carcinomas. J Cell Biochem. Oct. 15, 2006;99(3):671-8.

Lanford et al., Therapeutic silencing of microRNA-122 in primates with chronic hepatitis C virus infection. Science. Jan. 8, 2010;327(5962):198-201. Epub Dec. 3, 2009.

Lawlor et al., Efficient gene delivery and selective transduction of glial cells in the mammalian brain by AAV serotypes isolated from nonhuman primates. Mol Ther. Oct. 2009;17(10):1692-702. doi:10.1038/mt.2009.170.

Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].

Lewis et al., Conserved seed pairing, often flanked by adenosines, indicates that thousands of human genes are microRNA targets. Cell. Jan. 14, 2005;120(1):15-20.

Lewis et al., Prediction of mammalian microRNA targets. Cell. Dec. 26, 2003;115(7):787-98.

Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.

Li et al., Ex vivo transduction and transplantation of bone marrow cells for liver gene delivery of alpha1-antitrypsin. Mol Ther. Aug. 2010;18(8):1553-8. Epub Jun. 15, 2010.

Li et al., Intronic microRNA: discovery and biological implications. DNA Cell Biol. Apr. 2007;26(4):195-207.

Li et al., Protein trans-splicing as a means for viral vector-mediated in vivo gene therapy. Hum Gene Ther. Sep. 2008;19(9):958-64. doi: 10.1089/hum.2008.009.

Lin et al., Impact of preexisting vector immunity on the efficacy of adeno-associated virus-based HIV-1 Gag vaccines. Hum Gene Ther. Jul. 2008;19(7):663-9.

Lowenstein, Crossing the rubicon. Nat Biotechnol. Jan. 2009;27(1):42-4.

Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.

Lux et al., Green fluorescent protein-tagged adeno-associated virus particles allow the study of cytosolic and nuclear trafficking. J Virol. Sep. 2005;79(18):11776-87.

(56) References Cited

OTHER PUBLICATIONS

Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Maguire et al., Directed evolution of adeno-associated virus for glioma cell transduction. J Neurooncol. Feb. 2010;96(3):337-47. doi:10.1007/s11060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Mandel et al., Recombinant adeno-associated viral vectors as therapeutic agents to treat neurological disorders. Mol Ther. Mar. 2006;13(3):463-83. Epub Jan. 18, 2006.
Manfredsson et al., AAV9: a potential blood-brain barrier buster. Mol Ther. Mar. 2009;17(3):403-5.
Matalon et al., Adeno-associated virus-mediated aspartoacylase gene transfer to the brain of knockout mouse for canavan disease. Mol Ther. May 2003;7(5 Pt 1):580-7.
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McLean et al., Gene targeted therapeutics for liver disease in alpha-1 antitrypsin deficiency. Biologics. 2009;3:63-75. Epub Jul. 13, 2009.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Meister et al., Sequence-specific inhibition of microRNA- and siRNA-induced RNA silencing. RNA. Mar. 2004;10(3):544-50.
Moffett et al., N-Acetylaspartate in the CNS: from neurodiagnostics to neurobiology. Prog Neurobiol. Feb. 2007;81(2):89-131. Epub Jan. 5, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., In Vivo AAV Delivered Allele Specific shRNA for the Knockdown of Alpha-1 Antitrypsin. Molecular Therapy May 2010;18(1):S22. Abstract 53.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.

O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:574. Abstract 229.
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Seiler et al., Adeno-associated virus types 5 and 6 use distinct receptors for cell entry. Hum Gene Ther. Jan. 2006;17(1):10-9.
Sen et al., Micromanaging vascular biology: tiny microRNAs play big band. J Vasc Res. 2009;46(6):527-40. doi: 10.1159/000226221. Epub Jun. 30, 2009.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 30, 2006;2:4.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Tenenbaum et al., Recombinant AAV-mediated gene delivery to the central nervous system. J Gene Med. Feb. 2004;6 Suppl 1:S212-22.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
UNIPROT Submission; Accession No. A8IGP7; Nov. 13, 2013.
UNIPROT Submission; Accession No. H3GK32; Feb. 6, 2013.
UNIPROT Submission; Accession No. T2BRA8; Nov. 13, 2013.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.

(56) References Cited

OTHER PUBLICATIONS

Vaucheret et al., the action of ARGONAUTE1 in the miRNA pathway and its regulation by the miRNA pathway are crucial for plant development. Genes Dev. May 15, 2004;18(10):1187-97. Epub May 6, 2004.
Vermeulen et al., Double-stranded regions are essential design components of potent inhibitors of RISC function. RNA. May 2007;13(5):723-30. Epub Mar. 30, 2007.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Watson et al., Intrathecal administration of AAV vectors for the treatment of lysosomal storage in the brains of MPS I mice. Gene Ther. Jun. 2006;13(11):917-25.
Wein et al., Efficient bypass of mutations in dysferlin deficient patient cells by antisense-induced exon skipping. Hum Mutat. Feb. 2010;31(2):136-42. doi: 10.1002/humu.21160.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.
Wu et al., Alpha2,3 and alpha2,6 N-linked sialic acids facilitate efficient binding and transduction by adeno-associated virus types 1 and 6. J Virol. Sep. 2006;80(18):9093-103.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., MicroRNA regulated tissue specific transduction by rAAV vector. Molecular Therapy. May 2009;17(1): S279. Abstract 732.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.
Yan et al., Unique biologic properties of recombinant AAV1 transduction in polarized human airway epithelia. J Biol Chem. Oct. 6, 2006;281(40):29684-92. Epub Aug. 9, 2006.
Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.
Yu et al., let-7 regulates self renewal and tumorigenicity of breast cancer cells. Cell. Dec. 14, 2007;131(6):1109-23.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.
Zhong et al., Chimpanzee-derived novel natural variants of aav9: vector development and interrogation of correlations between capsid structure and vector biology. Molecular Therapy. May 2010;18(1): S24. Abstract 58.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Zolotukhin et al., Production and purification of serotype 1, 2, and 5 recombinant adeno-associated viral vectors. Methods. Oct. 2002;28(2):158-67.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.
Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.
Suckau et al., 851. The Effect of Genome Size and Design of scAAV Vectors on Efficiency of shRNA Expression and Gene Knockdown. May 1, 2007;15(1):S325.
Xie et al., DNA Sequences Encoding shRNAs Can Replace Mutant ITR in scAAV Genome for Efficient Replication and Packaging and Transcribe shRNAs by pol III Promoter Activity of wt ITR for Efficient Gene Silencing. Mol Therapy. May 2015;23(1):S269. Abstract 676.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

HETEROLOGOUS TARGETING PEPTIDE GRAFTED AAVS

RELATED APPLICATIONS

This application is a National Stage Application of PCT/US2015/053798, filed Oct. 2, 2015, entitled "HETEROLOGOUS TARGETING PEPTIDE GRAFTED AAVS", which claims the benefit under 35 U.S.C. § 119(e) of U.S. Provisional Application Ser. No. 62/059,738, entitled, "HETEROLOGOUS TARGETING PEPTIDE GRAFTED AAVS", filed on Oct. 3, 2014, the entire content of each application which is incorporated herein by reference.

FEDERALLY SPONSORED RESEARCH

This invention was made with government support under grant no. R01 NS066310 awarded by the National Institutes of Health. The government has certain rights in the invention.

FIELD

In some aspects, the disclosure provides novel AAVs and methods of use thereof as well as related kits.

BACKGROUND

Adeno-associated virus (AAV) is a small (~26 nm) replication-defective, nonenveloped virus, that depends on the presence of a second virus, such as adenovirus or herpes virus, for its growth in cells. AAV was discovered in 1960s as a contaminant in adenovirus (a cold causing virus) preparations. Its growth in cells is dependent on the presence of adenovirus and, therefore, it was named as adeno-associated virus. AAV can infect both dividing and non-dividing cells and may incorporate its genome into that of the host cell. These features make AAV a very attractive candidate for creating viral vectors for gene therapy.

SUMMARY

Aspects of the disclosure relate to recombinant AAVs (rAAVs) engineered to contain heterologous targeting peptides that target the rAAVs to certain cells and/or tissues. RAAVs disclosed herein are useful because they can effectively deliver nucleic acids of interest to a particular cell and/or tissue, e.g., for purposes of manipulating levels of a particular gene product in the cell and/or tissue. For example, in some embodiments, the disclosure provides rAAVs comprising a capsid protein having a heterologous targeting peptide that confers unique tissue targeting and cell transduction properties. In some embodiments, heterologous targeting peptides are provided that are represented by the formula $[A]_n$, wherein A is alanine and n is an integer in a range of 5 to 31. In some embodiments, such heterologous targeting peptides are useful for targeting AAVs to tissues of the central nervous system (CNS). In some embodiments, heterologous targeting peptides are provided that are in a range of 11 to 31 amino acids in length. In some embodiments, heterologous targeting peptides are provided that are in a range of 11 to 27 amino acids in length. In some embodiments, heterologous targeting peptides are provided that are in a range of 17 to 21 amino acids in length. In some embodiments, heterologous targeting peptides are provided that are 19 amino acids in length. In some embodiments, a heterologous targeting peptide is a polypeptide represented by SEQ ID NO: 5. In some embodiments, a heterologous targeting peptide is represented by SEQ ID NO: 7. In some embodiments, a heterologous targeting peptide is a polypeptide encoded by the nucleic acid sequence represented by SEQ ID NO: 29.

In some embodiments, a heterologous targeting peptide further comprises an N-terminal tag. In some embodiments, the N-terminal tag is a peptide tag. In some embodiments, the N-terminal tag is a Myc tag. In some embodiments, the N-terminal tag is a poly-histidine tag (His) tag. In some embodiments, the tag comprises consecutive histidines in the range about 2 amino acids to about 10 amino acids, about 6 amino acids to about 10 amino acids, about 6 amino acids to about 20 amino acids, or about 6 amino acids to about 30 amino acids in length. In some embodiments, the His tag comprises or consists of six amino acids in length. In some embodiments, the His tag is has six amino acids and is referred to as a hex-His tag.

In some embodiments, a capsid protein having a heterologous targeting peptide is a VP1 capsid protein. In some embodiments, a capsid protein having a heterologous targeting peptide is a VP2 capsid protein. In some embodiments, a capsid protein having a heterologous targeting peptide is a VP3 capsid protein. In some embodiments, an rAAV comprises a VP1 and/or VP2 and/or VP3 capsid protein comprising a heterologous targeting peptide. In some embodiment, the heterologous targeting peptide is N-terminally grafted in or to the capsid protein. In some embodiments, a AAV capsid protein further comprises a linker conjugated to the C-terminus of the heterologous targeting peptide. In some embodiments, the linker comprises a stretch of two or more glycine residues. In some embodiments, the polypeptide repeat is GGGGS (SEQ ID NO: 28).

In some embodiments, the heterologous targeting peptide targets the CNS, optionally the brain. In some aspects, the disclosure relates to an rAAV comprising an AAV capsid protein having a heterologous targeting peptide (e.g., which is N-terminally grafted in or to the capsid protein) that mediates transcytosis across the blood-brain barrier. In some embodiments, the heterologous targeting peptide is a lipoprotein receptor-related protein (LRP) ligand.

In some embodiments, the disclosure relates to an AAV capsid protein having a heterologous targeting peptide, in which the AAV capsid protein is not of an AAV2 serotype. In some embodiments, an AAV capsid protein having a heterologous targeting peptide is a VP2 capsid protein. In some embodiments, an AAV capsid protein having a heterologous targeting peptide is of a serotype derived from a non-human primate. In some embodiments, the AAV capsid protein having a heterologous targeting peptide is of a AAVrh8 serotype. In some embodiments, an AAV capsid protein having a heterologous targeting peptide is of an AAV9, optionally AAV9.47, serotype.

In some embodiments, an N-terminally grafted heterologous targeting peptide is inserted before the first, second, third, fourth, fifth, sixth, seventh, eighth, ninth, or tenth amino acid of the capsid protein. In some embodiments, an N-terminally grafted heterologous targeting peptide is inserted between the first and second N-terminal amino acids of the capsid protein. In some embodiments, the first N-terminal amino acid of the capsid protein (e.g., a VP1, VP2 or V3 capsid protein) is a methionine. Accordingly, in some embodiments, an N-terminally grafted heterologous targeting peptide may be inserted after (e.g., immediately after) an N-terminal methionine residue of a capsid protein. In some embodiments, the first N-terminal amino acid of the capsid protein (e.g., a VP2 capsid protein) is an amino acid encoded by a non-canonical start codon, such as a threonine. Accordingly, in some embodiments, an N-terminally grafted heterologous targeting peptide may be inserted after (e.g., immediately after) an N-terminal threonine residue of a capsid protein.

In some embodiments, the disclosure relates to a rAAV comprising a capsid protein having an N-terminally grafted heterologous targeting peptide, in which the N-terminally grafted heterologous targeting peptide is present only in the VP2 capsid protein. In some embodiments, the disclosure relates to a composition comprising a rAAV comprising a capsid protein having an N-terminally grafted heterologous targeting peptide, in which the N-terminally grafted heterologous targeting peptide is present only in the VP2 capsid protein. In some embodiments, the composition further comprises a pharmaceutically acceptable carrier. In some embodiments, an rAAV comprises a capsid protein having an amino acid sequence selected from the group consisting of: SEQ ID NOs: 19-27.

In some embodiments, the disclosure relates to a host cell containing a nucleic acid that comprises a coding sequence selected from the group consisting of: SEQ ID NOs: 8-18 that is operably linked to a promoter. In some embodiments, the disclosure relates to a composition comprising the host cell described above. In some embodiments, the composition comprising the host cell above further comprises a cryopreservative.

The disclosure also relates to methods of delivering a transgene to a subject using the rAAVs described herein. In some embodiments, the disclosure relates to a method for delivering a transgene to a subject comprising administering a rAAV to a subject, wherein the rAAV comprises: (i) a capsid protein having a sequence selected from SEQ ID NOs: 19-27, and (ii) at least one transgene, and in which the rAAV infects cells of a target tissue of the subject. In some embodiments, the at least one transgene encodes a protein (e.g., a therapeutic protein). In some embodiments, the protein is an immunoglobulin heavy chain or light chain or fragment thereof. In some embodiments, the at least one transgene expresses a molecule that is involved in genome editing (e.g., a component of a CRISPR-based genome editing system (e.g., a Cas9 or similar enzyme)).

In some embodiments, the at least one transgene encodes a small interfering nucleic acid. In some embodiments, the small interfering nucleic acid is a miRNA. In some embodiments, the small interfering nucleic acid is a miRNA sponge or TuD RNA that inhibits the activity of at least one miRNA in the subject or animal. In some embodiments, the miRNA is expressed in a cell of the target tissue. In some embodiments, the target tissue is skeletal muscle, heart, liver, pancreas, brain or lung. In some embodiments, the transgene expresses a transcript that comprises at least one binding site for a miRNA, wherein the miRNA inhibits activity of the transgene, in a tissue other than the target tissue, by hybridizing to the binding site.

In some embodiments, the transgene comprises a tissue specific promoter or inducible promoter. In some embodiments, the tissue specific promoter is a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter.

In some embodiments, an rAAV disclosed herein is administered to a subject intravenously, intravascularly, transdermally, intraocularly, intrathecally, orally, intramuscularly, subcutaneously, intranasally, or by inhalation. In some embodiments, a subject is selected from a mouse, a rat, a rabbit, a dog, a cat, a sheep, a pig, and a non-human primate. In some embodiments, a subject is a human.

Also provided herein are isolated nucleic acids. In some embodiments, the disclosure relates to an isolated nucleic acid comprising a sequence selected from the group consisting of: SEQ ID NOs: 8-18. In some embodiments, the disclosure relates to an isolated nucleic acid encoding an AAV capsid protein having an amino acid sequence selected from the group consisting of: SEQ ID NOs: 19-27. In some embodiments, the disclosure relates to an isolated AAV capsid protein comprising an amino acid sequence selected from the group consisting of: SEQ ID NOs: 19-27.

In some embodiments, the disclosure relates to a composition comprising the isolated AAV capsid proteins described herein. In some embodiments, the composition further comprises a pharmaceutically acceptable carrier.

In some embodiments, the disclosure relates to a kit for producing a rAAV. In some embodiments, the kit comprises a container housing an isolated nucleic acid having a sequence of any one of SEQ ID NOs: 8-18. In some embodiments, the kit further comprises instructions for producing the rAAV. In some embodiments, the kit further comprises at least one container housing a recombinant AAV vector, wherein the recombinant AAV vector comprises a transgene.

In some embodiments, the disclosure relates to a kit comprising a container housing a recombinant AAV having an isolated AAV capsid protein having an amino acid sequence as set forth in any of SEQ ID NOs: 19-27.

Each of the features of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 8A shows an overview of GFP distribution in brain and spinal cord in AAV-AS and AAV9 injected mice ($5 \times 10^{11}$ vg/mouse). Representative images of coronal brain sections located in relation to bregma at +0.5 mm, −0.5 mm and −1.80 mm, and cervical spinal cord (left to right) are shown. FIG. 8B shows transduction of neuronal populations in different brain regions. Black arrows indicate examples of GFP-positive neurons identified by morphology. Bar=50 µm. FIG. 8C shows the phenotype of transduced cells was identified by double immunofluorescence staining with antibodies to GFP, pan-neuronal marker NeuN or striatal medium spiny neuron marker DARPP32. Neuronal transduction in spinal cord was examined in sections stained for GFP and NeuN. The large size and morphology of GFP-positive neurons in the ventral spinal cord suggest a motor neuron identity. White arrows indicate examples of GFP-positive neurons. Bar=10 µm.

FIG. 9A shows Western blot analysis of capsid protein composition of AAV vectors ($1 \times 10^{10}$ vg/lane) showed the presence of VP1, VP2 and VP3 capsid proteins. The poly-alanine VP2 fusion protein of AAV-AS capsid (indicated by black arrow) has a higher molecular weight than VP2 protein. FIG. 9B shows quantification of percentage of GFP-positive neurons in striatum and thalamus of mice injected with AAV-AS-GFP or AAV9-GFP vectors. Data shown is mean±SD (n=4 biological replicates per group). FIG. 9C shows AAV vector genome content in cerebrum and spinal cords (n=4 animals per group). Age matched non-injected mice were included as controls (not shown). FIG. 9D shows Western blot analysis of GFP expression in cerebrum and spinal cord of 2 animals per group. Signal intensity of GFP was normalized to corresponding β-actin signal intensity for quantitative comparison. FIG. 9E shows AAV vector genome content in liver and skeletal muscle (quadriceps) (n=4 animals per group). Data shown is mean±SD. FIG. 9F shows Western blot analysis of GFP protein expression in liver and skeletal muscle (quadriceps). *$p<0.05$, $p<0.01$, *$p<0.001$, ****$p<0.0001$ by Student's unpaired t-test.

FIG. 10A shows transduction of neurons in the cat brain after systemic delivery of AAV-AS vector ($1.29 \times 10^{13}$ vg). Representative images (left) show GFP-positive cells with neuronal morphology in various structures in the brain and spinal cord. Bar=50 µm. FIG. 10B shows double immunofluorescence staining for GFP and NeuN (right) confirm the neuronal identity of GFP-positive cells in brain and spinal cord. White arrows indicate examples of GFP-positive neurons. Bar=50 µm.

FIG. 11A shows changes in Hu mRNA levels in brain structures, cervical spinal cord and liver in wild type mice injected systemically with AAV-AS or AAV9 vectors (n=4 per group) ($9.4 \times 10^{11}$ vg/mouse) encoding a U6 promoter-driven artificial microRNA (mile) targeting mouse huntingtin mRNA. Values for each region were normalized to Flu mRNA levels in age-matched PBS-injected mice. *$p<0.05$, $p<0.01$, *$p<0.001$, ****$p<0.0001$ by Student's unpaired t-test. Data shown is mean±error. FIG. 11B shows Western blot analysis of Htt and GFP protein levels in brain structures, cervical spinal cord and liver of the same AAV-injected mice and PBS-injected controls. *$p<0.05$, $p<0.01$, *$p<0.001$, ****$p<0.0001$ by Student's unpaired t-test. Data shown is mean±SD.

FIG. 12A shows AAV vector genome content in cerebrum, spinal cord, liver, and muscle of mice intravenously injected with AAV9.47-GFP or AAV9-GFP vectors ($5 \times 10^{11}$ vg/mouse)(n=4 animals per group). FIG. 12B shows quantification of GFP-positive neurons per high power field in striatum and thalamus of injected mice (n=4 biological replicates per group). Data shown as mean±SD. **$p<0.01$ by Student's unpaired t-test.

FIG. 13A shows a schematic diagram of VP2 capsid protein showing insertion site of peptide and $G_4S$ linker. FIG. 13B shows an illustration of packaging strategy. VP1 and VP3 are expressed separately (top) from VP2 fused with peptide (below).

FIG. 16A shows Western blot analysis of AAVrh8 and AAVrh8-AS vectors ($1 \times 10^{10}$ vg total) for the presence of capsid proteins VP1, 2 and 3. Arrow indicates the position of the AS-VP2 fusion protein on the blot. FIGS. 16B and 16C show transduced cell distribution in brain. Sections represented in FIG. 16B correspond to coronal planes +0.5 mm and −1.80 mm from the bregma plane. Bar=50 µm.

DETAILED DESCRIPTION

Figure 1A:
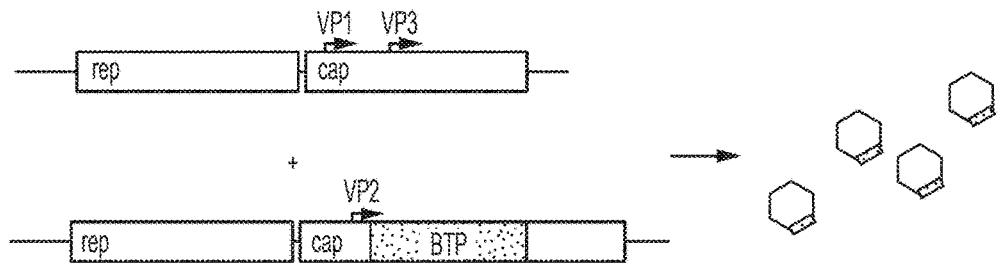
FIG. 1A depicts a graphical representation of the AAV packaging strategy used in this example. VP1 and VP3 were expressed from one plasmid, while VP2 containing an N-terminal Angiopep-2 (referred to here as BTP) insertion was expressed from a separate plasmid.

In some embodiments, recombinant AAVs (rAAVs) are provided herein that have distinct tissue targeting properties that make them useful for certain gene therapy and research applications. AAV capsid proteins are provided herein that comprise heterologous targeting peptides that confer desired cell and/or tissue targeting properties on rAAVs comprising such capsid proteins. For examples, in some aspects, a heterologous targeting peptide is grafted in or to a capsid protein of an rAAV that facilitates transport of the rAAV across the blood brain barrier (BBB). Accordingly, in some aspects, rAAV-based methods for delivering a transgene to a target tissue in a subject are provided. The transgene delivery methods may be used for gene therapy (e.g., to treat disease) or research (e.g., to create a somatic transgenic animal model) applications.

Isolated AAV Capsid Proteins and Nucleic Acids Encoding the Same

AAVs that infect mammals, particularly non-human primates, are useful for creating gene transfer vectors for clinical development and human gene therapy applications. The disclosure provides in some aspects novel AAV capsid proteins developed through functional mutagenesis. In some embodiments, an AAV capsid is provided that has an amino acid sequence selected from the group consisting of SEQ ID NO:19-27. In some embodiments, an AAV capsid is provided that is encoded by a nucleic acid sequence selected from the group consisting of SEQ ID NO: 8-18.

An example of an isolated nucleic acid that encodes an AAV capsid protein is a nucleic acid having a sequence selected from the group consisting of: SEQ ID NO: 8-18 as well as nucleic acids having substantial homology thereto. In some embodiments, isolated nucleic acids that encode AAV capsids are provided that have sequences selected from: SEQ ID NO:8-18.

In some embodiments, nucleic acids are provided that encode an AAV capsid having a peptide grafted within its capsid sequence (e.g., a AAV9 capsid) and up to 5, up to 10, up to 20, up to 30, up to 40, up to 50, up to 100 other amino acid alternations.

In some embodiments, a fragment (portion) of an isolated nucleic acid encoding a AAV capsid sequence may be useful for constructing a nucleic acid encoding a desired capsid sequence. Fragments may be of any appropriate length (e.g., at least 9, at least 18, at least 36, at least 72, at least 144, at least 288, at least 576, at least 1152 or more nucleotides in length). For example, a fragment of nucleic acid sequence encoding a variant amino acid (compared with a known AAV serotype) may be used to construct, or may be incorporated within, a nucleic acid sequence encoding an AAV capsid sequence to alter the properties of the AAV capsid. For example, a nucleic sequence encoding an AAV variant may comprise n amino acid variants (e.g., in which n=1, 2, 3, 4, 5, 6, 7, 8, 9, 10 or more) compared with a known AAV serotype (e.g., AAV9). A recombinant cap sequence may be constructed having one or more of the n amino acid variants by incorporating fragments of a nucleic acid sequence comprising a region encoding a variant amino acid into the sequence of a nucleic acid encoding the known AAV serotype. The fragments may be incorporated by any appropriate method, including using site directed mutagenesis. In some embodiments, polypeptide fragments that are not normally present in AAV capsid proteins may be incorporated into a recombinant cap sequence. In some embodiments, the polypeptide fragment is grafted onto the recombinant cap sequence. Thus, new AAV variants may be created having new properties.

As used herein, "grafting" refers to joining or uniting of one molecule with another molecule. In some embodiments, the term grafting refers to joining or uniting of at least two molecules such that one of the at least two molecules is inserted within another of the at least two molecules. In some embodiments, the term grafting refers to joining or uniting of at least two polymeric molecules such that one of the at least two molecules is appended to another of the at least two molecules. In some embodiments, the term grafting refers to joining or uniting of one polymeric molecule (e.g., a nucleic acid, a polypeptide) with another polymeric molecule (e.g., a nucleic acid, a polypeptide). In some embodiments, the term grafting refers to joining or uniting of at least two nucleic acid molecules such that one of the at least two nucleic acid molecules is inserted within another of the at least two nucleic acid molecules. In some embodiments, the term grafting refers to joining or uniting of at least two nucleic acid molecules such that one of the at least two molecules is appended to another of the at least two nucleic acid molecules.

In some embodiments, a nucleic acid formed through grafting (a grafted nucleic acid) encodes a chimeric protein. In some embodiments, a grafted nucleic acid encodes a chimeric protein, such that one polypeptide is effectively inserted into another polypeptide (e.g., not directly conjugated before the N-terminus or after the C-terminus), thereby creating a contiguous fusion of two polypeptides. In some embodiments, a grafted nucleic acid encodes a chimeric protein, such that one polypeptide is effectively appended to another polypeptide (e.g., directly conjugated before the N-terminus or after the C-terminus), thereby creating a contiguous fusion of two polypeptides. In some embodiments, the term grafting refers to joining or uniting of at least two polypeptides, or fragments thereof, such that one of the at least two polypeptides or fragments thereof is inserted within another of the at least two polypeptides or fragments thereof. In some embodiments, the term grafting refers to joining or uniting of at least two polypeptides or fragments thereof such that one of the at least two polypeptides or fragments thereof is appended to another of the at least two polypeptides or fragments thereof.

In some embodiments, the disclosure relates to an adeno-associated virus (AAV) capsid protein comprising a AAV capsid protein having an N-terminally grafted heterologous targeting peptide in a range of 11 to 31 amino acids in length. In some embodiments, the disclosure relates to an adeno-associated virus (AAV) capsid protein comprising a AAV capsid protein having an N-terminally grafted heterologous targeting peptide in a range of 11 to 27 amino acids in length. In some embodiments, the heterologous targeting peptide is in a range of 17 to 21 amino acids in length. In some embodiments, the heterologous targeting peptide is 19 amino acids in length. In some embodiments, the heterologous targeting peptide is a polypeptide represented by SEQ ID NO: 5. In some embodiments, the heterologous targeting peptide is represented by SEQ ID NO: 7. In some embodiments, the heterologous targeting peptide is a polypeptide encoded by the nucleic acid sequence represented by SEQ ID NO: 29.

In some embodiments, a heterologous targeting protein further comprises an N-terminal tag, for example a polypeptide tag. As used herein, "N-terminal tag" refers to a peptide sequence that is covalently linked (e.g., grafted) onto the N-terminus of a recombinant protein. An N-terminal tag can be directly linked to a recombinant protein (e.g., contiguously linked) or indirectly linked to a recombinant protein (e.g., via a linker sequence). Peptide tags may include, for example, Myc tag, His tag, FLAG tag, chitin binding protein (CBP) tag, maltose binding protein tag (MBP), and human influenza hemagglutinin (HA) tag, and glutathione-S-transferase (GST) tag. Additional descriptions of protein tags can be found, for example, in Lichty et al., Protein Expr. Purif., 41(1): 98-105 (2005) the pertinent contents of which are incorporated herein by reference.

In some embodiments, a heterologous targeting peptide comprises an N-terminal Myc tag. In some embodiments, a heterologous targeting peptide comprises an N-terminal poly-histidine tag (His) tag. In some embodiments, the His tag ranges from about 6 amino acids to about 10 amino acids in length. In some embodiments, the His tag is six amino acids in length and is referred to as a hex-His tag. Without wishing to be bound by any particular theory, the presence of an N-terminal protein tag on a heterologous targeting peptide may facilitate purification of an AAV comprising the tagged heterologous targeting peptide.

In some embodiments, the AAV capsid protein further comprises a linker. In some embodiments, the linker is conjugated to the C-terminus of the N-terminally grafted heterologous targeting peptide. In some embodiments, the linker is conjugated to the N-terminus of the N-terminally grafted heterologous targeting peptide. In some embodiments, one linker is conjugated to the N-terminus of the N-terminally grafted heterologous targeting peptide and a second linker is conjugated to the C-terminus of the N-terminally grafted heterologous targeting peptide. In some embodiments, the linker is a glycine-rich linker. In some embodiments, the linker comprises at least two glycine residues. In some embodiments, the polypeptide repeat comprises GGGGS (SEQ ID NO: 28). In some embodiments, the linker comprises a formula selected from the group consisting of: $[G]_n$, $[G]_nS$, $[GS]_n$, and $[GGSG]_n$, wherein G is glycine and wherein n is an integer greater than one (e.g., 2, 3, 4, 5, 6, 7, 8, 9, 10, 11, 12, 13, 14, 15, 16, 17, 18, 19, 20, 21, 22, 23, 24, 25 or more). In some embodiments, n is an integer in a range of 2 to 10, 2 to 20, 5 to 10, 5 to 15, or 5 to 25. Accordingly, in some embodiments, a heterologous targeting peptides is conjugated to a linker. In some embodiments, heterologous targeting peptide is provided with an N terminal methionine, reflecting the amino acid residue corresponding to a start codon, for example. In some embodiments, peptides of the following peptide sequence are provided MAAAAAAAAAAAAAAAAAAAGGGGS (SEQ ID NO: 30); MAAAAAAAAAAAAAAAAAAA (SEQ ID NO: 31); and AAAAAAAAAAAAAAAAAAAGGGGS(SEQ ID NO: 32) and may be grafted within or to capsid proteins to alter targeting.

In some aspects, the disclosure relates to a recombinant AAV comprising an AAV capsid protein having an N-terminally grafted heterologous targeting peptide that mediates transcytosis across the blood-brain barrier. In some embodiments, transport of molecules across the blood brain barrier is mediated by lipoprotein receptor-related proteins (LRP) or suitable epitopes derived therefrom. LPRs are members of a large conserved family of endocytic receptors that bind and internalize a broad spectrum of ligands including but not limited to lipoproteins, proteinases, proteinase inhibitor complexes, viruses, bacterial toxins and extracellular matrix proteins. Non-limiting examples of LRPs include LRP1, LRP1B, LRP2 (megalin), LRP3, LRP4, LRP5, LRP6, LRP8 (apolipoprotein e receptor), LRP10, and Angiopep-2 and suitable fragments thereof. In some embodiments, the N-terminally grafted heterologous targeting peptides disclosed herein are LRP ligands. In some embodiments, the N-terminally grafted heterologous targeting peptide is Angiopep-2. In some embodiments, the N-terminally grafted heterologous targeting peptide is a polypeptide represented by SEQ ID NO:5. In some embodiments, the N-terminally grafted heterologous targeting peptide is encoded by the nucleic acid represented in SEQ ID NO:29. Other N-terminally grafted heterologous targeting peptides that mediate transcytosis across the blood-brain barrier are also contemplated herein.

In some embodiments, the N-terminally grafted heterologous targeting peptide is a polypeptide represented by SEQ ID NO: 7. In some embodiments, the N-terminally grafted heterologous targeting peptide is a polypeptide represented by the $[A]_n$, wherein A is alanine and n is an integer greater than 5 (e.g., 5, 6, 7, 8, 9, 10, 11, 12, 13, 14, 15, 16, 17, 18, 19, 20, 21, 22, 23, 24, 25, 26, 27, 28, 29, 30, 31 or more). In some embodiments, n is an integer in a range of 5 to 10, 5 to 11, 5 to 12, 5 to 13, 5 to 14, 5 to 15, 5 to 20, 5 to 25, 15 to 25, 15 to 30, 17 to 21 or 18 to 20.

In some cases, fragments of capsid proteins disclosed herein are provided. Such fragments may be at least 10, at least 20, at least 50, at least 100, at least 200, at least 300, at least 400, at least 500 or more amino acids in length. In some embodiments, chimeric capsid proteins are provided that comprise one or more fragments of one or more capsid proteins disclosed herein.

"Homology" refers to the percent identity between two polynucleotides or two polypeptide moieties. The term "substantial homology", when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences. When referring to a polypeptide, or fragment thereof, the term "substantial homology" indicates that, when optimally aligned with appropriate gaps, insertions or deletions with another polypeptide, there is nucleotide sequence identity in about 90 to 100% of the aligned sequences. The term "highly conserved" means at least 80% identity, preferably at least 90% identity, and more preferably, over 97% identity. In some cases, highly conserved may refer to 100% identity. Identity is readily determined by one of skill in the art by, for example, the use of algorithms and computer programs known by those of skill in the art.

As described herein, alignments between sequences of nucleic acids or polypeptides are performed using any of a variety of publicly or commercially available Multiple Sequence Alignment Programs, such as "Clustal W", accessible through Web Servers on the internet. Alternatively, Vector NTI utilities may also be used. There are also a number of algorithms known in the art which can be used to measure nucleotide sequence identity, including those contained in the programs described above. As another example, polynucleotide sequences can be compared using BLASTN, which provides alignments and percent sequence identity of the regions of the best overlap between the query and search sequences. Similar programs are available for the comparison of amino acid sequences, e.g., the "Clustal X" program, BLASTP. Typically, any of these programs are used at default settings, although one of skill in the art can alter these settings as needed. Alternatively, one of skill in the art can utilize another algorithm or computer program which provides at least the level of identity or alignment as that provided by the referenced algorithms and programs. Alignments may be used to identify corresponding amino acids between two proteins or peptides. A "corresponding amino acid" is an amino acid of a protein or peptide sequence that has been aligned with an amino acid of another protein or peptide sequence. Corresponding amino acids may be identical or non-identical. A corresponding amino acid that is a non-identical amino acid may be referred to as a variant amino acid.

Alternatively for nucleic acids, homology can be determined by hybridization of polynucleotides under conditions which form stable duplexes between homologous regions, followed by digestion with single-stranded-specific nuclease (s), and size determination of the digested fragments. DNA sequences that are substantially homologous can be identified in a Southern hybridization experiment under, for example, stringent conditions, as defined for that particular system. Defining appropriate hybridization conditions is within the skill of the art.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Furthermore, nucleic acids can be tailored for optimal gene expression based on optimization of nucleotide sequence to reflect the codon bias of a host cell. The skilled artisan appreciates that gene expression may be improved if codon usage is biased towards those codons favored by the host.

Recombinant AAVs

In some aspects, the disclosure provides isolated AAVs. As used herein with respect to AAVs, the term "isolated" refers to an AAV that has been artificially obtained or produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected. In some embodiments, the rAAV comprises a capsid protein having an amino acid sequence as set forth in any one of SEQ ID NOs 19-27, or a protein having substantial homology thereto.

In some embodiments, the rAAVs of the disclosure are pseudotyped rAAVs. Pseudotyping is the process of producing viruses or viral vectors in combination with foreign viral envelope proteins. The result is a pseudotyped virus particle. With this method, the foreign viral envelope proteins can be used to alter host tropism or an increased/decreased stability of the virus particles. In some aspects, a pseudotyped rAAV comprises nucleic acids from two or more different AAVs, wherein the nucleic acid from one AAV encodes a capsid protein and the nucleic acid of at least one other AAV encodes other viral proteins and/or the viral genome. In some embodiments, a pseudotyped rAAV refers to an AAV comprising an inverted terminal repeats (ITRs) of one AAV serotype and an capsid protein of a different AAV serotype. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

Methods for obtaining recombinant AAVs having a desired capsid protein are well known in the art. (See, for example, US Patent Application Publication No. US 2003/0138772, the contents of which are incorporated herein by reference in their entirety). Typically the methods involve culturing a host cell which contains a nucleic acid sequence encoding an AAV capsid protein (e.g., a nucleic acid having a sequence as set forth in any one of SEQ ID NOs 8-18 or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins endocoded by the cap gene of an AAV. In some embodiments, AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, capsid proteins protect a viral genome, deliver a genome and/or interact with a host cell. In some aspects, capsid proteins deliver the viral genome to a host in a tissue specific manner. In some embodiments, an N-terminally grafted heterologous targeting peptide is present on all three capsid proteins (e.g., VP1, VP2, VP3) of a rAAV. In some embodiments, an N-terminally grafted heterologous targeting peptide is present on two of the capsid proteins (e.g., VP2 and VP3) of a rAAV. In some embodiments, an N-terminally grafted heterologous targeting peptide is present on a single capsid protein of a rAAV. In some embodiments, an N-terminally grafted heterologous targeting peptide is present on the VP2 capsid protein of the rAAV.

In some embodiments, the disclosure relates to an adeno-associated virus (AAV) capsid protein comprising: an AAV capsid protein having an N-terminally grafted heterologous targeting peptide, wherein the AAV capsid protein is not of an AAV2 serotype.

In some embodiments, the AAV capsid protein is of an AAV serotype selected from the group consisting of AAV3, AAV4, AAV5, AAV6, AAV8, AAVrh8 AAV9, and AAV10. In some embodiments, the capsid protein having an N-terminally grafted heterologous targeting peptide is a viral protein 2 (VP2) capsid protein. In some embodiments, the AAV capsid protein having an N-terminally grafted heterologous targeting peptide is of a serotype derived from a non-human primate. In some embodiments, the AAV capsid protein having an N-terminally grafted heterologous targeting peptide is of a AAVrh8 serotype. In some embodiments, the AAV capsid protein having an N-terminally grafted heterologous targeting peptide is of an AAV9, optionally AAV9.47, serotype.

In some aspects, the disclosure relates to the location within an AAV capsid protein where a heterologous targeting peptide is grafted. In some embodiments, an heterologous targeting peptide is N-terminally grafted. In some embodiments, an N-terminally grafted heterologous targeting peptide is inserted before the fifth, fourth or third amino acid after the N-terminal amino acid of the capsid protein. In some embodiments, an N-terminally grafted heterologous targeting peptide is inserted before the second N-terminal amino acid of the capsid protein. In some embodiments, an N-terminally grafted heterologous targeting peptide is inserted after the first N-terminal amino acid of the capsid protein. In some embodiments, an N-terminally grafted heterologous targeting peptide is inserted after the first N-terminal methionine residue of the capsid protein.

In some embodiments, components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the disclosure relates to a host cell containing a nucleic acid that comprises a coding sequence selected from the group consisting of: SEQ ID NOs: 8-18 that is operably linked to a promoter. In some embodiments, the disclosure relates to a composition comprising the host cell described above. In some embodiments, the composition comprising the host cell above further comprises a cryopreservative.

The recombinant AAV vector, rep sequences, cap sequences, and helper functions useful for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced through the cell membrane. A number of transfection techniques are generally known in the art. See, e.g., Graham et al. (1973)

Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA, miRNA inhibitor) from a transcribed gene.

The foregoing methods for packaging recombinant vectors in desired AAV capsids to produce the rAAVs of the disclosure are not meant to be limiting and other suitable methods will be apparent to the skilled artisan.

Recombinant AAV Vectors

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

In some embodiments, the disclosure relates to a recombinant AAV (rAAV) comprising a capsid protein having an N-terminally grafted heterologous targeting peptide, wherein the N-terminally grafted heterologous targeting peptide is present only in the VP2 capsid protein. In some embodiments, the rAAV comprises a capsid protein having an amino acid sequence selected from the group consisting of: SEQ ID NOs: 19-27.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, one or more binding sites for one or more of miRNAs are incorporated in a transgene of a rAAV vector, to inhibit the expression of the transgene in one or more tissues of a subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Recombinant AAV Vector: Transgene Coding Sequences

The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

Also contemplated herein are methods of delivering a transgene to a subject using the rAAVs described herein. In some embodiments, the disclosure relates to a method for delivering a transgene to a subject comprising administering a rAAV to a subject, wherein the rAAV comprises: (i) a capsid protein having a sequence selected from SEQ ID NOs: 19-27, and (ii) at least one transgene, and wherein the rAAV infects cells of a target tissue of the subject. In some embodiments of the method, at least one transgene encodes a protein. In some embodiments, the protein is an immunoglobulin heavy chain or light chain or fragment thereof.

In some embodiments, at least one transgene encodes a small interfering nucleic acid. In some embodiments, the small interfering nucleic acid is a miRNA. In some embodiments, the small interfering nucleic acid is a miRNA sponge or TuD RNA that inhibits the activity of at least one miRNA in the subject or animal. In some embodiments, the miRNA is expressed in a cell of the target tissue. In some embodiments, the target tissue is skeletal muscle, heart, liver, pancreas, brain or lung. In some embodiments, the transgene expresses a transcript that comprises at least one binding site for a miRNA, wherein the miRNA inhibits activity of the transgene, in a tissue other than the target tissue, by hybridizing to the binding site.

Reporter sequences that may be provided in a transgene include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of an rAAV.

In some aspects, the disclosure provides rAAV vectors for use in methods of preventing or treating one or more genetic deficiencies or dysfunctions in a mammal, such as for example, a polypeptide deficiency or polypeptide excess in a mammal, and particularly for treating or reducing the severity or extent of deficiency in a human manifesting one or more of the disorders linked to a deficiency in such polypeptides in cells and tissues. The method involves administration of an rAAV vector that encodes one or more therapeutic peptides, polypeptides, siRNAs, microRNAs, antisense nucleotides, etc. in a pharmaceutically-acceptable carrier to the subject in an amount and for a period of time sufficient to treat the deficiency or disorder in the subject suffering from such a disorder.

Thus, the disclosure embraces the delivery of rAAV vectors encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16 IL-17, and IL-18.

The rAAV vectors may comprise a gene to be transferred to a subject to treat a disease associated with reduced expression, lack of expression or dysfunction of the gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase, associated with ornithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-galactosidase, associated with GM1 gangliosidosis; beta-hexosaminidase A and B, associated with Tay-Sachs disease and Sandhoff disease; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent porphyria; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppessor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

In some embodiments, the rAAV vectors may comprise a gene encoding an antigen-binding protein, such as an immunoglobulin heavy chain or light chain or fragment thereof, e.g., that may be used for therapeutic purposes. In some embodiments, the protein is a single chain Fv fragment or Fv-Fc fragment. Accordingly, in some embodiments, the rAAV can be used to infect cells are of target tissue (e.g., muscle tissue) to engineer cells of the tissue to express an antigen-binding protein, such as an antibody or fragment thereof. In some embodiments, to generate rAAVs that express the antibodies or antigen binding fragments, cDNAs engineered to express such proteins will be sucloned into an appropriate plasmid backbone and packaged into an rAAV.

In some embodiments, the rAAV vectors may comprise a gene or genes encoding genome editing enzymes or related molecules. As used herein, "genome editing" refers to adding, disrupting or changing genomic sequences (e.g., a gene sequence). In some embodiments, genome editing is performed using engineered proteins and related molecules. In some aspects, genome editing comprises the use of engineered nucleases to cleave a target genomic locus. In some embodiments, genome editing further comprises inserting, deleting, mutating or substituting nucleic acid residues at a cleaved locus. In some embodiments, inserting, deleting, mutating or substituting nucleic acid residues at a cleaved locus is accomplished through endogenous cellular mechanisms such as homologous recombination (HR) and non-homologous end joining (NHEJ). Exemplary genome editing technologies include, but are not limited to Transcription Activator-like Effector Nucleases (TALENs), Zinc Finger Nucleases (ZFNs), engineered meganuclease re-engineered homing endonucleases and the CRISPR/Cas system. In some embodiments, the rAAV may comprise a gene or genes encoding proteins or molecules related to TALENs, including but not limited to transcription activator-like effectors (TALEs) and restriction endonucleases (e.g., FokI). In some embodiments, the rAAV may comprise a gene or genes encoding proteins or molecules related to ZFNs, including but not limited to proteins comprising the $Cys_2His_2$ fold group (for example Zif268 (EGR1)), and restriction endonucleases (e.g., FokI). In some embodiments, the rAAV may comprise a gene or genes encoding proteins or molecules related to the CRISPR/Cas system, including but not limited to Cas9, Cas6, dCas9, CRISPR RNA (crRNA) and trans-activating crRNA (tracrRNA).

The rAAVs of the disclosure can be used to restore the expression of genes that are reduced in expression, silenced, or otherwise dysfunctional in a subject (e.g., a tumor suppressor that has been silenced in a subject having cancer). The rAAVs of the disclosure can also be used to knockdown the expression of genes that are aberrantly expressed in a subject (e.g., an oncogene that is expressed in a subject having cancer). In some embodiments, an rAAV vector comprising a nucleic acid encoding a gene product associated with cancer (e.g., tumor suppressors) may be used to treat the cancer, by administering a rAAV harboring the rAAV vector to a subject having the cancer. In some embodiments, an rAAV vector comprising a nucleic acid encoding a small interfering nucleic acid (e.g., shRNAs, miRNAs) that inhibits the expression of a gene product associated with cancer (e.g., oncogenes) may be used to treat the cancer, by administering a rAAV harboring the rAAV vector to a subject having the cancer. In some embodiments, a rAAV vector comprising a nucleic acid encoding a gene product associated with cancer (or a functional RNA that inhibits the expression of a gene associated with cancer) may be used for research purposes, e.g., to study the cancer or to identify therapeutics that treat the cancer. The following is a non-limiting list of exemplary genes known to be associated with the development of cancer (e.g., oncogenes and tumor suppressors): AARS, ABCB1, ABCC4, ABI2, ABL1, ABL2, ACK1, ACP2, ACY1, ADSL, AK1, AKR1C2, AKT1, ALB, ANPEP, ANXA5, ANXA7, AP2M1, APC, ARHGAP5, ARHGEF5, ARID4A, ASNS, ATF4, ATM, ATP5B, ATP5O, AXL, BARD1, BAX, BCL2, BHLHB2, BLMH, BRAF, BRCA1, BRCA2, BTK, CANX, CAP1, CAPN1, CAPNS1, CAV1, CBFB, CBLB, CCL2, CCND1, CCND2, CCND3, CCNE1, CCT5, CCYR61, CD24, CD44, CD59, CDC20, CDC25, CDC25A, CDC25B, CDC2L5, CDK10, CDK4, CDK5, CDK9, CDKL1, CDKN1A, CDKN1B, CDKN1C, CDKN2A, CDKN2B, CDKN2D, CEBPG, CENPC1, CGRRF1, CHAF1A, CIB1, CKMT1, CLK1, CLK2, CLK3, CLNS1A, CLTC, COL1A1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR1, EIF5, EPHA2, ERBB2, ERBB3, ERBB4, ERCC3, ETV1, ETV3, ETV6, F2R, FASTK, FBN1, FBN2, FES, FGFR1, FGR, FKBP8, FN1, FOS, FOSL1, FOSL2, FOXG1A, FOXO1A, FRAP1, FRZB, FTL, FZD2, FZD5, FZD9, G22P1, GAS6, GCN5L2, GDF15, GNA13, GNAS, GNB2, GNB2L1, GPR39, GRB2, GSK3A, GSPT1, GTF2I, HDAC1, HDGF, HMMR, HPRT1, HRB, HSPA4, HSPA5, HSPA8, HSPB1, HSPH1, HYAL1, HYOU1, ICAM1, ID1, ID2, IDUA, IER3, IFITM1, IGF1R, IGF2R, IGFBP3, IGFBP4, IGFBP5, IL1B, ILK, ING1, IRF3, ITGA3, ITGA6, ITGB4, JAK1, JARID1A, JUN, JUNB, JUND, K-ALPHA-, KIT, KITLG, KLK10, KPNA2, KRAS2, KRT18, KRT2A, KRT9, LAMB1, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB1, NFKB2, NFSF7, NID, NINJ1, NMBR, NME1, NME2, NME3, NOTCH1, NOTCH2, NOTCH4, NPM1, NQO1, NR1D1, NR2F1, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PPIH, PPP1CA, PPP2R5A, PRDX2, PRDX4, PRKAR1A, PRKCBP1, PRNP, PRSS15, PSMA1, PTCH, PTEN, PTGS1, PTMA, PTN, PTPRN, RAB5A, RAC1, RAD50, RAF1, RALBP1, RAP1A, RARA, RARB, RASGRF1, RB1, RBBP4, RBL2, REA, REL, RELA, RELB, RET, RFC2, RGS19, RHOA, RHOB, RHOC, RHOD, RIPK1, RPN2, RPS6KB1, RRM1, SARS, SELENBP1, SEMA3C, SEMA4D, SEPP1, SERPINHI, SFN, SFPQ, SFRS7, SHB, SHH, SIAH2, SIVA, SIVA TP53, SKI, SKIL, SLC16A1, SLC1A4, SLC20A1, SMO, SMPD1, SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFA, TGFB1, TGFBI, TGFBR2, TGFBR3, THBS1, TIE, TIMP1, TIMP3, TJP1, TK1, TLE1, TNF, TNFRSF10A, TNFRSF10B, TNFRSF1A, TNFRSF1B, TNFRSF6, TNFSF7, TNK1, TOB1, TP53, TP53BP2, TP53I3, TP73, TPBG, TPT1, TRADD, TRAM1, TRRAP, TSG101, TUFM, TXNRD1, TYRO3, UBC, UBE2L6, UCHL1, USP7, VDAC1, VEGF, VHL, VIL2, WEE1, WNT1, WNT2, WNT2B, WNT3, WNT5A, WT1, XRCCl, YES1, YWHAB, YWHAZ, ZAP70, and ZNF9.

A rAAV vector may comprise as a transgene, a nucleic acid encoding a protein or functional RNA that modulates apoptosis. The following is a non-limiting list of genes associated with apoptosis and nucleic acids encoding the products of these genes and their homologues and encoding small interfering nucleic acids (e.g., shRNAs, miRNAs) that inhibit the expression of these genes and their homologues are useful as transgenes in certain embodiments of the disclosure: RPS27A, ABL1, AKT1, APAF1, BAD, BAG1, BAG3, BAG4, BAK1, BAX, BCL10, BCL2, BCL2A1, BCL2L1, BCL2L10, BCL2L11, BCL2L12, BCL2L13, BCL2L2, BCLAF1, BFAR, BID, BIK, NAIP, BIRC2, BIRC3, XIAP, BIRC5, BIRC6, BIRC7, BIRC8, BNIP1, BNIP2, BNIP3, BNIP3L, BOK, BRAF, CARD10, CARD11, NLRC4, CARD14, NOD2, NOD1, CARD6, CARD8, CARD9, CASP1, CASP10, CASP14, CASP2, CASP3, CASP4, CASP5, CASP6, CASP7, CASP8, CASP9, CFLAR, CIDEA, CIDEB, CRADD, DAPK1, DAPK2, DFFA, DFFB, FADD, GADD45A, GDNF, HRK, IGF1R, LTA, LTBR, MCL1, NOL3, PYCARD, RIPK1, RIPK2, TNF, TNFRSF10A, TNFRSF10B, TNFRSF10C, TNFRSF10D, TNFRSF11B, TNFRSF12A, TNFRSF14, TNFRSF19, TNFRSF1A, TNFRSF1B, TNFRSF21, TNFRSF25, CD40, FAS, TNFRSF6B, CD27, TNFRSF9, TNFSF10, TNFSF14, TNFSF18, CD40LG, FASLG, CD70, TNFSF8, TNFSF9, TP53, TP53BP2, TP73, TP63, TRADD, TRAF1, TRAF2, TRAF3, TRAF4, and TRAF5.

In some aspects, the disclosure relates to methods and compositions for treating CNS-related disorders. As used herein, a "CNS-related disorder" is a disease or condition of the central nervous system. A CNS-related disorder may affect the spinal cord (e.g., a myelopathy), brain (e.g., a encephalopathy) or tissues surrounding the brain and spinal cord. A CNS-related disorder may be of a genetic origin, either inherited or acquired through a somatic mutation. A CNS-related disorder may be a psychological condition or disorder, e.g., Attention Deficit Hyperactivity Disorder, Autism Spectrum Disorder, Mood Disorder, Schizophrenia, Depression, Rett Syndrome, etc. A CNS-related disorder may be an autoimmune disorder. A CNS-related disorder may also be a cancer of the CNS, e.g., brain cancer. A CNS-related disorder that is a cancer may be a primary cancer of the CNS, e.g., an astrocytoma, glioblastomas, etc., or may be a cancer that has metastasized to CNS tissue, e.g., a lung cancer that has metastasized to the brain. Further non-limiting examples of CNS-related disorders, include Huntington's disease, Parkinson's Disease, Lysosomal Storage Disease, Ischemia, Neuropathic Pain, Amyotrophic lateral sclerosis (ALS), Multiple Sclerosis (MS), and Canavan disease (CD).

In some embodiments, the disclosure relates to a rAAV vector comprising a transgene, a nucleic acid encoding a protein or functional RNA useful for the treatment of a condition, disease or disorder associated with the central nervous system (CNS). The following is a non-limiting list of genes associated with CNS disease: DRD2, GRIA1, GRIA2, GRIN1, SLC1A1, SYP, SYT1, CHRNA7, 3Rtau/4rTUS, APP, BAX, BCL-2, GRIK1, GFAP, IL-1, AGER, associated with Alzheimer's Disease; UCH-L1, SKP1, EGLN1, Nurr-1, BDNF, TrkB, gstm1, S106β, associated with Parkinson's Disease; huntingtin (Htt), IT15, PRNP, JPH3, TBP, ATXN1, ATXN2, ATXN3, Atrophin 1, FTL, TITF-1, associated with Huntington's Disease; FXN, associated with Freidrich's ataxia; ASPA, associated with Canavan's Disease; DMD, associated with muscular dystrophy; and SMN1, UBE1, DYNC1H1 associated with spinal muscular atrophy.

The skilled artisan will also realize that in the case of transgenes encoding proteins or polypeptides, that mutations that results in conservative amino acid substitutions may be made in a transgene to provide functionally equivalent variants, or homologs of a protein or polypeptide. In some aspects the disclosure embraces sequence alterations that result in conservative amino acid substitution of a transgene. In some embodiments, the transgene comprises a gene having a dominant negative mutation. For example, a transgene may express a mutant protein that interacts with the same elements as a wild-type protein, and thereby blocks some aspect of the function of the wild-type protein.

Useful transgene products also include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful as transgenes or as targets for small interfering nucleic acids encoded by transgenes (e.g., miRNA sponges, antisense oligonucleotides, TuD RNAs) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-30 b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-5481, hsa-miR-548m, hsa-miR-548n, hsa-miR-548o, hsa-miR-548p, hsa-miR-549, hsa-miR-550, hsa-miR-550*, hsa-miR-551a, hsa-miR-55 b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

A "miRNA Inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex. MicroRNA inhibitors can be expressed in cells from a transgenes of a rAAV vector, as discussed above. MicroRNA sponges specifically inhibit miRNAs through a complementary heptameric seed sequence (Ebert, M. S. Nature Methods, Epub Aug. 12, 2007; ). In some embodiments, an entire family of miRNAs can be silenced using a single sponge sequence. TuD RNAs achieve efficient and long-term-suppression of specific miR-NAs in mammalian cells (See, e.g., Takeshi Haraguchi, et al., Nucleic Acids Research, 2009, Vol. 37, No. 6 e43, the contents of which relating to TuD RNAs are incorporated herein by reference). Other methods for silencing miRNA function (derepression of miRNA targets) in cells will be apparent to one of ordinary skill in the art.

In some embodiments, the cloning capacity of the recombinant RNA vector may limited and a desired coding sequence may require the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Somatic Transgenic Animal Models Produced Using rAAV-Based Gene Transfer

The disclosure also involves the production of somatic transgenic animal models of disease using recombinant Adeno-Associated Virus (rAAV) based methods. The methods are based, at least in part, on the observation that AAV serotypes and variants thereof mediate efficient and stable gene transfer in a tissue specific manner in adult animals. The rAAV elements (capsid, promoter, transgene products) are combined to achieve somatic transgenic animal models that express a stable transgene in a time and tissue specific manner. The somatic transgenic animal produced by the methods of the disclosure can serve as useful models of human disease, pathological state, and/or to characterize the effects of gene for which the function (e.g., tissue specific, disease role) is unknown or not fully understood. For example, an animal (e.g., mouse) can be infected at a distinct developmental stage (e.g., age) with a rAAV comprising a capsid having a specific tissue targeting capability (e.g., liver, heart, pancreas) and a transgene having a tissue specific promoter driving expression of a gene involved in disease. Upon infection, the rAAV infects distinct cells of the target tissue and produces the product of the transgene.

In some embodiments, the sequence of the coding region of a transgene is modified. The modification may alter the function of the product encoded by the transgene. The effect of the modification can then be studied in vivo by generating a somatic transgenic animal model using the methods disclosed herein. In some embodiments, modification of the sequence of coding region is a nonsense mutation that results in a fragment (e.g., a truncated version). In other cases, the modification is a missense mutation that results in an amino acid substitution. Other modifications are possible and will be apparent to the skilled artisan.

In some embodiments, the transgene causes a pathological state. A transgene that causes a pathological state is a gene whose product has a role in a disease or disorder (e.g., causes the disease or disorder, makes the animal susceptible to the disease or disorder) and/or may induce the disease or disorder in the animal. The animal can then be observed to evaluate any number of aspects of the disease (e.g., progression, response to treatment, etc.). These examples are not meant to be limiting, other aspects and examples are disclosed herein and described in more detail below.

The disclosure in some aspects, provide methods for producing somatic transgenic animal models through the targeted destruction of specific cell types. For example, models of type 1 diabetes can be produced by the targeted destruction of pancreatic Beta-islets. In other examples, the targeted destruction of specific cell types can be used to evaluate the role of specific cell types on human disease. In this regard, transgenes that encode cellular toxins (e.g., diphtheria toxin A (DTA)) or pro-apoptotic genes (NTR, Box, etc.) can be useful as transgenes for functional ablation of specific cell types. Other exemplary transgenes, whose products kill cells are embraced by the methods disclosed herein and will be apparent to one of ordinary skill in the art.

The disclosure in some aspects, provides methods for producing somatic transgenic animal models to study the long-term effects of over-expression or knockdown of genes. The long term over expression or knockdown (e.g., by shRNA, miRNA, miRNA inhibitor, etc.) of genes in specific target tissues can disturb normal metabolic balance and establish a pathological state, thereby producing an animal model of a disease, such as, for example, cancer. The disclosure in some aspects, provides methods for producing somatic transgenic animal models to study the long-term effects of over-expression or knockdown of gene of potential oncogenes and other genes to study tumorigenesis and gene function in the targeted tissues. Useful transgene products include proteins that are known to be associated with cancer and small interfering nucleic acids inhibiting the expression of such proteins. Other suitable transgenes may be readily selected by one of skill in the art provided that they are useful for creating animal models of tissue-specific pathological state and/or disease.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

Aspects of the disclosure relate to compositions comprising a recombinant AAV comprising a heterologous targeting peptide. In some embodiments, the heterologous targeting peptide is N-terminally grafted onto a capsid protein. In some embodiments, the an N-terminally grafted heterologous targeting peptide is present on all three capsid proteins (e.g., VP1, VP2, VP3) of the rAAV. In some embodiments, the N-terminally grafted heterologous targeting peptide is present on two of the capsid proteins (e.g., VP2 and VP3) of the rAAV. In some embodiments, the N-terminally grafted heterologous targeting peptide is present on a single capsid protein of the rAAV. In some embodiments, the N-terminally grafted heterologous targeting peptide is present on the VP2 capsid protein of the rAAV. In some embodiments, the composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., $\sim 10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Methods of Treating Huntington's Disease

Without wishing to be bound by any particular theory, rAAV comprising N-terminally grafted heterologous targeting peptides may be therapeutically effective for treating CNS-associated diseases, such as Huntington's disease. Thus, the disclosure relates, in some aspects, to methods of treating Huntington's disease.

In some embodiments, the disclosure provides a method of treating Huntington's disease, the method comprising administering to a subject having or suspected of having Huntington's disease an rAAV comprising (i) an N-terminally grafted heterologous targeting peptide and (ii) a transgene encoding an inhibitory RNA targeting a Huntington's disease-associated protein. In some embodiments, the N-terminally grafted heterologous targeting peptide is represented by SEQ ID NO: 7. In some embodiments, the transgene encodes an shRNA or microRNA that hybridizes to and inhibits activity of huntingtin (Htt) protein. In some embodiments, the transgene comprises a nucleic acid having a sequence set forth in SEQ ID NO: 33. In some embodiments, the transgene encodes a protein that suppresses or modulates Htt activity or expression. For example, in some embodiments, the transgene encodes a zinc finger protein that binds specifically to an expanded CAG repeat allele of an Htt gene and suppresses Htt expression. In some embodiments, the trandgene encodes a protein that modulates protein processing of Htt in cells, for example, XBP1.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the disclosure relates to a kit for producing a rAAV, the kit comprising a container housing an isolated nucleic acid having a sequence of any one of SEQ ID NOs: 8-18. In some embodiments, the kit further comprises instructions for producing the rAAV. In some embodiments, the kit further comprises at least one container housing a recombinant AAV vector, wherein the recombinant AAV vector comprises a transgene.

In some embodiments, the disclosure relates to a kit comprising a container housing a recombinant AAV having an isolated AAV capsid protein having an amino acid sequence as set forth in any of SEQ ID NOs: 19-27.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1

Figure 1B:
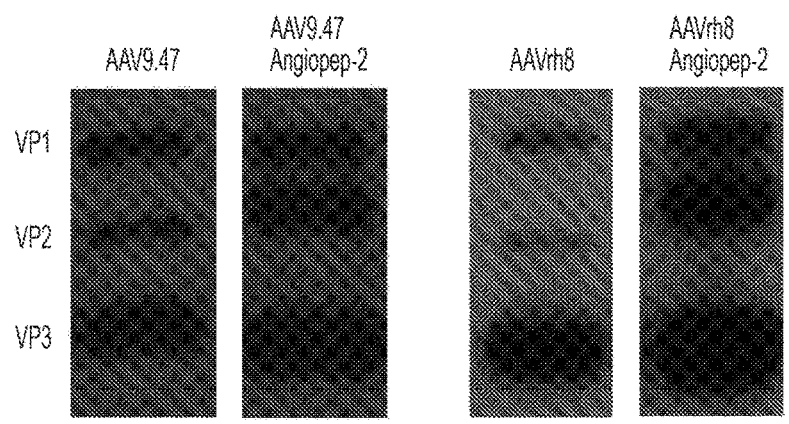
FIG. 1B depicts expression of capsid proteins VP1, VP2 and VP3 from AAV9.47 and AAVrh8. Western blot analysis demonstrates successful expression of VP2 capsid protein containing the Angiopep-2 (BTP) insert in both parent capsids (AAV9.47 and AAVrh8) and confirms correct stoichiometry of all three capsid proteins.

Peptide Grafting Yields Novel AAV Vectors Capable of Enhanced Neuronal Transduction Several AAV capsids were re-engineered by genetic grafting of different peptides into the capsid—naturally occurring AAVrh8, and a liver de-targeted AAV9 mutant, AAV9.47. Table 1 shows a list of the re-engineered AAV capsids. Angiopep-2 has been reported to be capable of crossing the blood brain barrier by transcytosis. Both capsids tolerated the insertion of Angiopep-2 (BTP) in the N-terminus of VP2 capsid protein and the modified capsids were packaged using an approach in which VP2 is expressed from one plasmid and VP1 and VP3 are expressed from another plasmid at stoichiometric ratios comparable to expressing all three capsid proteins from a single plasmid (FIG. 1A). High titer recombinant self-complementary vectors encoding GFP under a CBA promoter were generated in this manner, and western blot analysis confirmed the correct stoichiometry of all three capsid proteins (FIG. 1B).

TABLE 1

List of peptides inserted in VP2 of AAVrh8 or AAV9.47

| Peptide | Parental caspid | Effect on CNS tropism | Peptide amino acid sequence | SEQ ID NO. |
|---|---|---|---|---|
| FC5 | AAVrh8 | Reduce | EVQLQASGGGLVQAGGSLRLSC AASGFKITHYTMGWFRQAPGKE REFVSRITWGGDNTFYSNSVKG RFTISRDNAKNTVYLQMNSLKP EDTADYYCAAGSTSTATPLRVD YWGKGTQVTVSS | 1 |
| FC44 | AAVrh8 | Reduce | EVQLQASGGGLVQAGGSLRLSC SASVRTFSIYAMGWFRQAPGKE REFVAGINRSGDVTKYADFVKG RFSISRDNAKNMVYLQMNSLKP EDTALYYCAATWAYDTVGALTS GYNFWGQGTQVTVSS | 2 |
| ApoB100 | AAVrh8 | No effect | PSSVIDALQYKLEGTTRLTRKR GLKLATALSLSNKFVEGSPS | 3 |
| RVG | AAVrh8 | No effect | YTIVVMPENPRPGTPCDIFTNS RGKRASNG | 4 |
| Angio-pep-2 | AAVrh8 | Increase | TFFYGGSRGKRNNFKTEEY | 5 |
| ICAMg3 | AAV9.47 | No effect | NNQKIVNLKEKVAQLEA | 6 |
| RVG | AAV9.47 | No effect | YTIVVMPENPRPGTPCDIFTNS RGKRASNG | 4 |
| Angio-pep-2 | AAV9.47 | Increase | TFFYGGSRGKRNNFKTEEY | 5 |
| A-string | AAV9.47 | Increase | AAAAAAAAAAAAAAAAAAA | 7 |

Figure 2:
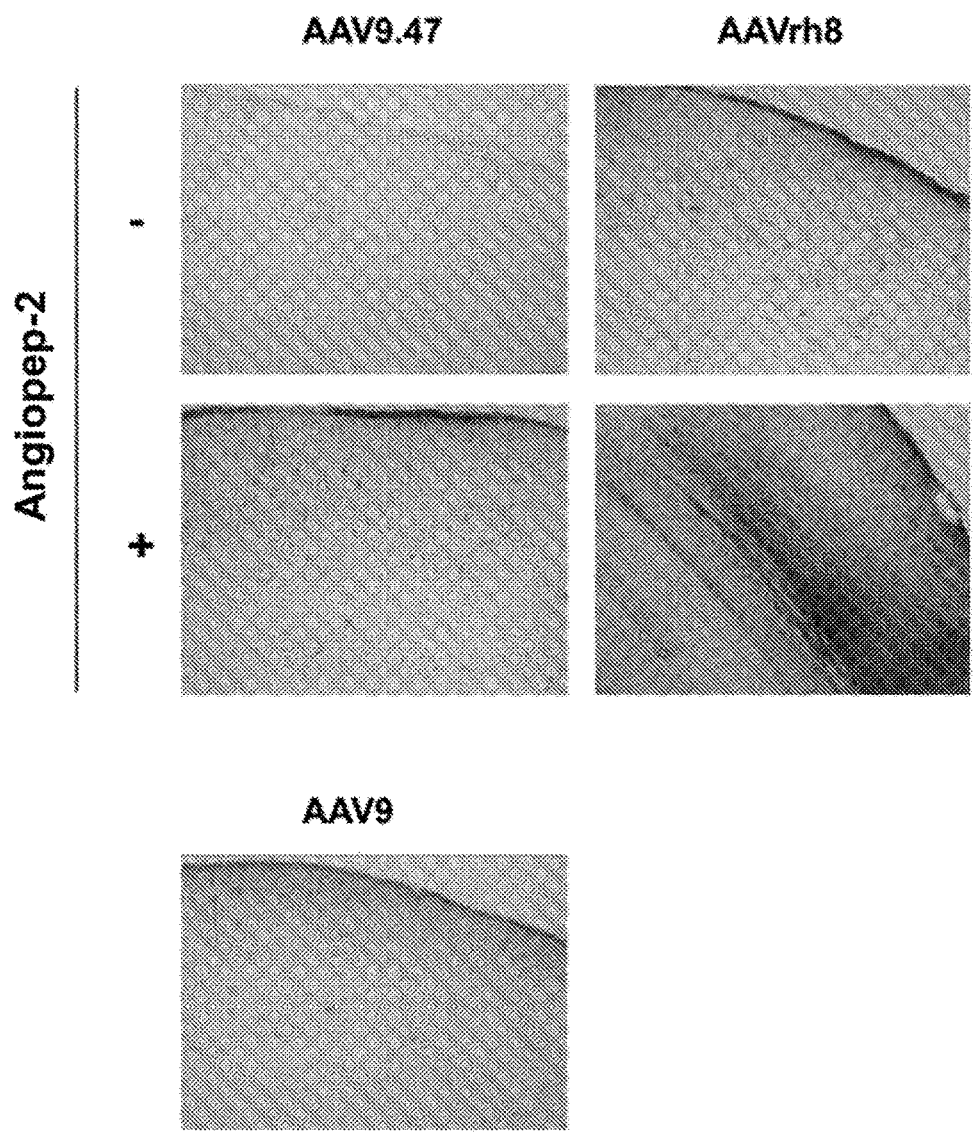
FIG. 2 depicts increased biodistribution of vectors containing Angiopep-2-grafted VP2 capsid proteins. Both Angiopep-2-grafted AAV vectors (AAV9.47, AAVrh8) transduced brain endothelium, gl
Figure 3:
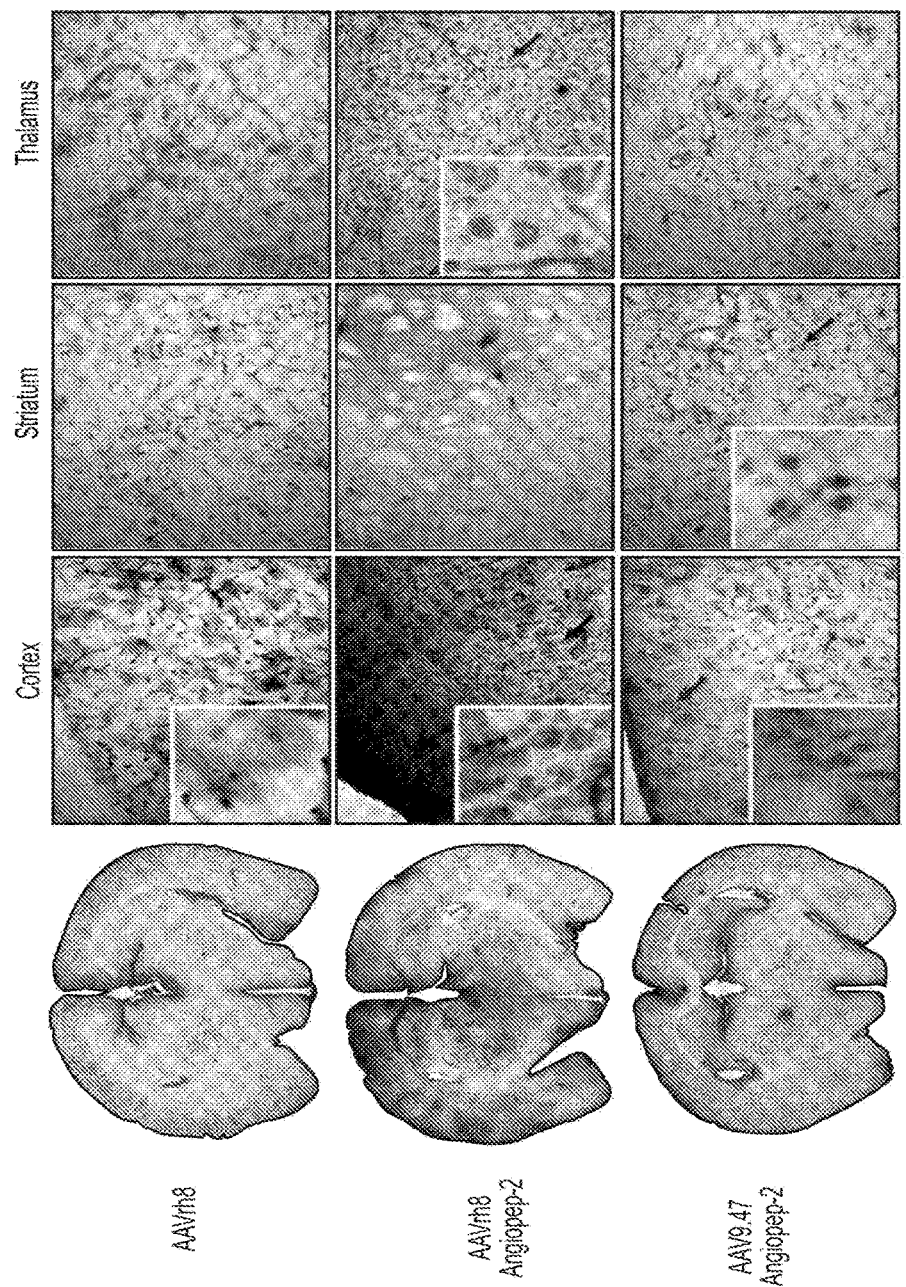
FIG. 3 depicts enhanced neural tropism of Angiopep-2-grafted AAV vectors. Control AAVrh8 vector transduced neurons in the visual cortex but not the striatum or thalamic region. The Angipep-2-grafted AAVrh8 vector transduced thalamic neurons and neurons in the visual cortex, while neurons in the striatum were transduced only by the Angiopep-2-grafted AAV9.47 vector. Both AAV vectors transduced brain endothelium, glia and cortical neurons at exceptionally high efficiency.
Figure 4:
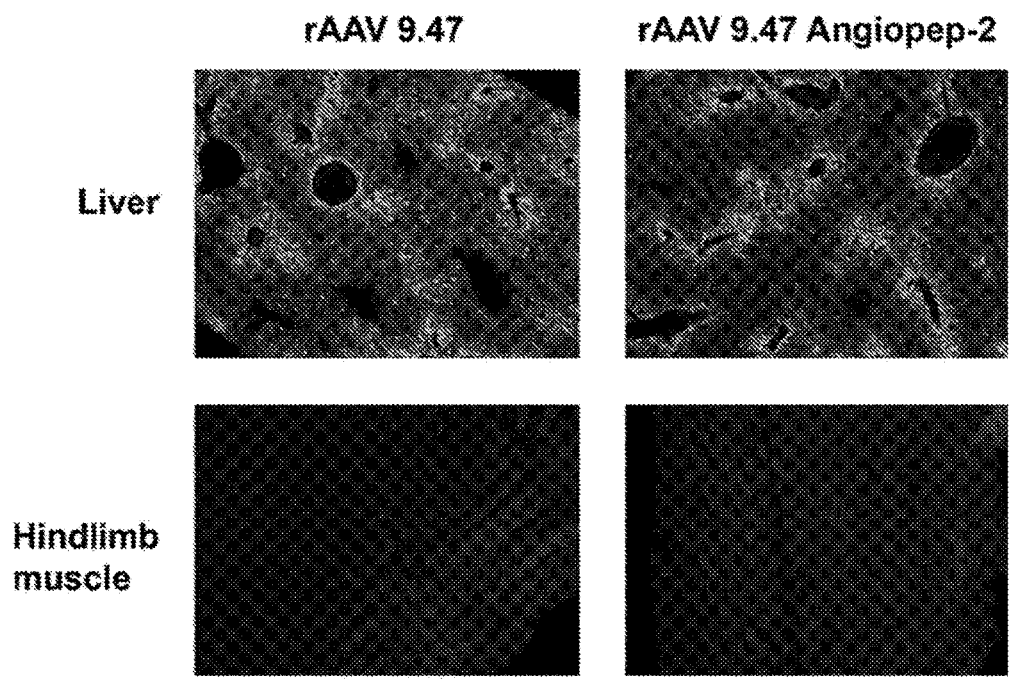
FIG. 4 depicts results showing that angiopep-2-grafted AAV vectors do not exhibit increased transduction of non-target peripheral tissues when compared to parent capsid control vectors.

The biodistribution of the two re-engineered vectors was assessed by systemic infusion via tail vein in 6-8 week-old C57BL/6 mice at a dose of 5E11 vg. Four weeks post-infusion, significant increase in CNS transduction was observed for both re-engineered capsids compared to the parent capsids (FIG. 2). Both new AAV vectors transduced brain endothelium, glia and cortical neurons at exceptional high efficiency. Insertion of other brain penetrating peptides, e.g., RVG, ICAMg3, ApoB 100, etc. in the context of either parent capsid did not lead to increased CNS transduction at levels comparable to angiopep-2. Remarkably, different neuronal populations were targeted by the same peptide in different capsid backgrounds. The re-engineered AAVrh8 vector transduced thalamic neurons and neurons in the visual cortex, while neurons in the striatum were transduced only by the re-engineered AAV9.47 vector (FIG. 3). This indicates that the enhanced neural tropism of these new AAV vectors is a function of the interplay between peptide and capsid. Transduction of thalamic and striatal neurons was not observed upon dose-matched administration of the native capsids or AAV9. Importantly, no increase in transduction of non-target peripheral tissues was observed with the re-engineered capsids (FIG. 4).

Figure 5:
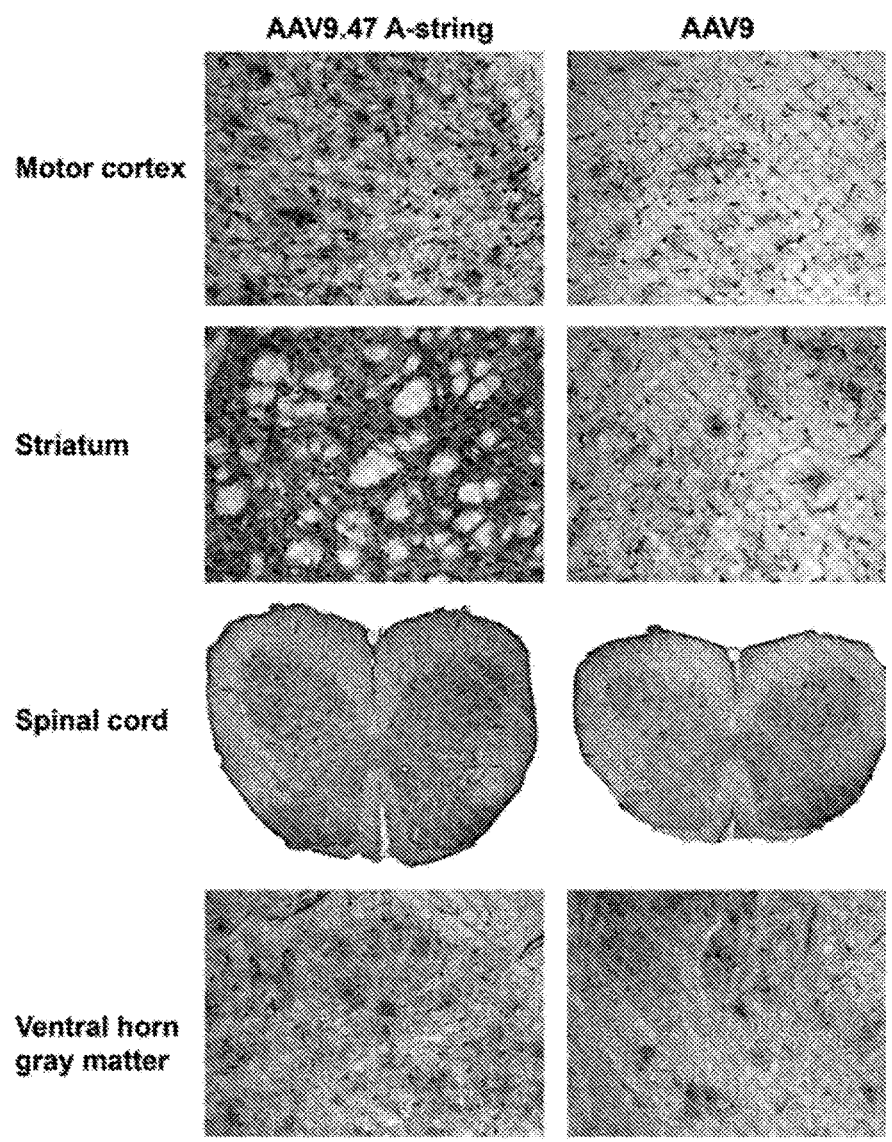
FIG. 5 depicts insertion of a 19-amino acid alanine string "A-string" (AS) in the N-terminal domain of the VP2 capsid protein of AAV9.47 increases CNS tropism. AS-grafted rAAV9.47 transduces cortical and striatal neurons in the brain at unprecedented efficiency, while motor neurons and interneurons were transduced in the spinal cord.
Figure 6:
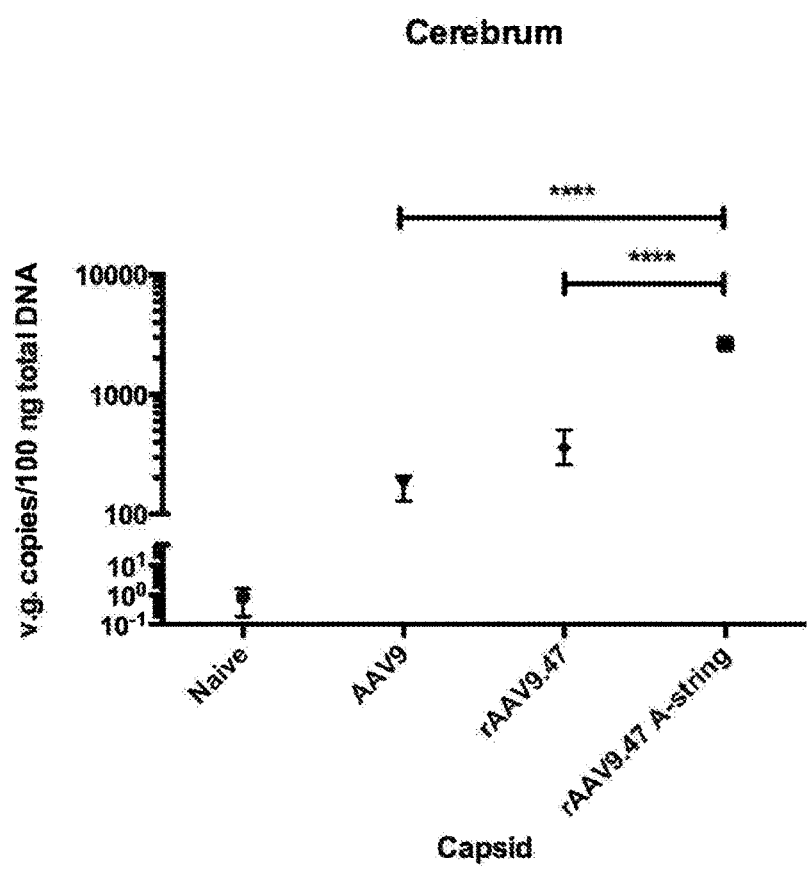
FIG. 6 depicts AS-grafted rAAV9.47 transduces the cerebrum and spinal cord more efficiently than AAV9 and non-grafted rAAV9.47. Significantly more vector genomes were present in the cerebrum and spinal cord of samples transduced with AS-grafted rAAV9.47 than in control samples transfected with AAV9.
Figure 6:
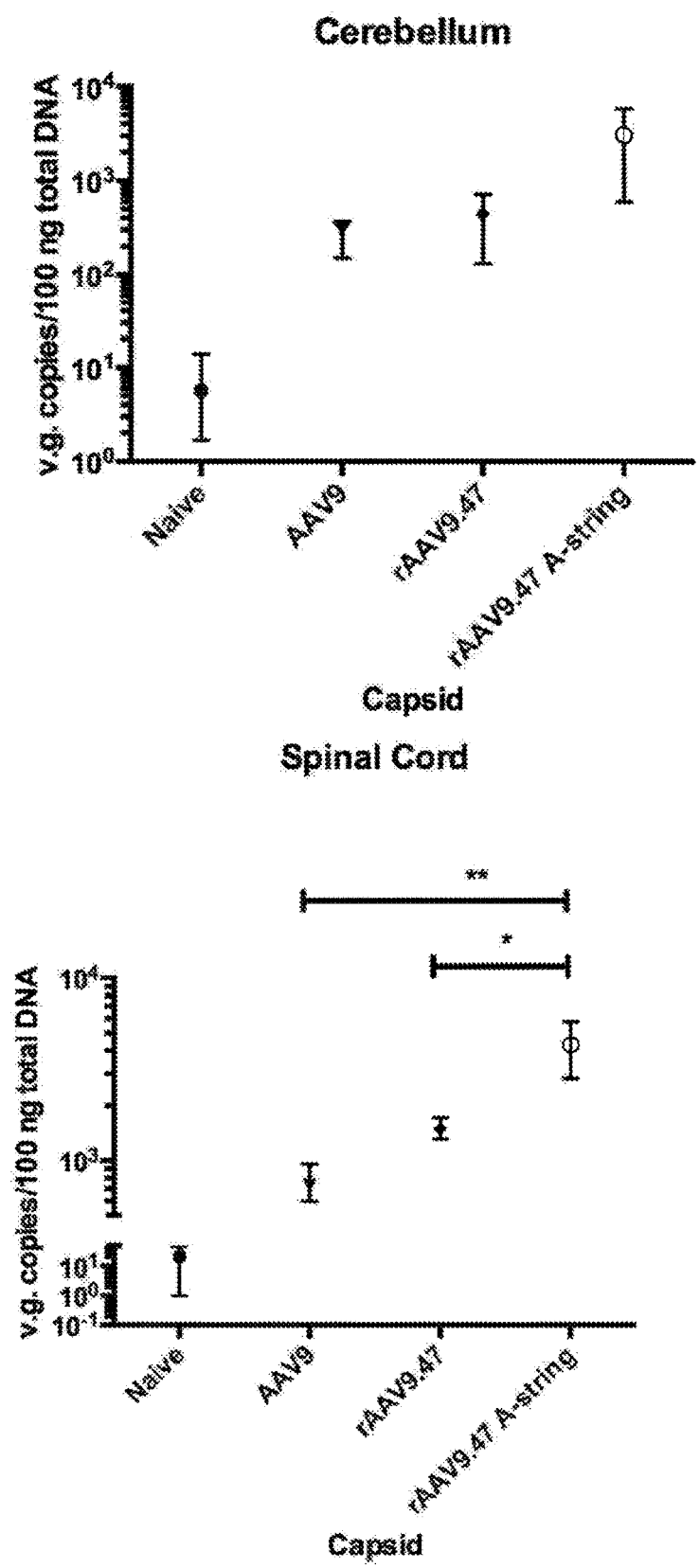
Figure 7:
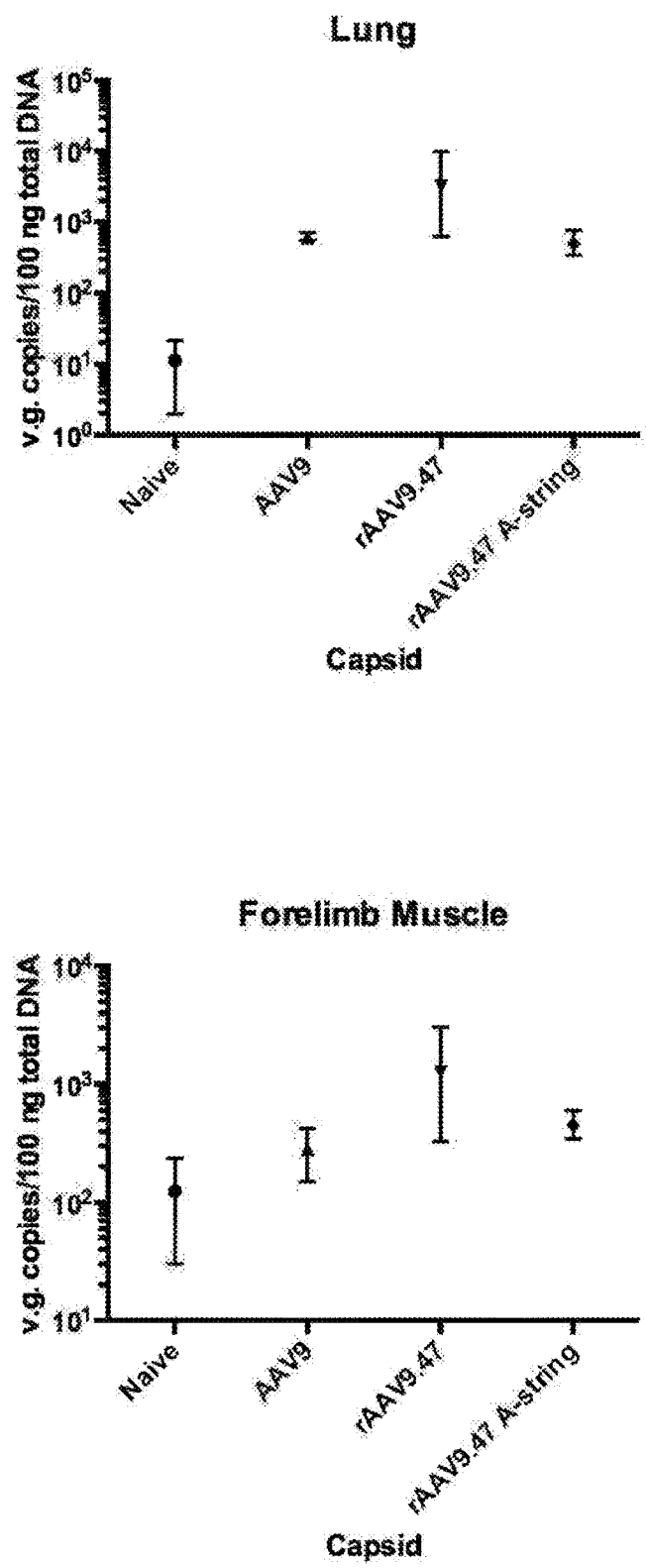
FIG. 7 depicts high efficiency transduction by AS-grafted rAAV9.47 in CNS tissue does not have increased off-target effects. No significant difference in vector genomes was observed between rAAV9.47-AS and AAV9 in non-target peripheral tissues (liver, skeletal muscle, heart, lung, kidney, pancreas and spleen).
Figure 7:
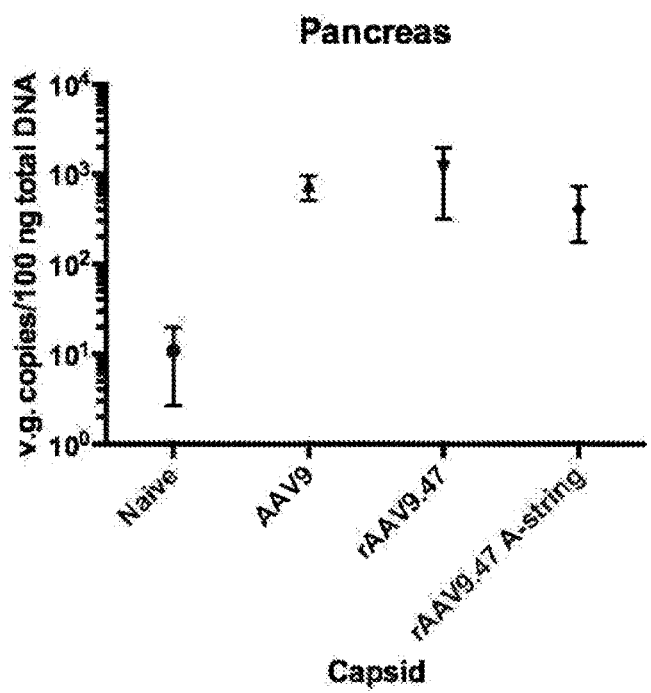
Figure 7:
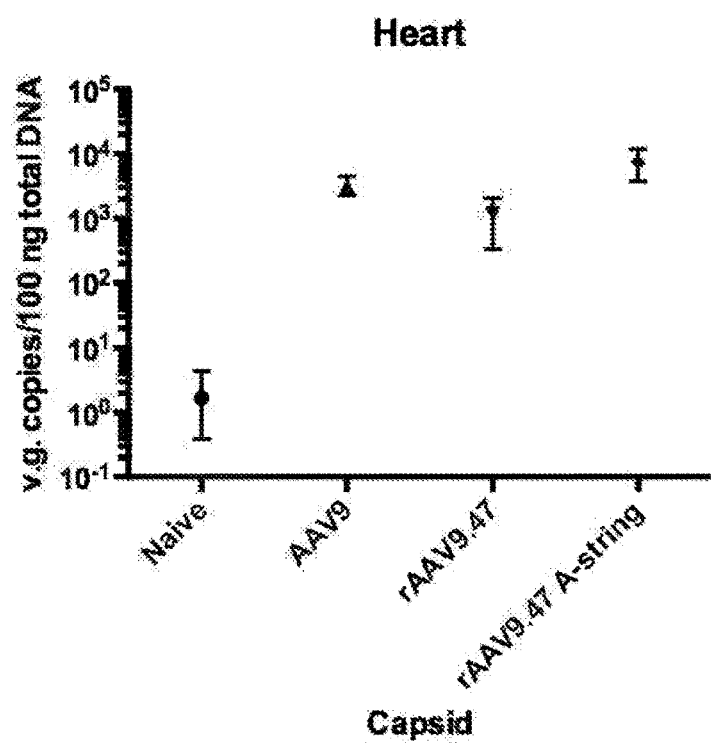
Figure 7:
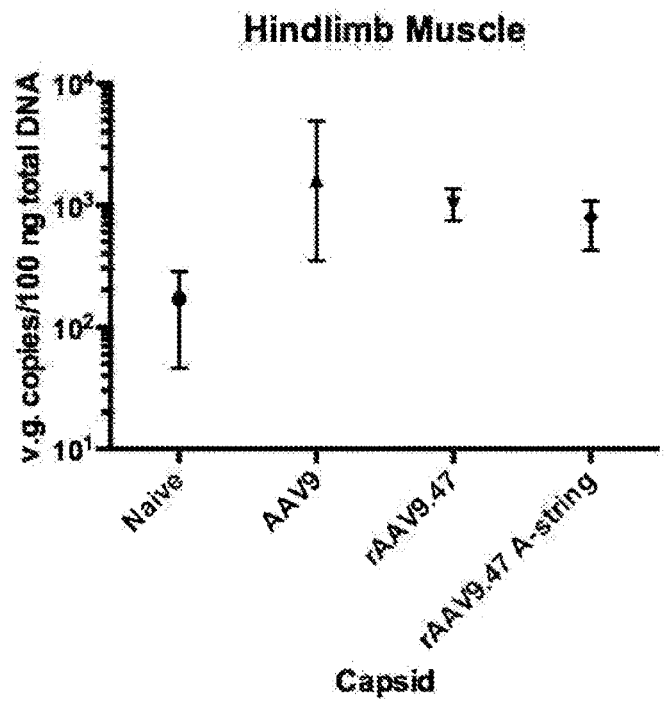
Figure 7:
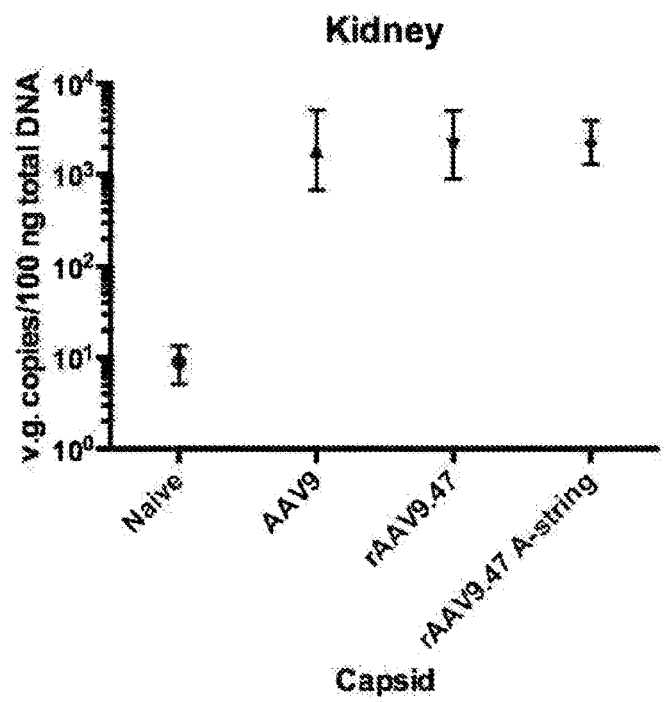
Figure 7:
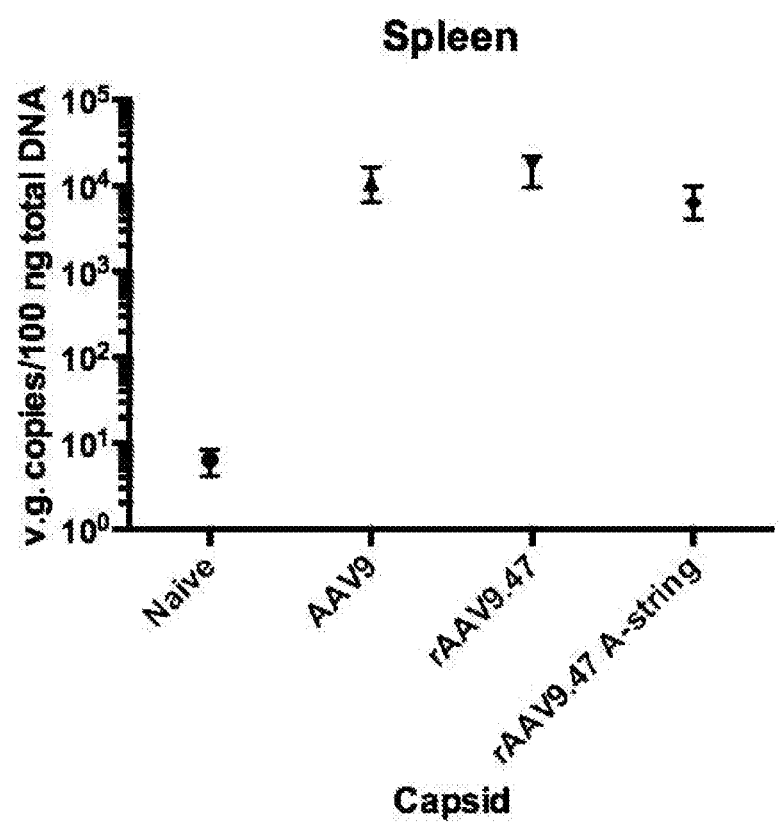

Unexpectedly, the insertion of a 19-amino acid alanine "string" (AS) in the VP2 capsid protein of AAV9.47 further increased CNS tropism compared to the Angiopep-2-carrying counterpart. Cortical and striatal neurons were transduced in the brain at an unprecedented efficiency, while motor neurons and interneurons were transduced in the spinal cord (FIG. 5). Significantly more vector genomes were found in the cerebrum and spinal cord of AS-grafted rAAV9.47 (rAAV9.47-AS), compared to AAV9 (15-fold and 6-fold, respectively) (FIG. 6). Importantly, no significant difference in vector genomes was observed in non-target peripheral tissues (liver, skeletal muscle, heart, lung, kidney, pancreas and spleen) between rAAV9.47-AS and AAV9 (FIG. 7).

Example 2

Widespread CNS Gene Transfer and Silencing after Systemic Delivery of a Novel AAV Vector Effective gene delivery to the central nervous system (CNS) is vital for development of novel gene therapies for neurological diseases. Adeno-associated virus (AAV) vectors have emerged as an effective platform for in vivo gene transfer, but overall neuronal transduction efficiency of vectors derived from naturally occurring AAV capsids after systemic administration is relatively low. Here, the possibility of enhancing CNS transduction of existing AAV capsids by genetically fusing peptides to the N-terminus of VP2 capsid protein was investigated. A novel vector AAV-AS, generated by the insertion of a poly-alanine peptide, is capable of extensive gene transfer throughout the CNS after systemic administration in adult mice. AAV-AS transduced 36% of striatal neurons, which is 80-fold higher than AAV9. Widespread neuronal transduction was also documented in cat brain after systemic infusion of AAV-AS. A single intravenous injection of an AAV-AS vector encoding an artificial microRNA targeting huntingtin (Htt) resulted in 40-50% knockdown of Htt across multiple CNS structures in adult mice.

Materials and Methods

Generation of Packaging Constructs

AAV9.47 trans packaging plasmid was generated by replacing a portion of the AAV9 cap sequence in packaging plasmid pAR-9 with a de-novo synthesized fragment carrying the following mutations S414N, G453D, K557E and T582I (GenScript USA Inc., Piscataway, N.J.) (amino acid numbering beginning at VP1) using In-Fusion cloning kit (Clontech Laboratories Inc., Mountain View, Calif.). Packaging plasmid necessary to express either only VP1 and VP3 capsid proteins, or VP2 protein fused to peptide were generated by introducing point mutations (T138A substitution to generate VP1,3 plasmids; M1L for VP2 plasmids) as described for AAV2. Peptide and linker ($G_4S$) coding sequences were cloned at the N-terminus of VP2 using In-Fusion cloning kit to generate peptide-VP2 expression plasmids.

Vector Particle Production, Titer Quantification and Quality Analysis

The self-complementary AAV-CBA-GFP vector used in these studies carries an expression cassette comprised of the CBA promoter without an intron to drive expression of GFP and a rabbit β-globin poly-adenylation signal.

Sequences targeting mouse Htt mRNA were embedded into the artificial miR-155 scaffold to generate the following cassette: 5'-ctggaggcttgctgaaggctgtatgctgTTTAGACTTGT-GTCCTTGACCTgttttggccactgactgacTGG CAAAGCA-CAAGTCTAAAcaggacacaaggcctgttactagcactcacatg-gaacaaatggcc-3' (SEQ ID NO: 33; targeting sequence in bold uppercase). This artificial miRNA targets position 1090 in exon 8 of mouse huntingtin gene. eGFP and artificial miRNA cassette were expressed under the control of the cytomegalovirus enhancer/chicken β-actin promoter (CBA) containing the β-actin exon and chimeric intron.

To generate peptide-grafted AAV vectors, 293T cells were co-transfected with the following mix of plasmids using the calcium phosphate precipitation method: 7.96 μg transgene plasmid, 25.6 μg adenoviral helper plasmid pFΔ6, and a 5:1 ratio of VP1,3 packaging plasmid and peptide-VP2 packaging fused expression plasmid in trans, for a total amount of 12.2 μg, per $2.1 \times 10^7$ cells plated. 72 hours post transfection, cells were harvested and cell lysates prepared by 3 cycles of freeze-thaw and treated with Benzonase (Sigma-Aldrich, St. Louis, Mo.) (50 U/mL cell lysate, 37° C., 30 min). rAAV was purified from cell lysates by iodixanol density gradient ultracentrifugation (Optiprep density gradient medium, Axis-Shield, Oslo, Norway). Residual iodixanol was removed by replacing with Buffer B (20 mM TRIS, 0.5 M NaCl, pH 8.5) using a 100 kilodalton (kDa) cutoff centrifugation device (Amicon Ultra-15, Merck Millipore Ltd., Cork, Ireland) by three rounds of centrifugation at 1500×g and dialyzed twice using a 10,000 molecular weight cutoff (MWCO) dialysis cassette (Slide-A-Lyzer, Thermo Scientific, Rockford, Ill.) against a 1,000-fold volume of PBS for >2h and once overnight at 4° C. After treatment of stocks with DNase I (Roche Diagnostics GmbH, Mannheim, Germany, 2 U/μL vector, 37° C., 30 min), the titer of rAAV vectors was determined by real-time quantitative PCR (qPCR) using probe and primers specific for the rabbit β-globin polyA sequence (Integrated DNA Technologies, Coralville, Iowa). For stoichiometric analysis of capsid proteins, $1 \times 10^{10}$ vector particles of purified vector were subjected to Western blotting by standard SDS-PAGE technique. AAV capsid proteins were detected using mouse monoclonal anti-AAV capsid protein antibody clone B1 (1:500, American Research Products, Inc., Waltham, Mass., 03-65158), peroxidase linked anti-mouse secondary antibody (1:2000, GE Healthcare UK Ltd., Buckinghamshire, UK, 380199) and ECL Western Blotting Substrate (Pierce Protein Research Products, Rockford, Ill.).

Vector Administration and Tissue Processing rAAV vectors were administered via the tail vein in a volume of 200 μL into 6-8 week-old male C57BL/6J mice (Jackson Laboratory, Bar Harbor, Me.). A dose of $5 \times 10^{11}$ vg/mouse was administered for immunochemical studies and biodistribution analysis. For immunochemical and GFP fluorescence studies, mice were trans-cardially perfused at 4 weeks post-injection first with ice cold 1x phosphate buffer saline (PBS), followed by 10% phosphate-buffered formalin solution (Fisher Scientific, Fair Lawn, N.J.). Tissues were harvested and post-fixed in 10% phosphate-buffered formalin solution at 4° C. for an additional 24 h. Post-fixed tissues were transferred to 30% sucrose in 1×PBS for cryoprotection. Tissues were embedded in Tissue-Tek O.C.T. compound (Sakura Finetek, Torrance, Calif.) and frozen in a dry-ice-isopentane bath and stored at −80° C.

For biodistribution analysis, mice were trans-cardially perfused at 4 weeks post-infusion with ice-cold 1×PBS. Tissues were harvested immediately, frozen on dry ice and stored at −80° C.

Cat Studies rAAV vector was packaged by University of Massachusetts Medical School Viral Vector Core by transient transfection followed by purification by cesium chloride sedimentation, and administered through the carotid artery into a 2 month old normal domestic short haired cat at a dose of $1.29 \times 10^{13}$ vg. At 4 weeks post infusion, the injected cat was trans-cardially perfused with cold 1×PBS. Various tissues were harvested and fixed in 4% paraformaldehyde in PBS at 4° C. The brain was cut into 0.6 cm coronal blocks prior to immersion in fixative. Processing of post-fixed brains and spinal cords for immunohistochemical (IHC) and immunofluorescence studies was identical to that for mouse studies.
Immunohistochemical Detection of GFP Expression For chromogenic IHC, 40 μm serial sections of brains and 30 μm serial sections of spinal cord were incubated for 96 h in anti-GFP primary antibody (ABfinity rabbit monoclonal anti-GFP 1:1000, G10362, Life Technologies, Grand Island, N.Y.) at 4° C. After washing with 1×PBS, sections were incubated in appropriate biotinylated secondary antibody (biotinylated anti-rabbit antibody, Vector Laboratories Inc., Burlingame, Calif.), followed by incubation in ABC reagent (PK-6100, Vector Laboratories Inc.). Sections were developed with 3,3'-diaminobenzidine reagent (DAB) according to the manufacturer's instructions (SK-4100, Vector Laboratories Inc.), dehydrated with increasing concentrations of ethanol, cleared with xylene and mounted using Permount mounting medium (Fisher Scientific).

For immunofluorescence studies, 40 μm sections of brains and 30 μm sections of spinal cord were incubated for 24 h in a cocktail of appropriate primary antibodies at 4° C. The primary antibodies used were: rabbit polyclonal anti-GFP (1:1000, Life Technologies, A11122), mouse monoclonal anti-NeuN (1:500, EMD Millipore, MAB377), mouse monoclonal anti-DARPP32 (1:250, BD Biosciences, 611520). After washing in 1×PBS, sections were incubated for 1 h at room temperature in appropriate secondary antibodies, washed in 1×PBS and mounted using Permafluor mounting media (Thermo Scientific). Native GFP fluorescence in liver and skeletal muscle (quadriceps) was analyzed in 30 μm sections mounted using Permafluor mounting media. All images were captured on a Leica DM5500 B microscope (Leica Microsystems Inc., Buffalo Grove, Ill.). Post-processing of images was performed using Adobe Photoshop CS6 (Adobe Systems, San Jose, Calif.).
Quantification of GFP-Positive Neurons in Striatum and Thalamus Chromogenic IHC staining of 40 μm mouse brain sections was performed. Five 663.28 μm×497.40 μm regions were randomly chosen from the striatum or thalamus (n=4 biological replicates per vector) of the stained sections. Neurons were identified by their morphology and counted by individuals blinded to the study design. All statistical analyses were performed using GraphPad Prism (GraphPad Software, Inc., La Jolla, Calif.). Total neurons in the 663.28 μm×497.40 μm fields were counted in Nissl (cresyl violet acetate) stained brain sections using ImageJ software. Significance was determined by Student's unpaired T-test. A p<0.05 was considered to be significant.
Biodistribution Analysis Vector genome copy numbers from various mouse tissues were determined by qPCR after extraction of total DNA using DNeasy Blood and Tissue kit (Qiagen). Tissues were mechanically lysed using TissueLyzer II (Qiagen GmbH, Hilden, Germany). Vector genome content in each tissue was determined using 100 ng total DNA using the same qPCR method described above for AAV vector titration. All statistical analyses were performed using GraphPad Prism. Significance was determined by Student's unpaired T-test. A p<0.05 was considered to be significant.

Western blotting to detect GFP protein levels in various tissue types was performed using primary antibodies detecting GFP (chicken polyclonal anti-GFP, 1:2000, Aves Labs Inc., Tigard, Oreg., GFP-1010) and mouse β-actin (mouse monoclonal anti-β-actin, 1:1000, Sigma-Aldrich, St. Louis, Mo., A5441), followed by appropriate IRDye secondary antibodies (LI-COR Inc., Lincoln, Nebr.). Total protein was isolated from harvested tissues by bead lysis in T-PER tissue extraction reagent (Life Technologies) and quantified by Bradford assay. 20 g of total protein was loaded onto each well of 4-20% Mini-PROTEAN TGX gels (Bio-Rad Laboratories Inc., Hercules, Calif.). Tissues from two representative mice per group were used for analysis. Detection and quantification were done with Odyssey infrared imaging system (LI-COR Inc.).
In-vitro Binding Assay Pro5 and Lec2 CHO cell lines were gifts from Dr. Aravind Asokan (University of North Carolina Chapel Hill) and binding assay was performed as previously described. Briefly, cells were pre-chilled for 30 min at 4° C. in serum-free DMEM (Life Technologies), followed by incubation with rAAV vectors at $4\times10^4$ vg/cell in cold serum-free media DMEM at 4° C. 90 min later, cells were washed thrice with cold serum-free DMEM to remove loosely bound vector particles. Cells were harvested and total DNA was extracted using DNeasy Blood and Tissue kit (Qiagen). Vector genome copy numbers of cell surface bound virions was quantified by qPCR.
Analysis of Htt Knockdown rAAV vectors were administered intravascularly via the tail vein into 6-8 week-old male C57BL/6J mice (Jackson Laboratory, Bar Harbor, Me.) at a dose of $9.4\times10^{11}$ vg/mouse. Mice were euthanized at 4 weeks post-injection and the brain sectioned in 2 mm coronal blocks using a brain matrix. Biopsy punches of different diameters (2 or 3 mm) were used to sample motor cortex (2 mm), striatum (3 mm) and thalamus (3 mm). Cervical spinal cord and liver were also included in the analysis. Tissue samples were mechanically homogenized using a TissueLyzer II and 5 mm stainless steel beads (Qiagen) in Trizol (Life Technologies). Total RNA was isolated using Direct-zol RNA MiniPrep kit (Zymo Research Corporation, Irvine, Calif.) according to manufacturer's protocol. Total RNA (400-1000 ng) was reverse transcribed using High Capacity RNA to cDNA kit (Applied Biosystems, Foster City, Calif.). Relative mouse Htt mRNA expression was assessed by qPCR using TaqMan gene expression assays for mouse Htt (Mm01213820_m1, Applied Biosystems) and hypoxanthine phosphoribosyltransferase 1 (Hprt1; mm00446968_m1, Applied Biosystems). Changes in Htt mRNA for groups injected with AAV9 or AAV-AS vectors were calculated relative to PBS-injected mice using the $2^{-\Delta\Delta CT}$ method. Significance was determined by Student's unpaired T-test. A p<0.05 was considered to be significant.

For protein analysis, a frozen punch from each region (motor cortex, striatum, thalamus, cervical spinal cord, and liver) was homogenized in 75-300 μl 10 mM HEPES pH7.4, 250 mM sucrose, 1 mM EDTA+protease inhibitor tablet (cOmplete mini, EDTA-free, Roche), 1 mM NaF and 1 mM $Na_3VO_4$ on ice for 30 strokes. Protein concentration was determined by Bradford method (BioRad) and 10g motor cortex, striatum, and thalamus or 20 μg cervical spinal cord and liver were loaded onto 3-8% Tris-Acetate gels (Life Technologies) and separated by SDS-PAGE. Proteins were transferred to nitrocellulose using a TransBlot Turbo apparatus (BioRad) then blots were cut horizontally at 72 kD. Blots were washed in TRIS-buffered saline+0.1% Tween 20 (TBST) and blocked in 5% milk/TBST. The top half of the blot was incubated in anti-Htt antibody Ab1 (1:2000) and the bottom half in anti-tubulin antibody (1:4000, Sigma) or anti-GAPDH antibody (1:6000, Millipore) diluted in 5% milk/TBST overnight at 4° C. Blots were washed in TBST then incubated in peroxidase conjugated secondary antibodies diluted in 5% milk/TBST for 1 hour at room temperature, washed, and proteins were detected using SuperSignal West Pico Chemiluminescent Substrate (Thermo Scientific) and FluoroChem SP (Alpha Innotech) and Hyperfilm ECL. The bottom blots were reprobed with anti-GFP antibody (1:3000, Cell Signaling). Densitometry was performed using ImageJ software.

Figure 8A:
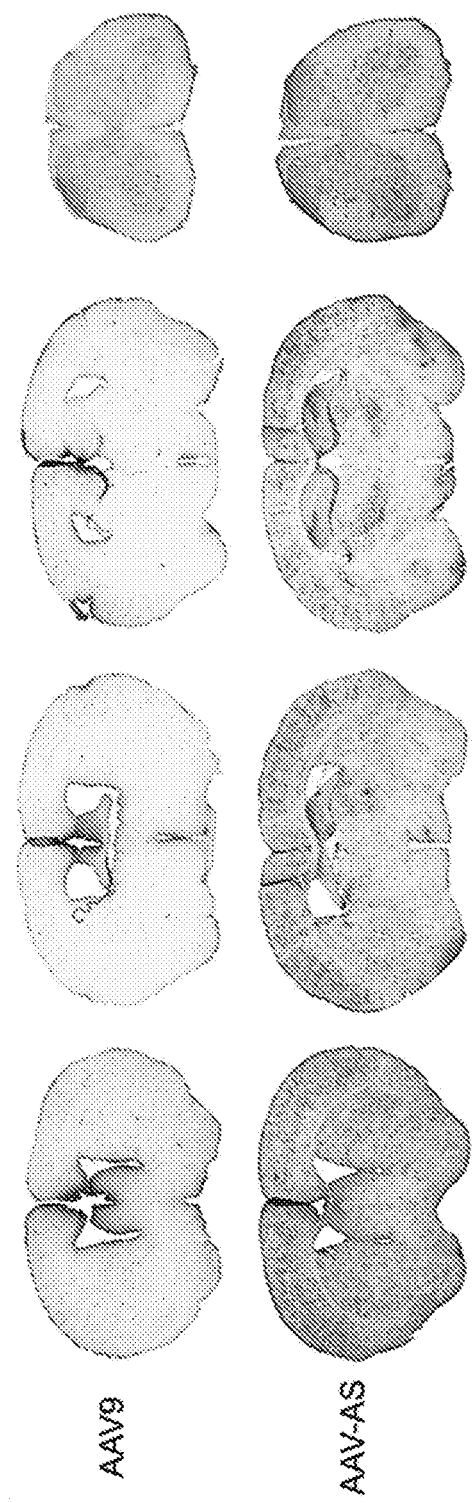
FIGS. 8A-8C show CNS transduction profile of AAV-AS vector after vascular infusion in adult mice.
Figure 8B:
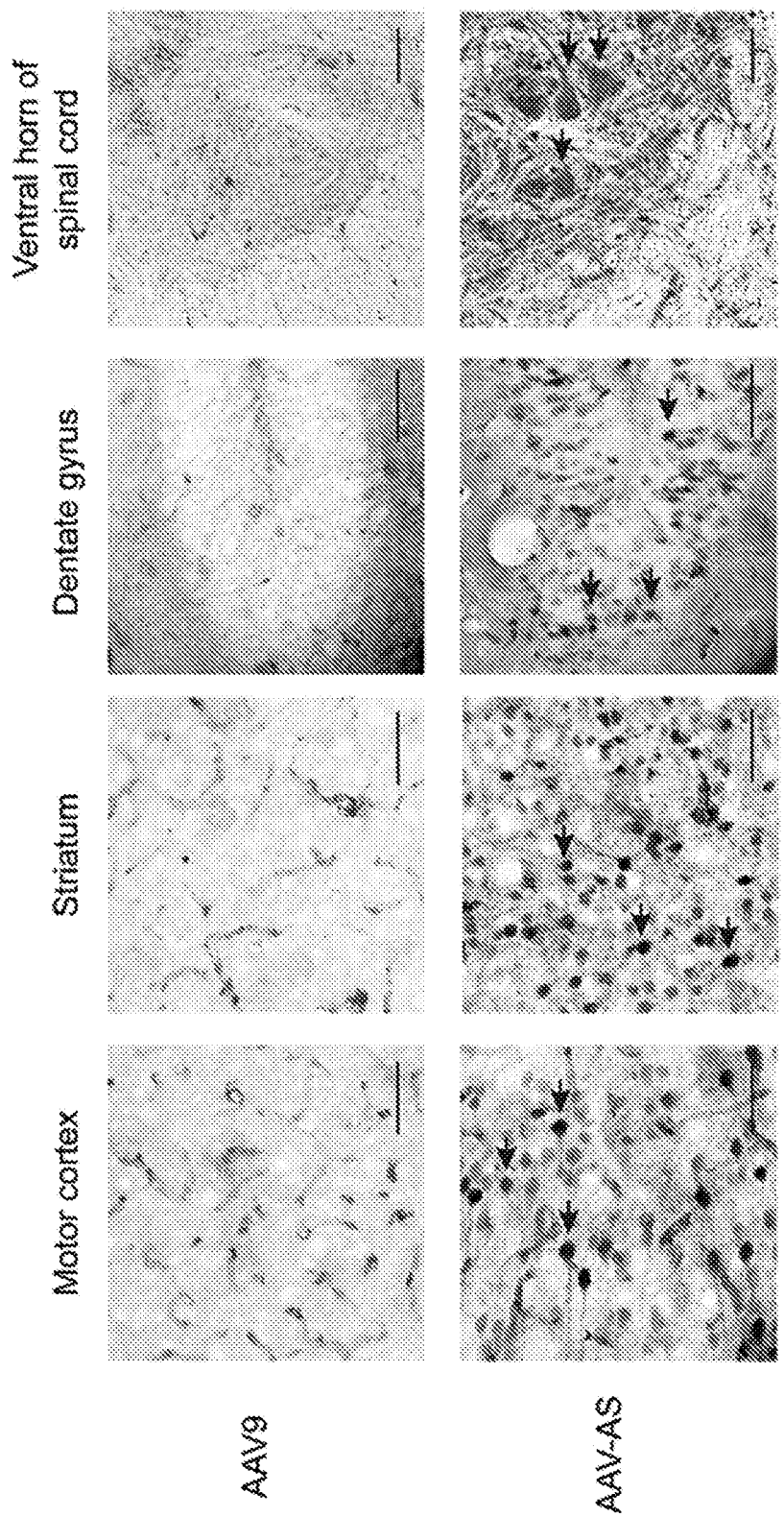
Figure 8C:
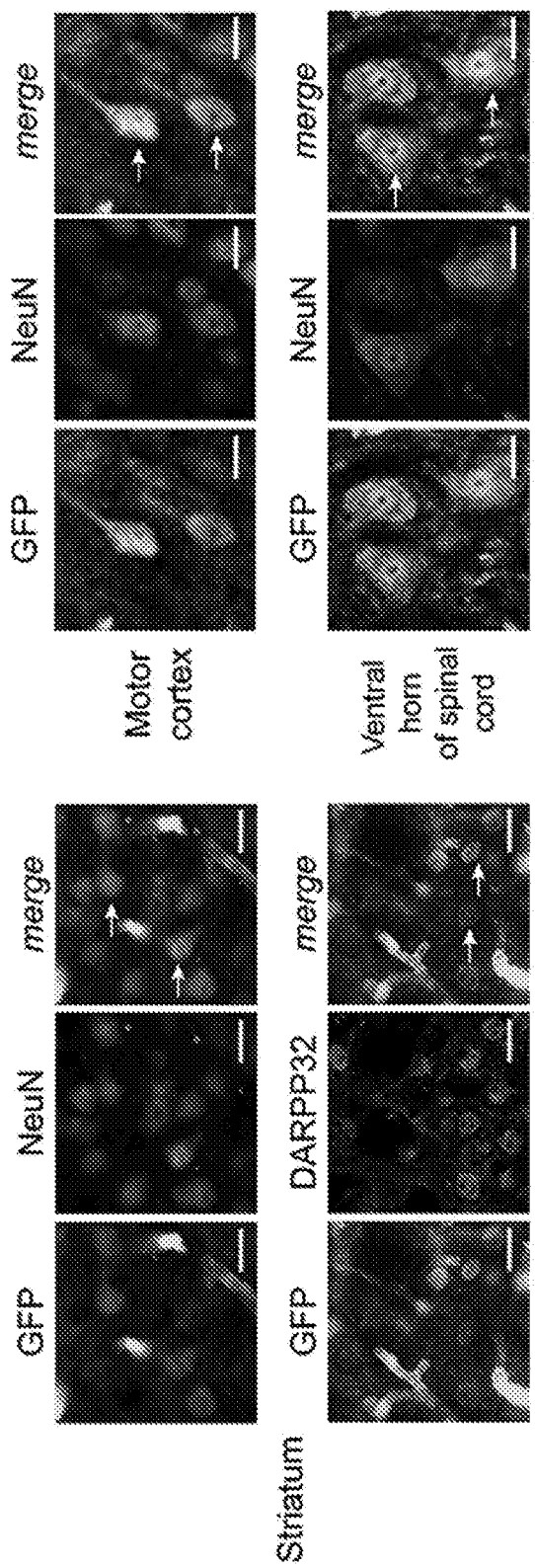
Figure 12A:
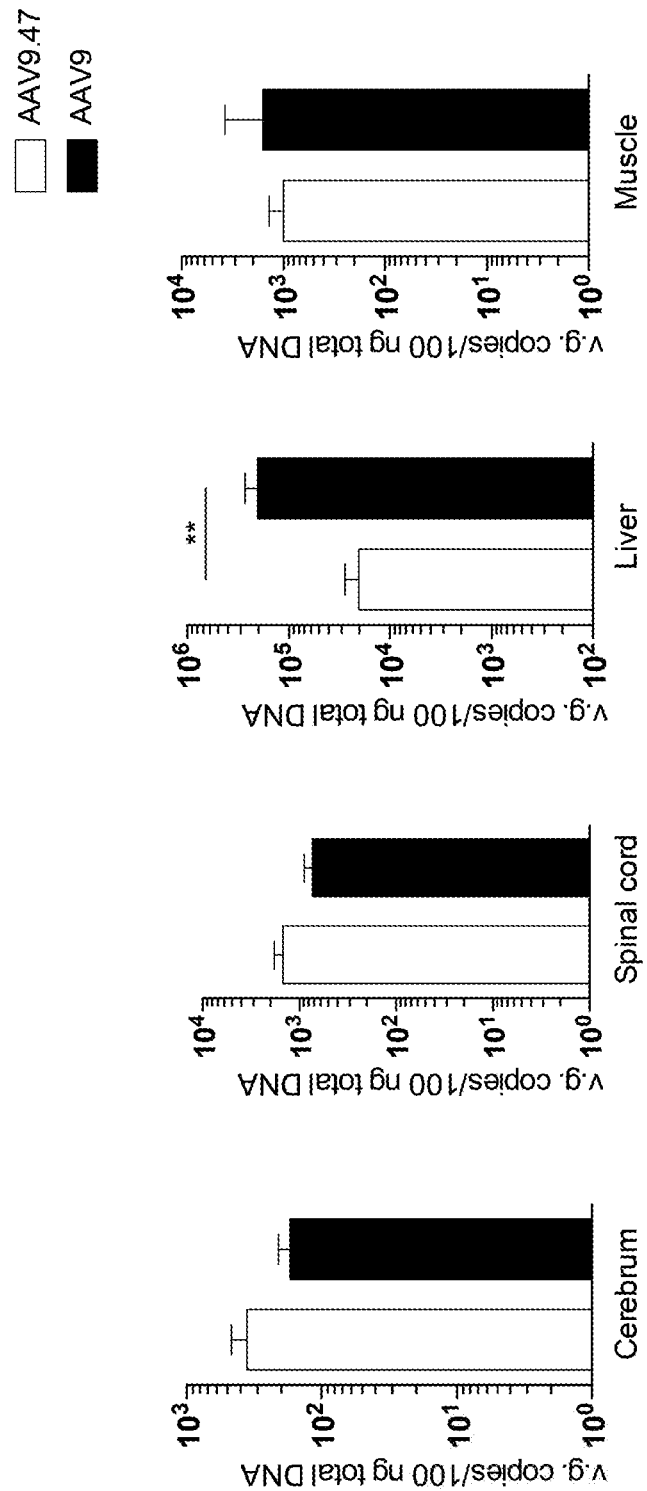
FIGS. 12A-12B show the biodistribution profile of AAV9.47.
Figure 12B:
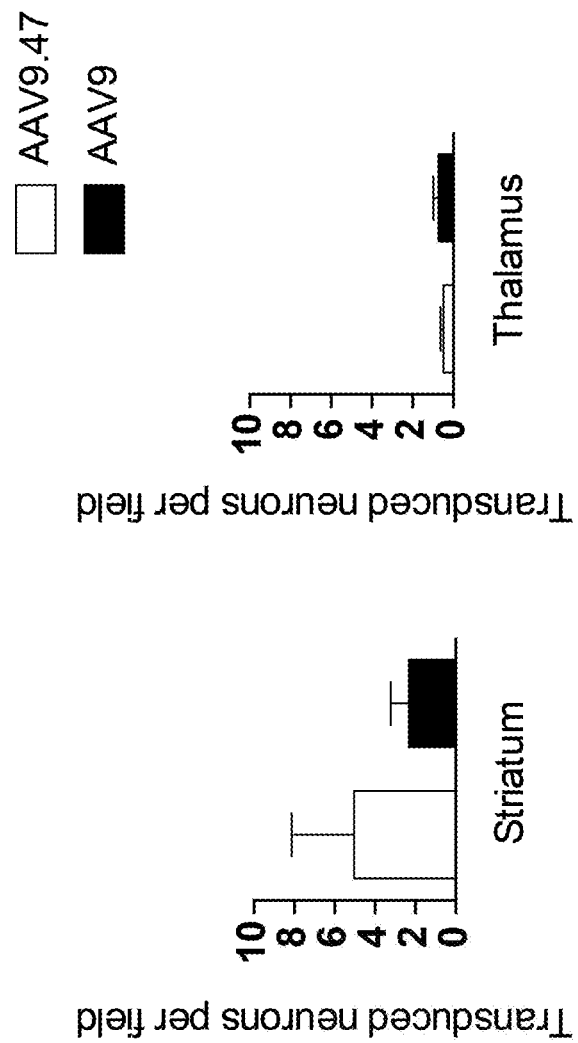
Figure 13A:
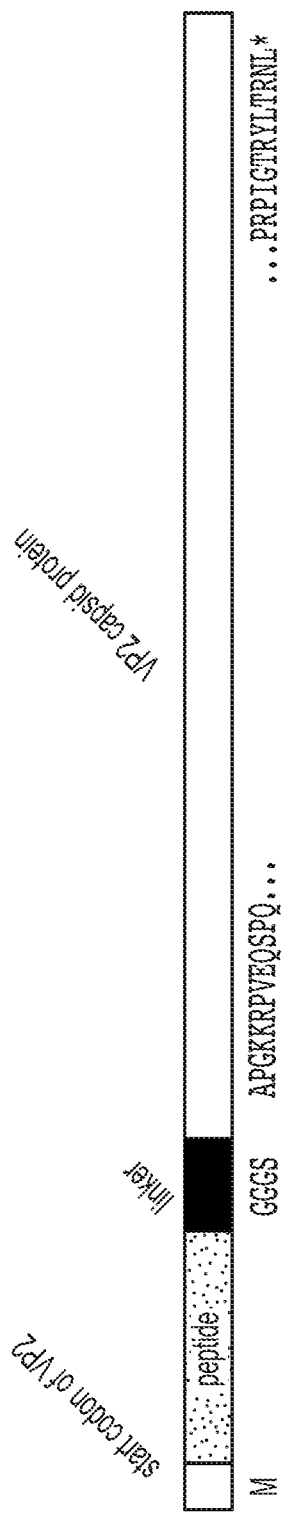
FIGS. 13A-13B show construction of peptide-inserted vectors.
Figure 13B:
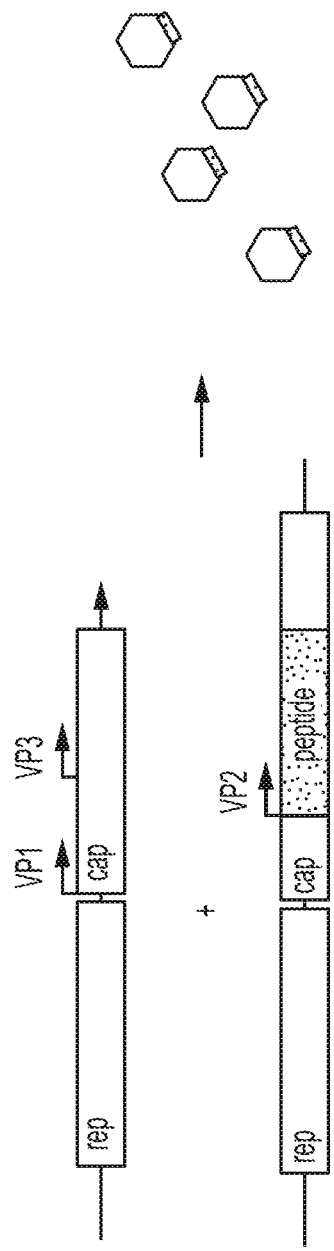
Figure 14:
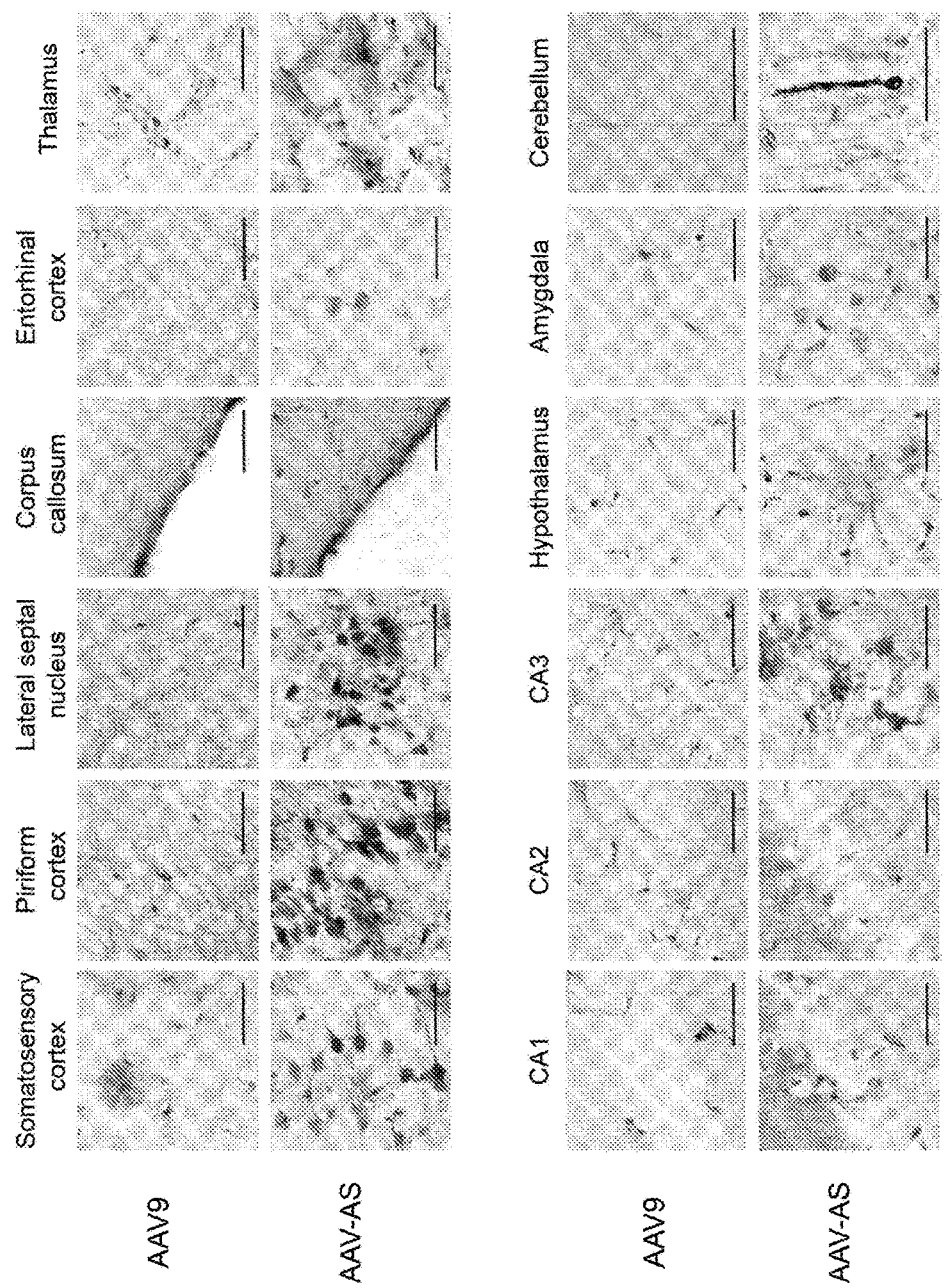
FIG. 14 shows transduction profile of AAV-AS and AAV9 vectors across multiple CNS regions after systemic delivery. Bar=50 µm.

Insertion of Poly-alanine Peptide in AAV9.47 Capsid Enhances Neuronal Gene Transfer in Adult Mice AAV9.47 was selected as the capsid in which to test the peptide grafting approach, as this quadruple mutant of AAV9 (S414N, G453D, K557E, T582I) has comparable CNS gene transfer properties to AAV9 but decreased tropism to liver (FIG. 12). Peptides were grafted on the AAV9.47 capsid surface via genetic fusion to the N-terminus of VP2 (FIG. 13). A peptide-modified AAV9.47 vector carrying a string of 19 alanines in the VP2 capsid protein, designated as AAV-AS, showed a remarkable increase in CNS transduction efficiency compared to AAV9 (FIG. 8A) after systemic delivery in 6-8 week old C57BL/6 mice (FIG. 8A). AAV-AS vector transduced diverse neuronal populations, glia and endothelia throughout the brain and spinal cord, including extensive transduction of neurons in motor cortex and striatum (FIG. 8B). Efficient transduction of granule cells in the dentate gyrus, as well as motor neurons and interneurons in the spinal cord, was observed (FIG. 8B). The identity of GFP-positive cells with neuronal morphology in cortex, striatum and spinal cord was confirmed by co-localization of GFP and NeuN (FIG. 8C). GFP-positive neurons in the striatum were shown to be DARPP32-positive medium spiny neurons (FIG. 8C). Neuronal transduction was apparent in many brain regions of AAV-AS injected mice with the exception of thalamus and hypothalamus where only sparse transduction was observed (FIG. 14). AAV-AS also transduced oligodendrocytes in the corpus callosum and Bergmann glia in the cerebellum (FIG. 14). The transduction profile of AAV9 was limited to glial cells and endothelia in most CNS regions analyzed (FIG. 8B and FIG. 14).

Figure 9A:
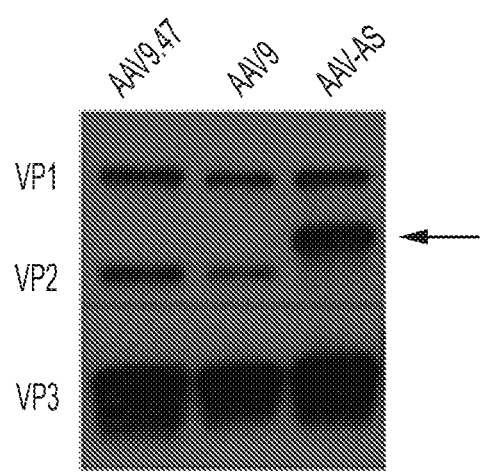
FIGS. 9A-9F show quantitative assessment of AAV-AS CNS transduction efficacy.
Figure 9B:
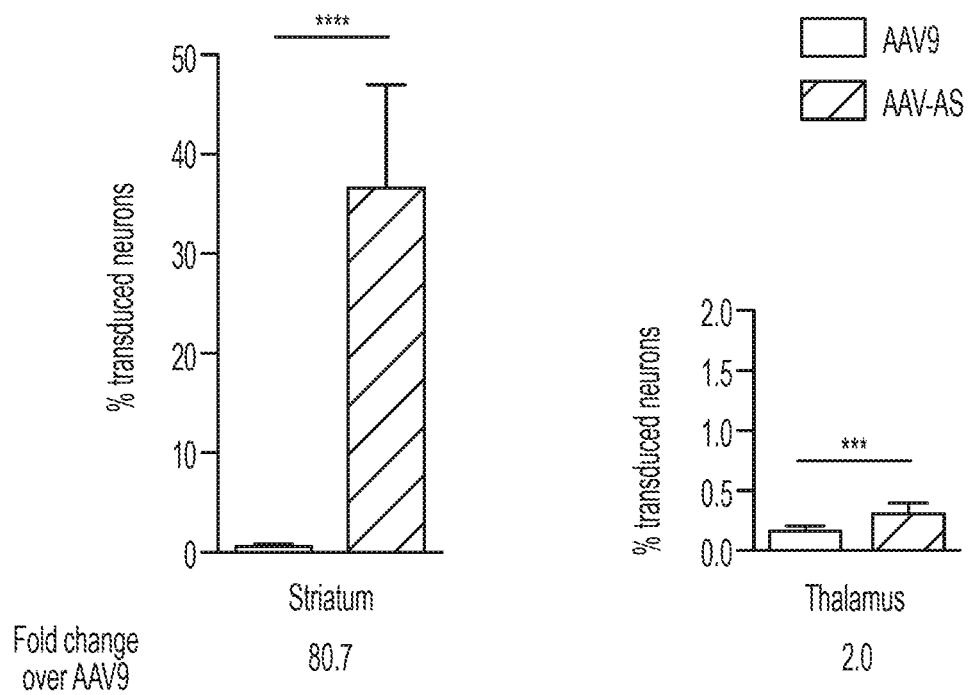
Figure 9C:
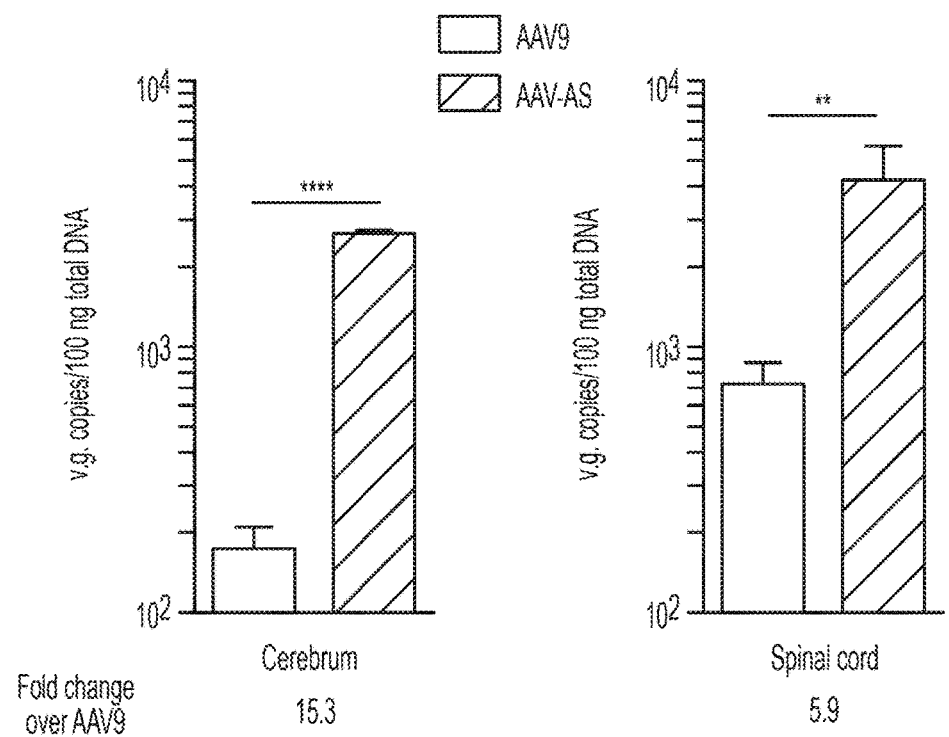
Figure 9D:
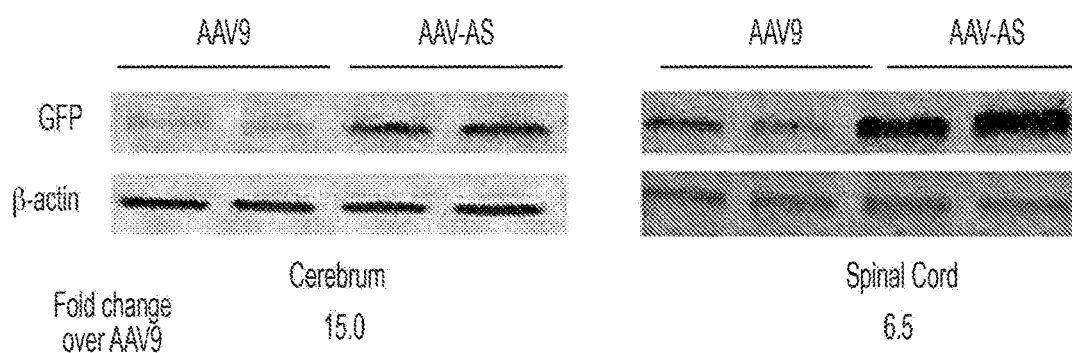
Figure 9E:
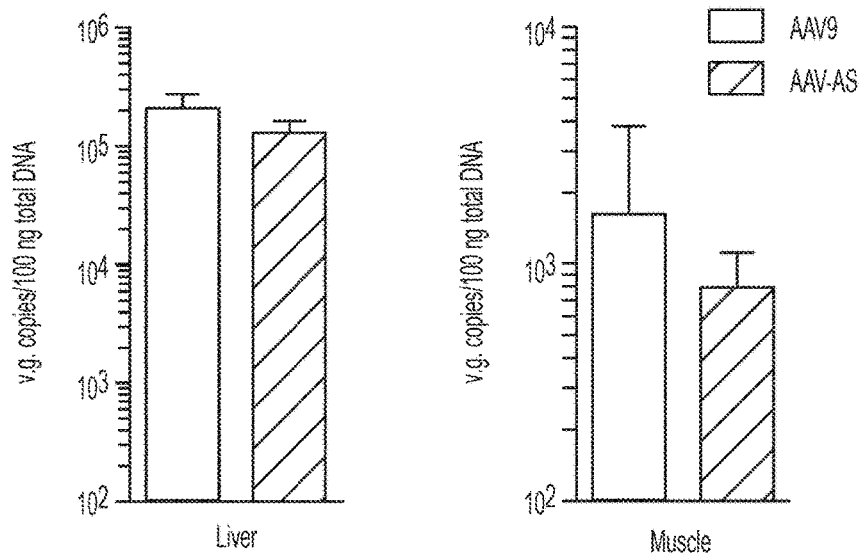
Figure 9F:
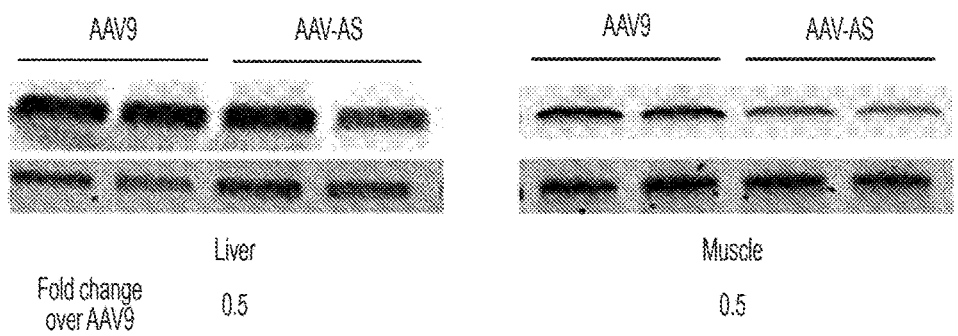

Western blot analysis of AAV preparations confirmed incorporation of the chimeric poly-alanine VP2 protein in the AAV-AS capsid (FIG. 9A). Quantification of GFP-positive neurons in thalamus and striatum revealed a modest 2-fold increase in transduced thalamic neurons but a striking 80-fold increase in transduced striatal neurons for AAV-AS compared to AAV9 (FIG. 9B). AAV-AS transduced as many as 36% of striatal neurons compared to only 0.45% by AAV9 (FIG. 9B). The CNS transduction efficiency of AAV-AS vector was also reflected in its biodistribution profile. More vector genomes were found in the cerebrum and spinal cord of AAV-AS injected animals compared to AAV9 (15-fold and 6-fold, respectively) (FIG. 9C). These findings were corroborated by comparable increase in GFP protein in cerebrum and spinal cord (FIG. 9D). The increased gene transfer efficiency for AAV-AS vector compared to AAV9 appears to be restricted to CNS, as transduction of liver and muscle was identical for both AAV vectors based on analysis of vector genome content (FIG. 9E) and GFP protein levels (FIG. 9F).

Figure 15:
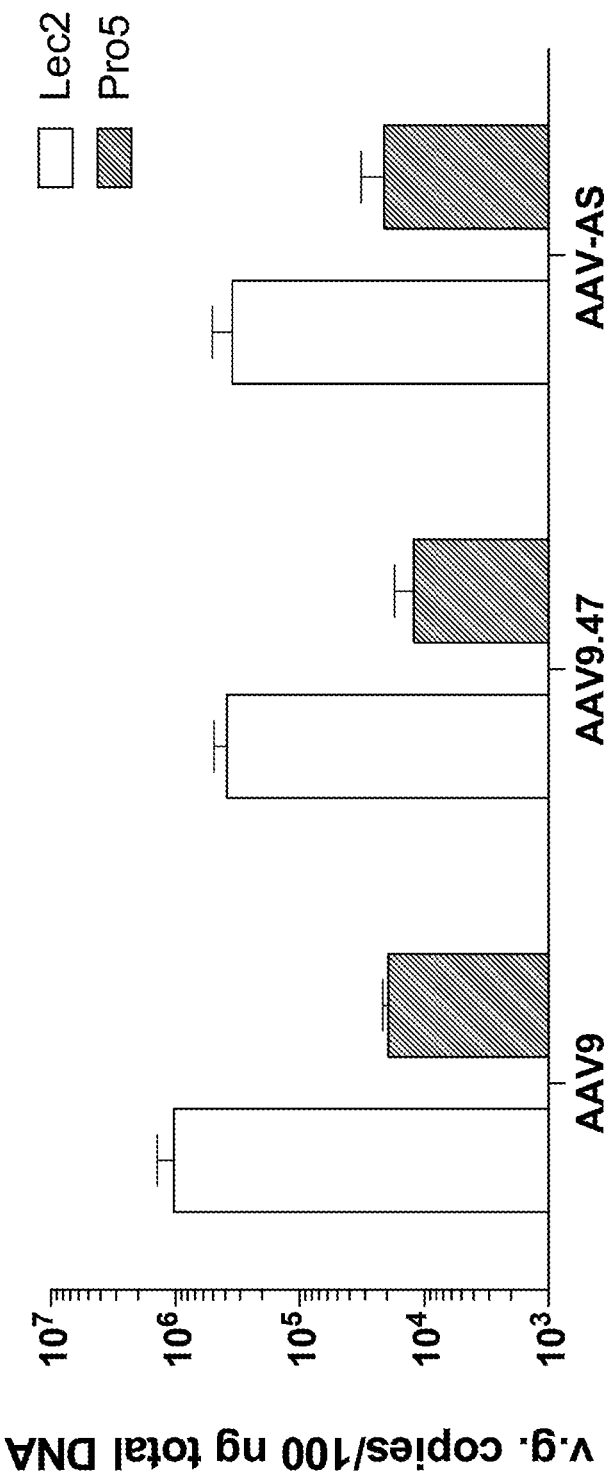
FIG. 15 shows cell binding studies of native and peptide-modified AAV vector. No significant difference in binding to Lec2 or Pro5 cells. Data shown as mean±SD. Experiment was performed with N=3 biological replicates.
Figure 16A:
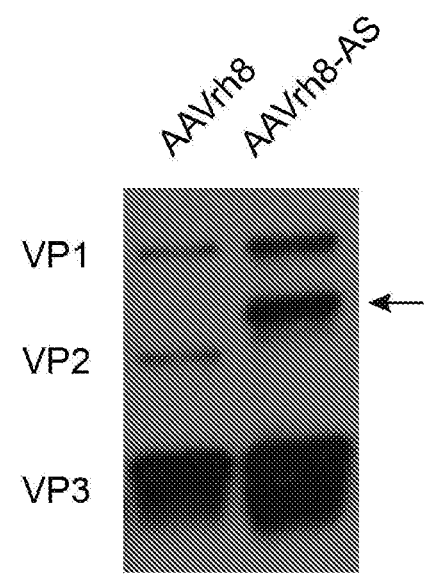
FIGS. 16A-16C show the brain transduction profile of AAVrh8-AS vector. Distribution of GFP positive cells was assess in immunostained histological sections.
Figure 16B:
Figure 16C:
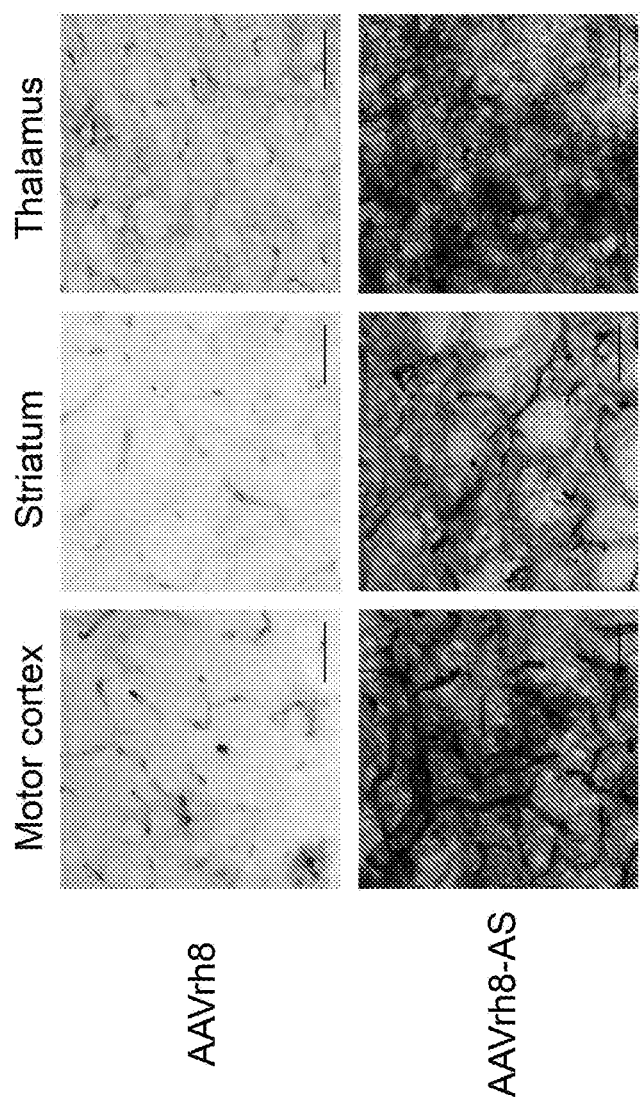
Figure 17A:
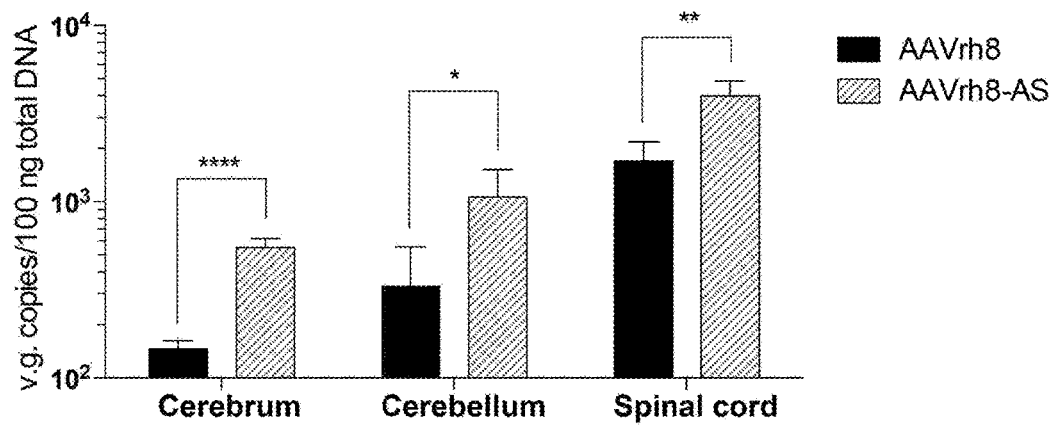
FIGS. 17A-17B show biodistribution of AAVrh8-AS and AAVrh8 vectors. Quantification of AAV vector genome content in (FIG. 17A) different CNS regions or (FIG. 17B) liver. Data shown as mean±SD. Experiment was performed with N=3 per group. *p<0.05, p<0.01, **p<0.0001 by Student's unpaired t-test.
Figure 17B:
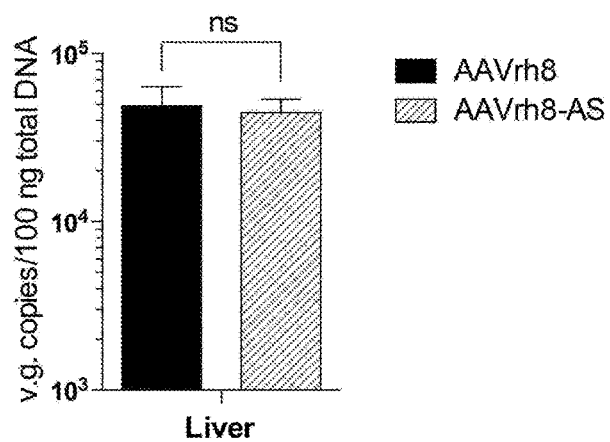

As a first step to understand how the poly-alanine peptide enhances CNS transduction of AAV9.47, a cell culture study was carried out to determine whether it changes the capsid interaction with exposed galactose residues on cell surface glycans. Terminal N-linked galactose is the primary cell surface receptor for AAV9. Binding studies in parental (Pro5) and sialic acid-deficient (Lec2) CHO cells showed no differences between AAV-AS, AAV9.47 and AAV9 vectors (FIG. 15).

Figure 10A:
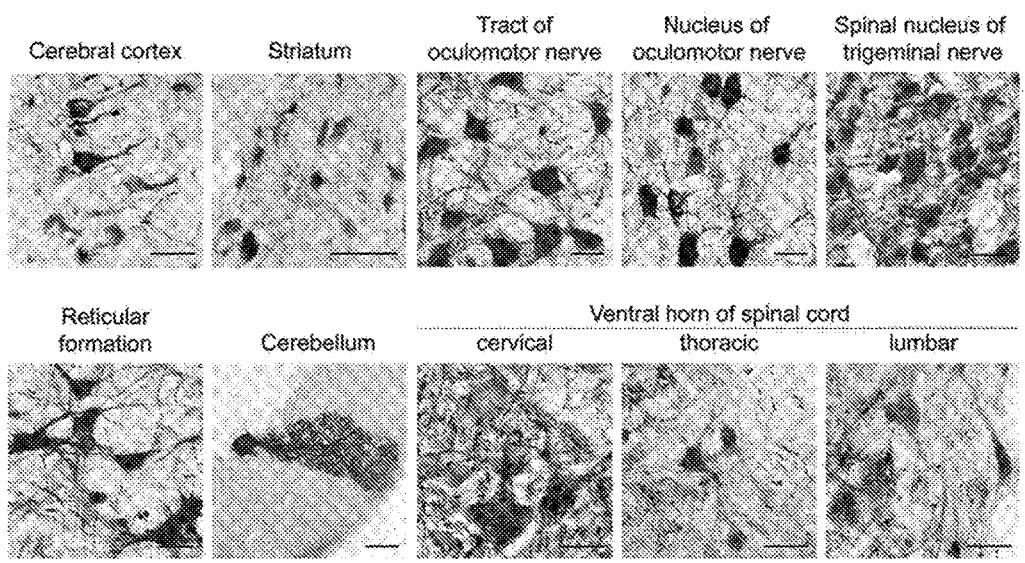
FIGS. 10A-10B show neuronal transduction in cat after systemic delivery of AAV-AS vectors.
Figure 10B:
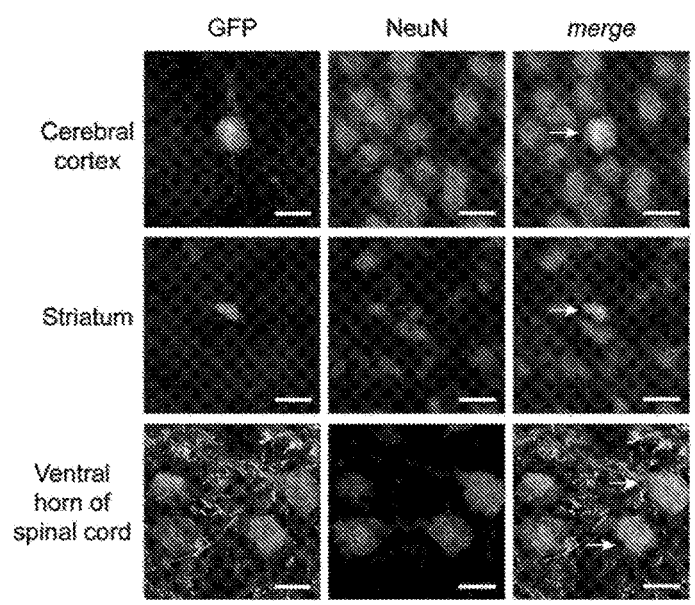

AAV-AS Transduces Neurons Throughout the Cat Brain after Systemic Administration Next, whether the neuronal transduction properties of AAV-AS are reproducible in cats was assessed. Consistent with results in mice, AAV-AS transduced diverse neuronal populations across the cat brain and spinal cord, including neurons in cerebral cortex, striatum and reticular formation, Purkinje neurons in cerebellum and motor neurons in the oculomotor nucleus located in ventral midbrain, spinal nucleus of the trigeminal nerve in brainstem and throughout the spinal cord (FIG. 10A-10B). Curiously, no endothelial and only sparse glial transduction was apparent in the cat brain in this study.

Widespread Knockdown of Htt in CNS after Systemic Delivery of AAV-AS Vector

Figure 11A:
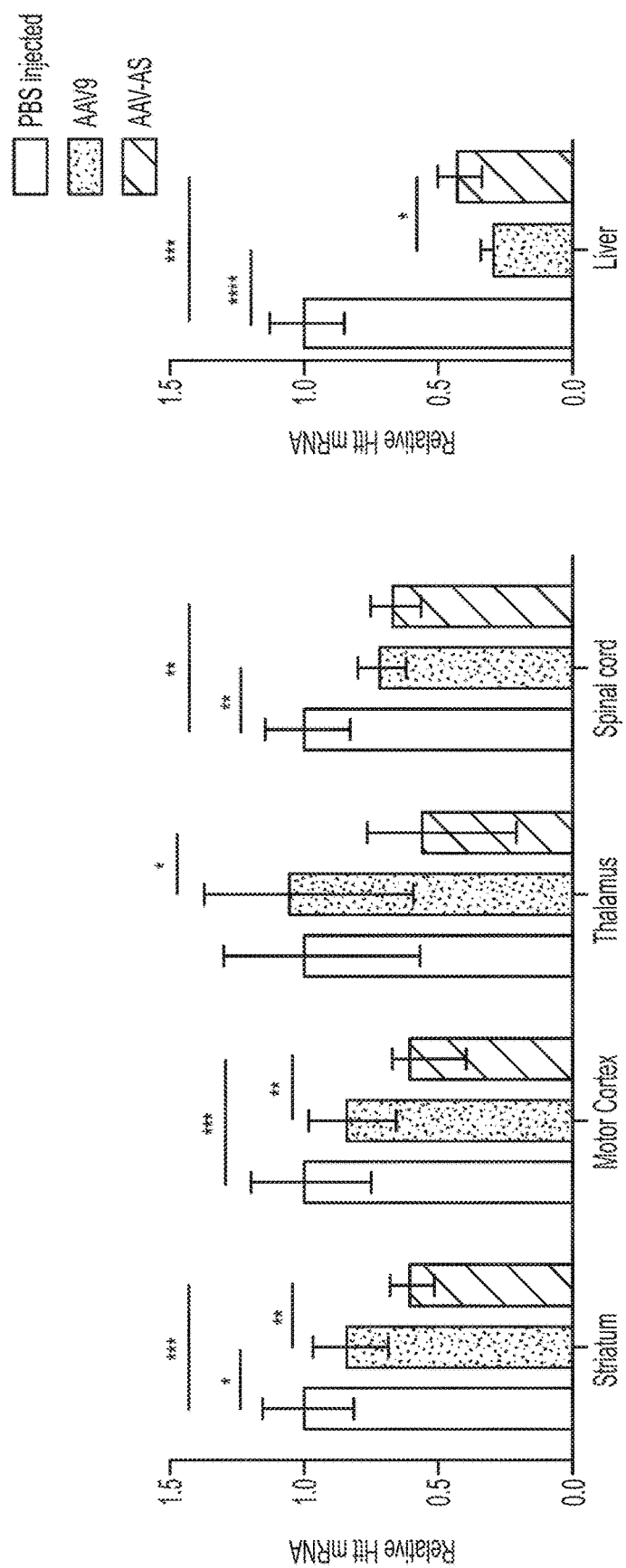
FIGS. 11A-11B show Htt knockdown in mice upon intravenous administration of AAV-AS-miR$^{Htt}$ vector.
Figure 11B:
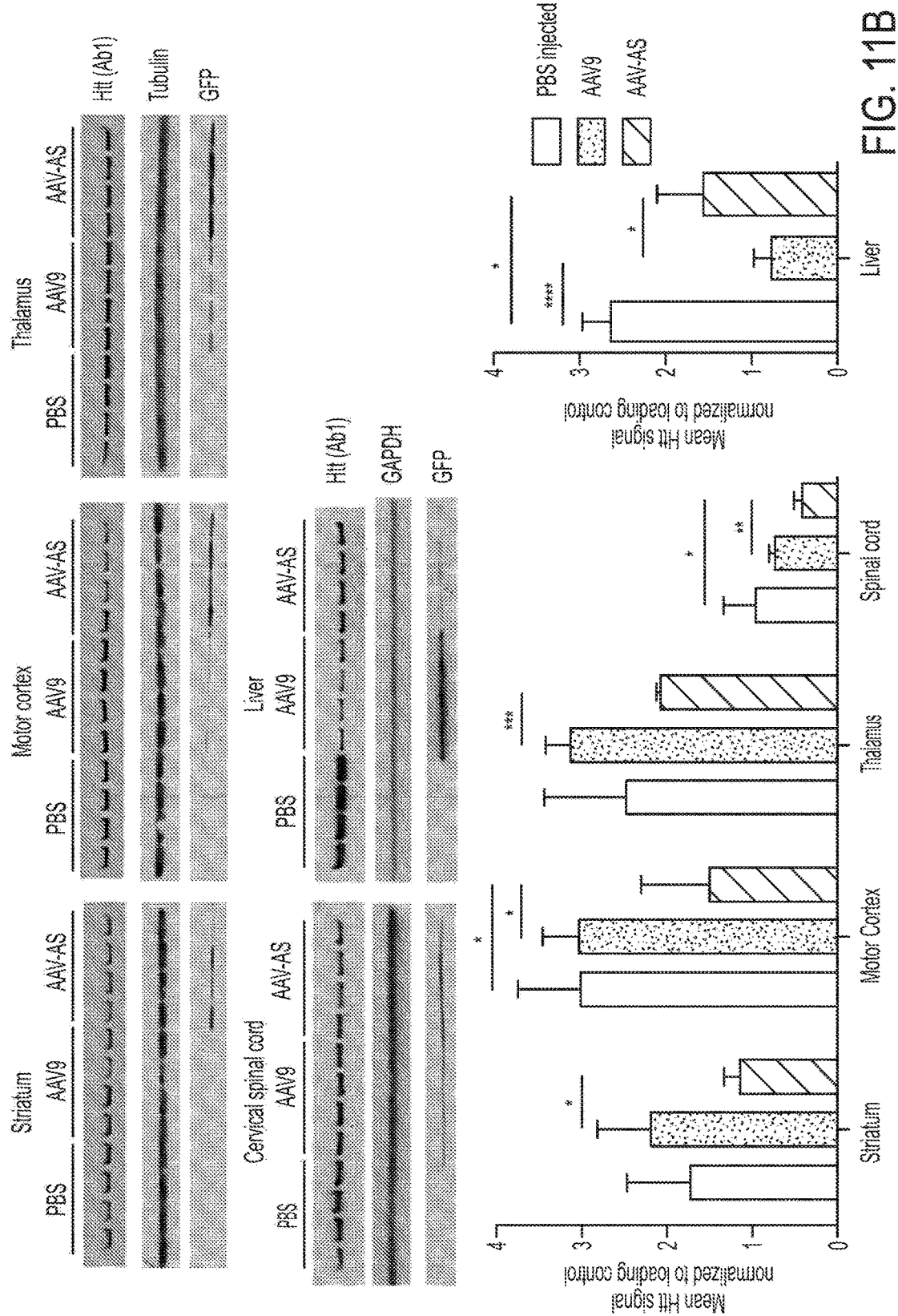

The therapeutic potential of AAV-AS vector for Huntington's disease was examined. AAV-AS and AAV9 vectors encoding GFP and an U6-driven artificial microRNA specific for mouse Htt ($miR^{Htt}$) were infused systemically in C57BL/6 mice. Huntingtin mRNA and protein levels in CNS and liver were assessed at 4 weeks post injection (FIG. 11). AAV-AS vector resulted in 40-50% reduction in Htt mRNA in striatum, motor cortex and spinal cord, and was better than AAV9 in all brain regions, but comparable in the spinal cord (FIG. 11A). Conversely, AAV-AS was less potent than AAV9 in lowering Htt mRNA in liver (FIG. 11A). Western blot analysis of Htt protein levels corroborated the differences between AAV9 and AAV-AS in the striatum, motor cortex and thalamus as well as in liver (FIG. 11B). The reduction in Htt protein levels was inversely proportional to GFP protein levels, which indicates that higher CNS transduction efficiency leads to greater reduction in huntingtin mRNA and protein.

This disclosure is not limited in its application to the details of construction and the arrangement of components set forth in this description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:

1. An adeno associated virus capsid protein comprising an N-terminally grafted heterologous targeting peptide, wherein:
   (i) the capsid protein is a VP2 capsid protein that is not of an AAV2 serotype; and
   (ii) the targeting peptide is a CNS-targeting polypeptide consisting of the amino acid sequence set forth in SEQ ID NO: 5, that is inserted between the first and second amino acid residues of the VP2 capsid protein.

2. The capsid protein of claim 1, further comprising a linker conjugated to the C-terminus of the N-terminally grafted heterologous targeting peptide.

3. The capsid protein of claim 2, wherein the linker comprises at least one polypeptide repeat, each repeat comprising at least two glycine residues.

4. The capsid protein of claim 3, wherein the linker is of the formula [G]$_n$S, wherein n is an integer in a range of 2 to 10.

5. The capsid protein of claim 3, wherein the linker comprises the formula [GGGGS]$_n$, wherein n is an integer in a range of 1 to 4.

6. The capsid protein of claim 5, wherein the linker comprises SEQ ID NO: 28.

7. An adeno associated virus capsid protein comprising an N-terminally grafted heterologous targeting peptide, wherein:
   (i) the capsid protein is a VP2 capsid protein that is not of an AAV2 serotype; and
   (ii) the targeting peptide is a CNS-targeting polypeptide consisting of the amino acid sequence set forth in SEQ ID NO: 7, that is inserted between the first and second amino acid residues of the VP2 capsid protein.

8. The capsid protein of claim 7, further comprising a linker conjugated to the C-terminus of the N-terminally grafted heterologous targeting peptide.

9. The capsid protein of claim 8, wherein the linker comprises at least one polypeptide repeat, each repeat comprising at least two glycine residues.

10. The capsid protein of claim 9, wherein the linker is of the formula [G]$_n$S, wherein n is an integer in a range of 2 to 10.

11. The capsid protein of claim 9, wherein the linker comprises the formula [GGGGS]$_n$, wherein n is an integer in a range of 1 to 4.

12. The capsid protein of claim 11, wherein the linker comprises SEQ ID NO:28.

13. An adeno associated virus capsid protein comprising an N-terminally grafted heterologous targeting peptide, wherein:
   (i) the capsid protein is a VP2 capsid protein that is not of an AAV2 serotype; and
   (ii) the targeting peptide is a CNS-targeting polypeptide encoded by a nucleic acid consisting of the nucleotide sequence set forth in SEQ ID NO: 29, that is inserted between the first and second amino acid residues of the VP2 capsid protein.

14. The capsid protein of claim 13, further comprising a linker conjugated to the C-terminus of the N-terminally grafted heterologous targeting peptide.

15. The capsid protein of claim 14, wherein the linker comprises at least one polypeptide repeat, each repeat comprising at least two glycine residues.

16. The capsid protein of claim 15, wherein the linker is of the formula $[G]_nS$, wherein n is an integer in a range of 2 to 10.

17. The capsid protein of claim 15, wherein the linker comprises the formula $[GGGGS]_n$, wherein n is an integer in a range of 1 to 4.

18. The capsid protein of claim 17, wherein the linker comprises SEQ ID NO:28.

* * * * *

SEQUENCE LISTING

<160> NUMBER OF SEQ ID NOS: 33

<210> SEQ ID NO 1
<211> LENGTH: 122

```
<212> TYPE: PRT
<213> ORGANISM: Artificial Sequence
<220> FEATURE:
<223> OTHER INFORMATION: Synthetic Polypeptide

<400> SEQUENCE: 1

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
            85                  90                  95

Ala Ala Gly Ser Thr Ser Thr Ala Thr Pro Leu Arg Val Asp Tyr Trp
        100                 105                 110

Gly Lys Gly Thr Gln Val Thr Val Ser Ser
        115                 120

<210> SEQ ID NO 2
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 2

Glu Val Gln Leu Gln Ala Ser Gly Gly Gly Leu Val Gln Ala Gly Gly
1               5                   10                  15

Ser Leu Arg Leu Ser Cys Ser Ala Ser Val Arg Thr Phe Ser Ile Tyr
            20                  25                  30

Ala Met Gly Trp Phe Arg Gln Ala Pro Gly Lys Glu Arg Glu Phe Val
        35                  40                  45

Ala Gly Ile Asn Arg Ser Gly Asp Val Thr Lys Tyr Ala Asp Phe Val
50                  55                  60

Lys Gly Arg Phe Ser Ile Ser Arg Asp Asn Ala Lys Asn Met Val Tyr
65                  70                  75                  80

Leu Gln Met Asn Ser Leu Lys Pro Glu Asp Thr Ala Leu Tyr Tyr Cys
            85                  90                  95

Ala Ala Thr Trp Ala Tyr Asp Thr Val Gly Ala Leu Thr Ser Gly Tyr
        100                 105                 110

Asn Phe Trp Gly Gln Gly Thr Gln Val Thr Val Ser Ser
        115                 120                 125

<210> SEQ ID NO 3
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 3

Pro Ser Ser Val Ile Asp Ala Leu Gln Tyr Lys Leu Glu Gly Thr Thr
1               5                   10                  15

Arg Leu Thr Arg Lys Arg Gly Leu Lys Leu Ala Thr Ala Leu Ser Leu
```

Ser Asn Lys Phe Val Glu Gly Ser Pro Ser
        35                  40

<210> SEQ ID NO 4
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 4

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 5
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 5

Thr Phe Phe Tyr Gly Gly Ser Arg Gly Lys Arg Asn Asn Phe Lys Thr
1               5                   10                  15

Glu Glu Tyr

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Asn Asn Gln Lys Ile Val Asn Leu Lys Glu Lys Val Ala Gln Leu Glu
1               5                   10                  15

Ala

<210> SEQ ID NO 7
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 7

Ala Ala Ala Ala Ala Ala Ala Ala Ala Ala Ala Ala Ala Ala Ala Ala
1               5                   10                  15

Ala Ala Ala

<210> SEQ ID NO 8
<211> LENGTH: 2211
<212> TYPE: DNA
<213> ORGANISM: Artificial Sequence
<220> FEATURE:
<223> OTHER INFORMATION: Synthetic Nucleic Acid

<400> SEQUENCE: 8
atggctgccg atggttatct tccagattgg ctcgaggaca acctctctga gggcattcgc      60
gagtggtggg acttgaaacc tggagccccg aagcccaaag ccaaccagca aaagcaggac     120

```
gacggccggg gtctggtgct tcctggctac aagtacctcg gacccttcaa cggactcgac    180 aaggggagc ccgtcaacgc ggcggacgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa ggcggctcct    420
ggaaagaaac gtccggtaga gcagtcgcca caagagccag actcctcctc gggcatcggc    480
aagacaggcc agcagcccgc taaaaagaga ctcaattttg gtcagactgg cgactcagag    540
tcagtccccg atccacaacc tctcggagaa cctccagcag ccccctcagg tctgggacct    600
aatacaatgg cttcaggcgg tggcgctcca atggcagaca taacgaagg cgccgacgga    660 gtgggtaatt cctcgggaaa ttggcattgc gattccacat ggctggggga cagagtcatc    720
accaccagca cccgaacctg ggccctgccc acctacaaca accacctcta caagcaaatc    780
tccaacggca cctcgggagg aagcaccaac gacaacacct attttggcta cagcaccccc    840
tgggggtatt ttgacttcaa cagattccac tgtcactttt caccacgtga ctggcaacga    900
ctcatcaaca caattggggg attccggccc aaaagactca acttcaagct gttcaacatc    960
caggtcaagg aagtcacgac gaacgaaggc accaagacca tcgccaataa tctcaccagc   1020
accgtgcagg tctttacgga ctcggagtac cagttaccgt acgtgctagg atccgctcac   1080
cagggatgtc tgcctccgtt cccggcggac gtcttcatgg ttcctcagta cggctattta   1140
acttaaaaca atggaagcca agccctggga cgttcctcct tctactgtct ggagtatttc   1200
ccatcgcaga tgctgagaac cggcaacaac tttcagttca gctacacctt cgaggacgtg   1260
cctttccaca gcagctacgc gcacagccag agcctggaca ggctgatgaa tccctcatc   1320 gaccagtacc tgtactacct ggtcagaacg caaacgactg aactggagg gacgcagact   1380 ctggcattca gccaagcggg tcctagctca atggccaacc aggctagaaa ttgggtgccc   1440
ggaccttgct accggcagca gcgcgtctcc acgacaacca accagaacaa caacagcaac   1500
tttgcctgga cggagctgc caagtttaag ctgaacggcc gagactctct aatgaatccg   1560
ggcgtggcaa tggcttccca caaggatgac gacgaccgct tcttcccttc gagcggggtc   1620 ctgattttg gcaagcaagg agccgggaac gatggagtgg attacagcca agtgctgatt   1680
acagatgagg aagaaatcaa ggctaccaac cccgtggcca cagaagaata tggagcagtg   1740
gccatcaaca accaggccgc caatacgcag cgcagaccg gactcgtgca caaccagggg   1800
gtgattcccg catggtgtg gcagaataga gacgtgtacc tgcagggtcc catctgggcc   1860
aaaattcctc acacggacgg caactttcac ccgtctcccc tgatgggcgg cttttggactg  1920 aagcacccgc ctcctcaaat tctcatcaag aacacaccgg ttccagcgga cccgccgctt   1980
accttcaacc aggccaagct gaactctttc atcacgcagt acagcaccgg acaggtcagc   2040
gtggaaatcg agtgggagct gcagaaagaa aacagcaaac gctggaatcc agagattcaa   2100
tacacttcca actactacaa atctacaaat gtggactttg ctgtcaacac ggaggggggtt   2160 tatagcgagc ctcgccccat ggcacccgt tacctcaccc gcaacctgta a            2211
```

<210> SEQ ID NO 9
<211> LENGTH: 2592
<212> TYPE: DNA
<213> ORGANISM: Artificial Sequence
<220> FEATURE:
<223> OTHER INFORMATION: Synthetic Nucleic Acid

<400> SEQUENCE: 9

```
ctggctgccg atggttatct tccagattgg ctcgaggaca acctctctga gggcattcgc        60
gagtggtggg acttgaaacc tggagccccg aagcccaaag ccaaccagca aaagcaggac       120
gacggccggg gtctggtgct tcctggctac aagtacctcg gacccttcaa cggactcgac       180
aagggggagc ccgtcaacgc ggcggacgca gcggccctcg agcacgacaa ggcctacgac       240
cagcagctca aagcgggtga caatccgtac ctgcggtata accacgccga cgccgagttt       300
caggagcgtc tgcaagaaga tacgtctttt gggggcaacc tcgggcgagc agtcttccag       360
gccaagaagc gggttctcga acctctcggt ctggttgagg aaggcgctaa gatggaagtg       420
cagctccaag ccagtggtgg cggactggtg caggcaggag gcagcttgag gctcagctgt       480
gccgccagcg gcttcaagat cacccactac accatgggct ggttccggca ggcccctggc       540
aaggagaggg agttcgtgag caggattacc tggggtggtg acaacacctt ctacagcaac       600
agcgtgaagg gcaggttcac catcagcagg acaacgcca agaacaccgt gtacctgcag       660
atgaacagcc tgaagcccga ggacaccgcc gactactact gtgcagccgg cagtaccagc       720
accgctaccc ccctgagggt ggactactgg ggcaaaggca ctcaggtgac agtgtcttca       780
ggaggggtg gcagcgctcc tggaaagaaa cgtccggtag agcagtcgcc acaagagcca       840
gactcctcct cgggcatcgg caagacaggc cagcagcccg ctaaaaagag actcaatttt       900
ggtcagactg gcgactcaga gtcagtcccc gatccacaac ctctcggaga acctccagca       960
gcccctcag gtctgggacc taatacaatg gcttcaggcg gtggcgctcc aatggcagac      1020
aataacgaag cgccgacgg agtgggtaat tcctcgggaa attggcattg cgattccaca      1080
tggctggggg acagagtcat caccaccagc acccgaacct gggccctgcc cacctacaac      1140
aaccacctct acaagcaaat ctccaacggc acctcgggag aagcaccaa cgacaacacc      1200
tattttggct acagcacccc ctgggggtat tttgacttca acagattcca ctgtcacttt      1260
tcaccacgtg actggcaacg actcatcaac aacaattggg gattccggcc aaaaagactc      1320
aacttcaagc tgttcaacat ccaggtcaag gaagtcacga cgaacgaagg caccaagacc      1380
atcgccaata atctcaccag caccgtgcag gtctttacgg actcggagta ccagttaccg      1440
tacgtgctag gatccgctca ccagggatgt ctgcctccgt tcccggcgga cgtcttcatg      1500
gttcctcagt acggctattt aactttaaac aatggaagcc aagccctggg acgttcctcc      1560
ttctactgtc tggagtattt cccatcgcag atgctgagaa ccggcaacaa ctttcagttc      1620
agctacacct tcgaggacgt gccttttcac agcagctacg cgcacagcca gagcctggac      1680
aggctgatga atcccctcat cgaccagtac ctgtactacc tggtcagaac gcaaacgact      1740
ggaactggag gacgcagac tctggcattc agccaagcgg gtcctagctc aatggccaac      1800
caggctagaa attgggtgcc cggaccttgc taccggcagc agcgcgtctc cacgacaacc      1860
aaccagaaca caacagcaa ctttgcctgg acgggagctg ccaagtttaa gctgaacggc      1920
cgagactctc taatgaatcc gggcgtgca atggcttccc acaaggatga cgacgaccgc      1980
ttcttcccctt cgagcggggt cctgattttt ggcaagcaag gagccgggaa cgatggagtg      2040
gattacagcc aagtgctgat tacagatgag aagaaaatca aggctaccaa ccccgtggcc      2100
acagaagaat atggagcagt ggccatcaac aaccaggccc caatacgca ggcgcagacc      2160
ggactcgtgc acaaccaggg ggtgattccc ggcatggtgt ggcagaatag agacgtgtac      2220
ctgcagggtc ccatctgggc caaaattcct cacacgacg gcaactttca cccgtctccc      2280
ctgatgggcg gctttggact gaagcacccg cctcctcaaa ttctcatcaa gaacacaccg      2340
```

```
gttccagcgg acccgccgct taccttcaac caggccaagc tgaactcttt catcacgcag    2400
tacagcaccg gacaggtcag cgtggaaatc gagtgggagc tgcagaaaga aaacagcaaa    2460
cgctggaatc cagagattca atacacttcc aactactaca aatctacaaa tgtggacttt    2520
gctgtcaaca cggagggggt ttatagcgag cctcgcccca ttggcacccg ttacctcacc    2580
cgcaacctgt aa                                                        2592
```

<210> SEQ ID NO 10
<211> LENGTH: 2601
<212> TYPE: DNA
<213> ORGANISM: Artificial Sequence
<220> FEATURE:
<223> OTHER INFORMATION: Synthetic Nucleic Acid

<400> SEQUENCE: 10

```
ctggctgccg atggttatct tccagattgg ctcgaggaca acctctctga gggcattcgc      60
gagtggtggg acttgaaacc tggagccccg aagcccaaag ccaaccagca aaagcaggac     120
gacggccggg gtctggtgct tcctggctac aagtacctcg gacccttcaa cggactcgac     180
aagggggagc ccgtcaacgc ggcggacgca gcggccctcg agcacgacaa ggcctacgac     240
cagcagctca agcgggtga caatccgtac ctgcggtata ccacgccga cgccgagttt     300 caggagcgtc tgcaagaaga tacgtctttt gggggcaacc tcgggcgagc agtcttccag     360
gccaagaagc gggttctcga acctctcggt ctggttgagg aaggcgctaa gatggaggtg     420
cagctgcagg cttctggagg aggactggtg caggctggag ggagtctgag gctgtcttgc     480
agtgcctcag tgaggacttt ctccatctac gccatgggct ggtttaggca ggctcccggg     540
aaggagcgcg aattcgtggc cggaatcaac cggtctggcg acgtgaccaa gtacgctgat     600
tccgtgaaag gccggtttag catttccaga gacaacgcca agaatatggt gtatctgcag     660
atgaactccc tgaaacctga agacacagct ctgtactatt gtgccgctac ttgggcctac     720
gataccgtgg gggctctgac atcaggatat aattttttggg gccaggggac ccaggtgaca     780
gtgagctccg gaggaggagg aagcgctcct ggaaagaaac gtccggtaga gcagtcgcca     840
caagagccag actcctcctc gggcatcggc aagacaggcc agcagcccgc taaaaagaga     900
ctcaattttg tcagactgg cgactcagag tcagtccccg atccacaacc tctcggagaa     960
cctccagcag ccccctcagg tctgggacct aatacaatgg cttcaggcgg tggcgctcca    1020
atggcagaca taacgaagg cgccgacgga gtgggtaatt cctcgggaaa ttggcattgc    1080
gattccacat ggctggggga cagagtcatc accaccagca cccgaacctg gcccctgccc    1140
acctacaaca accacctcta caagcaaatc tccaacggca cctcgggagg aagcaccaac    1200
gacaacacct attttggcta cagcaccccc tgggggtatt ttgacttcaa cagattccac    1260
tgtcactttt caccacgtga ctggcaacga ctcatcaaca caattgggg attccggccc    1320 aaaagactca acttcaagct gttcaacatc caggtcaagg aagtcacgac gaacgaaggc    1380
accaagacca tcgccaataa tctcaccagc accgtgcagg tctttacgga ctcggagtac    1440
cagttaccgt acgtgctagg atccgctcac cagggatgtc tgcctccgtt cccggcggac    1500
gtcttcatgg ttcctcagta cggctattta actttaaaca tgaagcca agccctggga    1560 cgttcctcct tctactgtct ggagtatttc ccatcgcaga tgctgagaac cggcaacaac    1620
tttcagttca gctacacctt cgaggacgtg ccttttccaca gcagctacgc gcacagccag    1680
agcctggaca ggctgatgaa tcccctcatc gaccagtacc tgtactacct ggtcagaacg    1740
```

```
caaacgactg gaactggagg gacgcagact ctggcattca gccaagcggg tcctagctca    1800
atggccaacc aggctagaaa ttgggtgccc ggaccttgct accggcagca gcgcgtctcc    1860
acgacaacca accagaacaa caacagcaac tttgcctgga cgggagctgc caagtttaag    1920
ctgaacggcc gagactctct aatgaatccg ggcgtggcaa tggcttccca caaggatgac    1980
gacgaccgct tcttcccttc gagcggggtc ctgattttg gcaagcaagg agccgggaac    2040
gatggagtgg attacagcca agtgctgatt acagatgagg aagaaatcaa ggctaccaac    2100
cccgtggcca cagaagaata tggagcagtg gccatcaaca accaggccgc caatacgcag    2160
gcgcagaccg gactcgtgca caaccagggg gtgattcccg catggtgtg cagaataga     2220
gacgtgtacc tgcagggtcc catctgggcc aaaattcctc acacggacgg caactttcac    2280
ccgtctcccc tgatgggcgg ctttggactg aagcacccgc tcctcaaat tctcatcaag    2340
aacacaccgg ttccagcgga cccgccgctt accttcaacc aggccaagct gaactctttc    2400
atcacgcagt acagcaccgg acaggtcagc gtgaaatcg agtgggagct gcagaaagaa    2460
aacagcaaac gctggaatcc agagattcaa tacacttcca actactacaa atctacaaat    2520
gtggactttg ctgtcaacac ggagggggtt tatagcgagc ctcgccccat tggcacccgt    2580
tacctcaccc gcaacctgta a                                              2601

<210> SEQ ID NO 11
<211> LENGTH: 2367
<212> TYPE: DNA
<213> ORGANISM: Artificial Sequence
<220> FEATURE:
<223> OTHER INFORMATION: Synthetic Nucleic Acid

<400> SEQUENCE: 11
ctggctgccg atggttatct tccagattgg ctcgaggaca acctctctga gggcattcgc      60
gagtggtggg acttgaaacc tggagccccg aagcccaaag ccaaccagca aaagcaggac     120
gacggccggt gtctggtgct tcctggctac aagtacctcg acccttcaa cggactcgac      180
aaggggagc ccgtcaacgc ggcggacgca gcggccctcg agcacgacaa ggcctacgac     240
cagcagctca aagcgggtga caatccgtac ctgcggtata ccacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gatgccaagc     420
agtgtaatcg atgcgctgca gtacaagctg gagggcacca cgaggctgac caggaagagg     480
ggtctgaagc tggccacggc cctcagcctt agcaataagt tcgtagaggg cagccccagc     540
ggcggcggcg gcagcggcgg cggcggcagc gctcctggaa agaaacgtcc ggtagagcag     600
tcgccacaag agccagactc ctcctcgggc atcggcaaga caggccagca gcccgctaaa     660
aagagactca atttttggtca gactggcgac tcagagtcag tccccgatcc acaacctctc     720
ggagaacctc cagcagcccc ctcaggtctg ggacctaata caatggcttc aggcggtggc     780
gctccaatgg cagacaataa cgaaggcgcc gacgagtggg taattcctc gggaaattgg     840
cattgcgatt ccacatggct gggggacaga gtcatcacca ccagcacccg aacctgggcc    900
ctgcccacct acaacaacca cctctacaag caaatctcca cggcacctc gggaggaagc     960
accaacgaca cacctatt tggctacagc acccctggg ggtattttga cttcaacaga       1020
ttccactgtc acttttcacc acgtgactgg caacgactca tcaacaacaa ttgggggattc    1080
cggcccaaaa gactcaactt caagctgttc aacatccagg tcaaggaagt cacgacgaac    1140
gaaggcacca agaccatcgc caataatctc accagcaccg tgcaggtctt tacggactcg    1200
```

```
gagtaccagt taccgtacgt gctaggatcc gctcaccagg gatgtctgcc tccgttcccg    1260
gcggacgtct tcatggttcc tcagtacggc tatttaactt taaacaatgg aagccaagcc    1320
ctgggacgtt cctccttcta ctgtctggag tatttcccat cgcagatgct gagaaccggc    1380
aacaactttc agttcagcta caccttcgag gacgtgcctt ccacagcag ctacgcgcac     1440 agccagagcc tggacaggct gatgaatccc ctcatcgacc agtacctgta ctacctggtc    1500
agaacgcaaa cgactggaac tggagggacg cagactctgg cattcagcca agcgggtcct    1560
agctcaatgg ccaaccaggc tagaaattgg gtgcccggac cttgctaccg gcagcagcgc    1620
gtctccacga caaccaacca gaacaacaac agcaactttg cctggacggg agctgccaag    1680
tttaagctga acggccgaga ctctctaatg aatccgggcg tggcaatggc ttcccacaag    1740
gatgacgacg accgcttctt cccttcgagc ggggtcctga ttttggcaa gcaaggagcc     1800 gggaacgatg gagtggatta cagccaagtg ctgattacag atgaggaaga aatcaaggct    1860
accaaccccg tggccacaga agaatatgga gcagtggcca tcaacaacca ggccgccaat    1920
acgcaggcgc agaccggact cgtgcacaac caggggtga ttcccggcat ggtgtggcag     1980
aatagagacg tgtacctgca gggtcccatc tgggccaaaa ttcctcacac ggacggcaac    2040
tttcacccgt ctcccctgat gggcggcttt ggactgaagc acccgcctcc tcaaattctc    2100
atcaagaaca caccggttcc agcggacccg ccgcttacct tcaaccaggc caagctgaac    2160
tctttcatca cgcagtacag caccggacag gtcagcgtgg aaatcgagtg ggagctgcag    2220
aaagaaaaca gcaaacgctg gaatccagag attcaataca cttccaacta ctacaaatct    2280
acaaatgtgg actttgctgt caacacggag ggggtttata gcgagcctcg ccccattggc    2340
acccgttacc tcacccgcaa cctgtaa                                        2367
```

<210> SEQ ID NO 12
<211> LENGTH: 2328
<212> TYPE: DNA
<213> ORGANISM: Artificial Sequence
<220> FEATURE:
<223> OTHER INFORMATION: Synthetic Nucleic Acid

<400> SEQUENCE: 12

```
ctggctgccg atggttatct tccagattgg ctcgaggaca acctctctga gggcattcgc    60
gagtggtggg acttgaaacc tggagccccg aagcccaaag ccaaccagca aaagcaggac    120
gacggccggg gtctggtgct tcctggctac aagtacctcg acccttcaa cggactcgac     180 aagggggagc ccgtcaacgc ggcggacgca gcggccctcg agcacgacaa ggcctacgac    240
cagcagctca agcgggtga caatccgtac ctgcggtata ccacgccga cgccgagttt     300 caggagcgtc tgcaagaaga tacgtctttt gggggcaacc tcgggcgagc agtcttccag    360
gccaagaagc gggttctcga acctctcggt ctggttgagg aaggcgctaa gatgtatacc    420
atctggatgc ccgagaaccc caggcccggt acccctgcg acatcttcac caacagcagg    480
ggcaagcgag ccagcaacgg cggcggcggc ggcagcggcg gcggcggcag cgctcctgga   540
aagaaacgtc cggtagagca gtcgccacaa gagccagact cctcctcggg catcggcaag    600
acaggccagc agcccgctaa aaagagactc aattttggtc agactggcga ctcagagtca    660
gtccccgatc cacaacctct cggagaacct ccagcagccc cctcaggtct gggacctaat    720
acaatggctt caggcggtgg cgctccaatg gcagacaata cgaaggcgc cgacggagtg    780 ggtaattcct cgggaaattg gcattgcgat tccacatggc tgggggacag agtcatcacc    840
```

```
accagcaccc gaacctgggc cctgcccacc tacaacaacc acctctacaa gcaaatctcc      900
aacggcacct cgggaggaag caccaacgac aacaccatt ttggctacag caccccctgg       960
gggtattttg acttcaacag attccactgt cacttttcac cacgtgactg gcaacgactc     1020
atcaacaaca attggggatt ccggcccaaa agactcaact tcaagctgtt caacatccag     1080
gtcaaggaag tcacgacgaa cgaaggcacc aagaccatcg ccaataatct caccagcacc     1140
gtgcaggtct ttacggactc ggagtaccag ttaccgtacg tgctaggatc cgctcaccag     1200
ggatgtctgc ctccgttccc ggcggacgtc ttcatggttc ctcagtacgg ctatttaact     1260
ttaaacaatg gaagccaagc cctgggacgt tcctccttct actgtctgga gtatttccca     1320
tcgcagatgc tgagaaccgg caacaacttt cagttcagct acaccttcga ggacgtgcct     1380
ttccacagca gctacgcgca cagccagagc ctggacaggc tgatgaatcc cctcatcgac     1440
cagtacctgt actacctggt cagaacgcaa acgactggaa ctggagggac gcagactctg     1500
gcattcagcc aagcgggtcc tagctcaatg gccaaccagg ctagaaattg ggtgcccgga     1560
ccttgctacc ggcagcagcg cgtctccacg acaaccaacc agaacaacaa cagcaacttt     1620
gcctggacgg gagctgccaa gtttaagctg aacggccgag actctctaat gaatccgggc     1680
gtggcaatgg cttcccacaa ggatgacgac accgcttct tcccttcgag cggggtcctg      1740
atttttggca gcaaggagc cgggaacgat ggagtggatt acagccaagt gctgattaca      1800
gatgaggaag aaatcaaggc taccaacccc gtggccacag aagaatatgg agcagtggcc     1860
atcaacaacc aggccgccaa tacgcaggcg cagaccggac tcgtgcacaa ccaggggtg      1920
attcccggca tggtgtggca gaatagagac gtgtacctgc agggtcccat ctgggccaaa     1980
attcctcaca cggacggcaa ctttcacccg tctcccctga tgggcggctt tggactgaag     2040
cacccgcctc ctcaaattct catcaagaac acaccggttc cagcggaccc gccgcttacc     2100
ttcaaccagg ccaagctgaa ctctttcatc acgcagtaca gcaccggaca ggtcagcgtg     2160
gaaatcgagt gggagctgca gaaagaaaac agcaaacgct ggaatccaga gattcaatac     2220
acttccaact actacaaatc tacaaatgtg acttgctg caacacgga gggggtttat        2280
agcgagcctc gccccattgg caccgttac ctcacccgca acctgtaa                    2328
```

<210> SEQ ID NO 13
<211> LENGTH: 2298
<212> TYPE: DNA
<213> ORGANISM: Artificial Sequence
<220> FEATURE:
<223> OTHER INFORMATION: Synthetic Nucleic Acid

<400> SEQUENCE: 13

```
ctggctgccg atggttatct tccagattgg ctcgaggaca acctctctga gggcattcgc       60
gagtggtggg acttgaaacc tggagccccg aagcccaaag ccaaccagca aaagcaggac      120
gacggcgggg tctggtgct tcctggctac aagtacctcg accccttcaa cggactcgac       180
aagggggagc ccgtcaacgc ggcggacgca gcggccctcg agcacgacaa ggcctacgac      240
cagcagctca aagcgggtga caatccgtac ctgcggtata accacgccga cgccgagttt      300
caggagcgtc tgcaagaaga tacgtctttt ggggcaacc tcgggcgagc agtcttccag      360
gccaagaagc gggttctcga acctctcggt ctggttgagg aaggcgctaa gatgaccttc      420
ttctacggcg gcagcagggg caagaggaac aacttcaaga ccgaggagta cggcggcggc      480
ggcagcggcg gcggcggcag cgctcctgga agaaacgtc cggtagagca gtcgccacaa      540
gagccagact cctcctcggg catcggcaag acaggccagc agcccgctaa aaagagactc      600
```

```
aattttggtc agactggcga ctcagagtca gtccccgatc cacaacctct cggagaacct    660
ccagcagccc cctcaggtct gggacctaat acaatggctt caggcggtgg cgctccaatg    720
gcagacaata cgaaggcgc cgacggagtg ggtaattcct cgggaaattg cattgcgat     780 tccacatggc tgggggacag agtcatcacc accagcaccc gaacctgggc cctgcccacc    840
tacaacaacc acctctacaa gcaaatctcc aacggcacct cgggaggaag caccaacgac    900
aacacctatt ttggctacag cacccccctgg gggtattttg acttcaacag attccactgt   960
cacttttcac cacgtgactg gcaacgactc atcaacaaca attggggatt ccggcccaaa   1020
agactcaact tcaagctgtt caacatccag gtcaaggaag tcacgacgaa cgaaggcacc   1080
aagaccatcg ccaataatct caccagcacc gtgcaggtct ttacggactc ggagtaccag   1140
ttaccgtacg tgctaggatc cgctcaccag ggatgtctgc ctccgttccc ggcggacgtc   1200
ttcatggttc ctcagtacgg ctatttaact ttaaacaatg gaagccaagc cctgggacgt   1260
tcctccttct actgtctgga gtatttccca tcgcagatgc tgagaaccgg caacaacttt   1320
cagttcagct acaccttcga ggacgtgcct ttccacagca gctacgcgca cagccagagc   1380
ctggacaggc tgatgaatcc cctcatcgac cagtacctgt actacctggt cagaacgcaa   1440
acgactggaa ctggagggac gcagactctg gcattcagcc aagcgggtcc tagctcaatg   1500
gccaaccagg ctagaaattg ggtgcccgga ccttgctacc ggcagcagcg cgtctccacg   1560
acaaccaacc agaacaacaa cagcaacttt gcctggacgg gagctgccaa gtttaagctg   1620
aacggccgag actctctaat gaatccgggc gtggcaatgg cttcccacaa ggatgacgac   1680
gaccgcttct tcccttcgag cggggtcctg attttggca agcaaggagc cgggaacgat   1740
ggagtggatt acagccaagt gctgattaca gatgaggaag aaatcaaggc taccaacccc   1800
gtggccacag aagaatatgg agcagtggcc atcaacaacc aggccgccaa tacgcaggcg   1860
cagaccggac tcgtgcacaa ccaggggtg attcccggca tggtgtggca aatagagac    1920 gtgtacctgc agggtcccat ctgggccaaa attcctcaca cggacggcaa cttcacccg    1980 tctcccctga tgggcggctt tggactgaag cacccgcctc ctcaaattct catcaagaac   2040
acaccggttc cagcggaccc gccgcttacc ttcaaccagg ccaagctgaa ctctttcatc   2100
acgcagtaca gcaccggaca ggtcagcgtg gaaatcgagt gggagctgca gaaagaaaac   2160
agcaaacgct ggaatccaga gattcaatac acttccaact actacaaatc tacaaatgtg   2220
gactttgctg tcaacacgga gggggtttat agcgagcctc gccccattgg cacccgttac   2280 ctcaccccgca acctgtaa                                                2298
```

<210> SEQ ID NO 14
<211> LENGTH: 2211
<212> TYPE: DNA
<213> ORGANISM: Artificial Sequence
<220> FEATURE:
<223> OTHER INFORMATION: Synthetic Nucleic Acid

<400> SEQUENCE: 14

```
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180 aagggggagc cggtcaacgc agcagacgcg gcggccctcg agcacgacaa ggcctacgac   240
cagcagctca aggccggaga caacccgtac ctcaagtaca ccacgccga cgccgagttc   300
```

```
caggagcggc tcaaagaaga tacgtctttt gggggcaacc tcgggcgagc agtcttccag    360
gccaaaaaga ggcttcttga acctcttggt ctggttgagg aagcggctaa ggcggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct     600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca tcacctcta caagcaaatc     780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca actacgagtt tgagaacgta   1260
cctttccata gcagctacgc tcacagccaa agcctggacc gactaatgaa tccactcatc   1320
gaccaatact tgtactatct ctcaaagact attaacgatt ctggacagaa tcaacaaacg   1380
ctaaaattca gtgtggccgg acccagcaac atggctgtcc agggaagaaa ctacataccc   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga ggaccgtt tctttccttt gtctggatct     1620
ttaatttttg gcaaacaagg aactggaaga gacaacgtgg atgcggacga agtcatgata   1680
accaacgaag aagaaattaa aactactaac ccggtagcaa cggagtccta tggacaagtg   1740
gccataaacc accagagtgc ccaagcacag gcgcagaccg gctgggttca aaaccaagga   1800
atacttccgg gtatggtttg gcaggacaga gatgtgtacc tgcaaggacc catttgggcc   1860
aaaattcctc acacgacgg caactttcac ccttctccgc tgatgggagg gtttggaatg    1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a            2211
```

<210> SEQ ID NO 15
<211> LENGTH: 2277
<212> TYPE: DNA
<213> ORGANISM: Artificial Sequence
<220> FEATURE:
<223> OTHER INFORMATION: Synthetic Nucleic Acid

<400> SEQUENCE: 15

```
ctggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct tccgggttac aaataccttg gacccggcaa cggactcgac    180
```

| | |
|---|---|
| aaggggggagc cggtcaacgc agcagacgcg gcggccctcg agcacgacaa ggcctacgac | 240 |
| cagcagctca aggccggaga caacccgtac ctcaagtaca accacgccga cgccgagttc | 300 |
| caggagcggc tcaaagaaga tacgtctttt gggggcaacc tcgggcgagc agtcttccag | 360 |
| gccaaaaaga ggcttcttga acctcttggt ctggttgagg aagcggctaa gatgaacaac | 420 |
| cagaagatcg tgaacctgaa ggagaaggtg gcccagctgg aggccggcgg cggcggcagc | 480 |
| gctcctggaa agaagaggcc tgtagagcag tctcctcagg aaccggactc ctccgcgggt | 540 |
| attggcaaat cgggtgcaca gcccgctaaa aagagactca atttcggtca gactggcgac | 600 |
| acagagtcag tcccagaccc tcaaccaatc ggagaacctc ccgcagcccc ctcaggtgtg | 660 |
| ggatctctta caatggcttc aggtggtggc gcaccagtgg cagacaataa cgaaggtgcc | 720 |
| gatggagtgg gtagttcctc gggaaattgg cattgcgatt cccaatggct ggggggacaga | 780 |
| gtcatcacca ccagcacccg aacctgggcc ctgcccacct acaacaatca cctctacaag | 840 |
| caaatctcca cagcacatc tggaggatct tcaaatgaca acgcctactt cggctacagc | 900 |
| acccccttggg ggtattttga cttcaacaga ttccactgcc acttctcacc acgtgactgg | 960 |
| cagcgactca tcaacaacaa ctggggattc cggcctaagc gactcaactt caagctcttc | 1020 |
| aacattcagg tcaaagaggt tacggacaac aatggagtca agaccatcgc caataacctt | 1080 |
| accagcacgg tccaggtctt cacggactca gactatcagc tcccgtacgt gctcgggtcg | 1140 |
| gctcacgagg gctgcctccc gccgttccca gcggacgttt tcatgattcc tcagtacggg | 1200 |
| tatctgacgc ttaatgatgg aagccaggcc gtgggtcgtt cgtcctttta ctgcctggaa | 1260 |
| tatttcccgt cgcaaatgct aagaacgggt aacaacttcc agttcaacta cgagtttgag | 1320 |
| aacgtacctt tccatagcag ctacgctcac agccaaagcc tggaccgact aatgaatcca | 1380 |
| ctcatcgacc aatacttgta ctatctctca aagactatta cgattctgg acagaatcaa | 1440 |
| caaacgctaa aattcagtgt ggccggaccc agcaacatgg ctgtccaggg aagaaactac | 1500 |
| atacctggac ccagctaccg acaacaacgt gtctcaacca ctgtgactca aaacaacaac | 1560 |
| agcgaatttg cttggcctgg agcttcttct tgggctctca atggacgtaa tagcttgatg | 1620 |
| aatcctggac ctgctatggc cagccacaaa gaaggagagg accgtttctt tccttttgtct | 1680 |
| ggatctttaa tttttggcaa acaaggaact ggaagagaca acgtggatgc ggacgaagtc | 1740 |
| atgataacca acgaagaaga aattaaaact actaacccgg tagcaacgga gtcctatgga | 1800 |
| caagtggcca taaccacca gagtgcccaa gcacaggcgc agaccggctg ggttcaaaac | 1860 |
| caaggaatac ttccgggtat ggtttggcag gacagagatg tgtacctgca aggacccatt | 1920 |
| tgggccaaaa ttcctcacac ggacggcaac tttcaccctt ctccgctgat gggagggttt | 1980 |
| ggaatgaagc acccgcctcc tcagatcctc atcaaaaaca cacctgtacc tgcggatcct | 2040 |
| ccaacggcct tcaacaagga caagctgaac tctttcatca cccagtattc tactggccaa | 2100 |
| gtcagcgtgg agatcgagtg ggagctgcag aaggaaaaca gcaagcgctg gaacccggag | 2160 |
| atccagtaca cttccaacta ttacaagtct aataatgttg aatttgctgt taatactgaa | 2220 |
| ggtgtatata gtgaaccccg ccccattggc accagatacc tgactcgtaa tctgtaa | 2277 |

<210> SEQ ID NO 16
<211> LENGTH: 2313
<212> TYPE: DNA
<213> ORGANISM: Artificial Sequence
<220> FEATURE:
<223> OTHER INFORMATION: Synthetic Nucleic Acid

<400> SEQUENCE: 16

```
ctggctgccg atggttatct tccagattgg ctcgaggaca accttagtga aggaattcgc      60
gagtggtggg ctttgaaacc tggagcccct caacccaagg caaatcaaca acatcaagac     120
aacgctcgag gtcttgtgct tccgggttac aaataccttg acccggcaa cggactcgac     180
aaggggagc cggtcaacgc agcagacgcg gcggccctcg agcacgacaa ggcctacgac     240
cagcagctca aggccggaga caacccgtac ctcaagtaca accacgccga cgccgagttc     300
caggagcggc tcaaagaaga tacgtctttt gggggcaacc tcgggcgagc agtcttccag     360
gccaaaaaga ggcttcttga acctcttggt ctggttgagg aagcggctaa gatgtatacc     420
atctggatgc ccgagaaccc caggcccggt accccctgcg acatcttcac caacagcagg     480
ggcaagcgag ccagcaacgg cggcggcggc ggcagcgctc ctggaaagaa gaggcctgta     540
gagcagtctc ctcaggaacc ggactcctcc gcgggtattg gcaaatcggg tgcacagccc     600
gctaaaaaga gactcaattt cggtcagact ggcgacacag agtcagtccc agaccctcaa     660
ccaatcggag aacctcccgc agcccccctca ggtgtgggat ctcttacaat ggcttcaggt     720
ggtggcgcac cagtggcaga caataacgaa ggtgccgatg gagtgggtag ttcctcggga     780
aattggcatt gcgattccca atggctgggg gacagagtca tcaccaccag cacccgaacc     840
tgggcccctgc ccacctacaa caatcacctc tacaagcaaa tctccaacag cacatctgga     900
ggatcttcaa atgacaacgc ctacttcggc tacagcaccc cctgggggta ttttgacttc     960
aacagattcc actgccactt ctccaccacgt gactggcagc gactcatcaa caacaactgg    1020
ggattccggc ctaagcgact caacttcaag ctccttcaaca ttcaggtcaa agaggttacg    1080
gacaacaatg gagtcaagac catcgccaat aaccttacca gcacggtcca ggtcttcacg    1140
gactcagact atcagctccc gtacgtgctc ggtcggctc acgagggctg cctcccgccg    1200
ttcccagcgg acgttttcat gattcctcag tacgggtatc tgacgcttaa tgatggaagc    1260
caggccgtgg tcgttcgtc cttttactgc ctggaatatt tcccgtcgca aatgctaaga    1320
acgggtaaca acttccagtt caactacgag tttgagaacg tacctttcca tagcagctac    1380
gctcacagcc aaagcctgga ccgactaatg aatccactca tcgaccaata cttgtactat    1440
ctctcaaaga ctattaacga ttctggacag aatcaacaaa cgctaaaatt cagtgtggcc    1500
ggacccagca catggctgt ccagggaaga aactacatac ctggacccag ctaccgacaa    1560
caacgtgtct caaccactgt gactcaaaac aacaacagcg aatttgcttg gcctggagct    1620
tcttcttggg ctctcaatgg acgtaatagc ttgatgaatc ctggacctgc tatggccagc    1680
cacaaagaag gagaggaccg tttctttcct ttgtctggat ctttaatttt tggcaaacaa    1740
ggaactggaa gagacaacgt ggatgcggac gaagtcatga taaccaacga agaagaaatt    1800
aaaactacta acccggtagc aacggagtcc tatggacaag tggccataaa ccaccagagt    1860
gcccaagcac aggcgcagac cggctgggtt caaaaccaag gaatacttcc gggtatggtt    1920
tggcaggaca gagatgtgta cctgcaagga cccatttggg ccaaaattcc tcacacggac    1980
ggcaactttc acccttctcc gctgatggga gggtttggaa tgaagcaccc gcctcctcag    2040
atcctcatca aaaacacacc tgtacctgcg atcctccaa cggccttcaa caaggacaag    2100
ctgaactctt tcatcaccca gtattctact ggccaagtca gcgtggagat cgagtgggag    2160
ctgcagaagg aaaacagcaa gcgctggaac ccgagatcc agtacacttc caactattac    2220
aagtctaata atgttgaatt tgctgttaat actgaaggtg tatatagtga accccgcccc    2280
attggcacca gataccctgac tcgtaatctg taa                                 2313
```

<210> SEQ ID NO 17
<211> LENGTH: 2283
<212> TYPE: DNA
<213> ORGANISM: Artificial Sequence
<220> FEATURE:
<223> OTHER INFORMATION: Synthetic Nucleic Acid

<400> SEQUENCE: 17

| | | | | | |
|---|---|---|---|---|---|
| ctggctgccg | atggttatct | tccagattgg | ctcgaggaca | accttagtga | aggaattcgc | 60 |
| gagtggtggg | ctttgaaacc | tggagcccct | caacccaagg | caaatcaaca | acatcaagac | 120 |
| aacgctcgag | gtcttgtgct | tccgggttac | aaataccttg | acccggcaa | cggactcgac | 180 |
| aaggggagc | cggtcaacgc | agcagacgcg | gcggccctcg | agcacgacaa | ggcctacgac | 240 |
| cagcagctca | aggccggaga | caacccgtac | ctcaagtaca | accacgccga | cgccgagttc | 300 |
| caggagcggc | tcaaagaaga | tacgtctttt | gggggcaacc | tcgggcgagc | agtcttccag | 360 |
| gccaaaaaga | ggcttcttga | acctcttggt | ctggttgagg | aagcggctaa | gatgaccttc | 420 |
| ttctacggcg | gcagcagggg | caagaggaac | aacttcaaga | ccgaggagta | cggcggcggc | 480 |
| ggcagcgctc | ctggaaagaa | gaggcctgta | gagcagtctc | ctcaggaacc | ggactcctcc | 540 |
| gcgggtattg | gcaaatcggg | tgcacagccc | gctaaaaaga | gactcaattt | cggtcagact | 600 |
| ggcgacacag | agtcagtccc | agaccctcaa | ccaatcggag | aacctcccgc | agcccctca | 660 |
| ggtgtgggat | ctcttacaat | ggcttcaggt | ggtggcgcac | cagtggcaga | caataacgaa | 720 |
| ggtgccgatg | gagtgggtag | ttcctcggga | aattggcatt | gcgattccca | atggctgggg | 780 |
| gacagagtca | tcaccaccag | cacccgaacc | tgggccctgc | ccacctacaa | caatcacctc | 840 |
| tacaagcaaa | tctccaacag | cacatctgga | ggatcttcaa | atgacaacgc | ctacttcggc | 900 |
| tacagcaccc | cctgggggta | ttttgacttc | aacagattcc | actgccactt | ctcaccacgt | 960 |
| gactggcagc | gactcatcaa | caacaactgg | ggattccggc | ctaagcgact | caacttcaag | 1020 |
| ctcttcaaca | ttcaggtcaa | agaggttacg | gacaacaatg | gagtcaagac | catcgccaat | 1080 |
| aaccttacca | gcacggtcca | ggtcttcacg | gactcagact | atcagctccc | gtacgtgctc | 1140 |
| gggtcggctc | acgagggctg | cctcccgccg | ttcccagcgg | acgttttcat | gattcctcag | 1200 |
| tacgggtatc | tgacgcttaa | tgatggaagc | caggccgtgg | gtcgttcgtc | cttttactgc | 1260 |
| ctggaatatt | tcccgtcgca | aatgctaaga | acgggtaaca | acttccagtt | caactacgag | 1320 |
| tttgagaacg | tacctttcca | tagcagctac | gctcacagcc | aaagcctgga | ccgactaatg | 1380 |
| aatccactca | tcgaccaata | cttgtactat | ctctcaaaga | ctattaacga | ttctggacag | 1440 |
| aatcaacaaa | cgctaaaatt | cagtgtggcc | ggacccagca | acatggctgt | ccagggaaga | 1500 |
| aactacatac | ctggacccag | ctaccgacaa | caacgtgtct | caaccactgt | gactcaaaac | 1560 |
| aacaacagcg | aatttgcttg | gcctggagct | tcttcttggg | ctctcaatgg | acgtaatagc | 1620 |
| ttgatgaatc | ctggacctgc | tatggccagc | cacaaagaag | gagaggaccg | tttctttcct | 1680 |
| ttgtctggat | cttaattt | tggcaaacaa | ggaactggaa | gagacaacgt | ggatgcggac | 1740 |
| gaagtcatga | taaccaacga | agaagaaatt | aaaactacta | acccggtagc | aacggagtcc | 1800 |
| tatggacaag | tggccataaa | ccaccagagt | gcccaagcac | aggcgcagac | cggctgggtt | 1860 |
| caaaaccaag | gaatacttcc | gggtatggtt | tggcaggaca | gagatgtgta | cctgcaagga | 1920 |
| cccatttggg | ccaaaattcc | tcacacggac | ggcaactttc | accttctcc | gctgatggga | 1980 |
| gggtttggaa | tgaagcaccc | gcctcctcag | atcctcatca | aaaacacacc | tgtacctgcg | 2040 |

```
gatcctccaa cggccttcaa caaggacaag ctgaactctt tcatcaccca gtattctact    2100
ggccaagtca gcgtggagat cgagtgggag ctgcagaagg aaaacagcaa gcgctggaac    2160
ccggagatcc agtacacttc caactattac aagtctaata atgttgaatt tgctgttaat    2220
actgaaggtg tatatagtga accccgcccc attggcacca gataccctgac tcgtaatctg    2280 taa                                                                 2283
```

<210> SEQ ID NO 18
<211> LENGTH: 2283
<212> TYPE: DNA
<213> ORGANISM: Artificial Sequence
<220> FEATURE:
<223> OTHER INFORMATION: Synthetic Nucleic Acid

<400> SEQUENCE: 18

```
ctggctgccg atggttatct tccagattgg ctcgaggaca accttagtga aggaattcgc      60
gagtggtggg cttgaaacc tggagcccct caacccaagg caaatcaaca acatcaagac     120
aacgctcgag gtcttgtgct tccgggttac aaataccttg acccggcaa cggactcgac     180 aaggggagc cggtcaacgc agcagacgcg gcggccctcg agcacgacaa ggcctacgac     240
cagcagctca aggccggaga caacccgtac ctcaagtaca ccacgccga cgccgagttc     300 caggagcggc tcaaagaaga tacgtctttt gggggcaacc tcgggcgagc agtcttccag     360
gccaaaaaga ggcttcttga acctcttggt ctggttgagg aagcggctaa gatggcagct     420
gcggccgccg cggctgcagc ggctgcagcc gccgcagctg cggctgcagc gggcggcggc     480
ggcagcgctc ctgaaagaa gaggcctgta gagcagtctc ctcaggaacc ggactcctcc     540
gcgggtattg gcaaatcggg tgcacagccc gctaaaaaga gactcaattt cggtcagact     600
ggcgacacag agtcagtccc agaccctcaa ccaatcggag aacctcccgc agccccctca     660
ggtgtgggat ctcttacaat ggcttcaggt ggtggcgcac cagtggcaga caataacgaa     720
ggtgccgatg gagtgggtag ttcctcggga aattggcatt gcgattccca atggctgggg     780
gacagagtca tcaccaccag cacccgaacc tgggccctgc ccacctacaa caatcacctc     840
tacaagcaaa tctccaacag cacatctgga ggatcttcaa atgacaacgc ctacttcggc     900
tacagcaccc cctgggggta ttttgacttc aacagattcc actgccactt ctcaccacgt     960
gactggcagc gactcatcaa caacaactgg ggattccggc ctaagcgact caacttcaag    1020
ctcttcaaca ttcaggtcaa agaggttacg gacaacaatg gagtcaagac catcgccaat    1080
aaccttacca gcacggtcca ggtcttcacg gactcagact atcagctccc gtacgtgctc    1140
gggtcggctc acgagggctg cctcccgccg ttcccagcgg acgttttcat gattcctcag    1200
tacgggtatc tgacgcttaa tgatggaagc caggccgtgg tcgttcgtc ctttactgc      1260 ctggaatatt tcccgtcgca aatgctaaga acgggtaaca acttccagtt caactacgag    1320
tttgagaacg tacctttcca tagcagctac gctcacagcc aaagcctgga ccgactaatg    1380
aatccactca tcgaccaata cttgtactat ctctcaaaga ctattaacga ttctggacag    1440
aatcaacaaa cgctaaaatt cagtgtggcc ggacccagca catggctgt ccaggaaga     1500 aactacatac ctggacccag ctaccgacaa caacgtgtct caaccactgt gactcaaaac    1560
aacaacagcg aatttgcttg gcctggagct tcttcttggg ctctcaatgg acgtaatagc    1620
ttgatgaatc ctggacctgc tatgccagc cacaaagaag gagaggaccg tttcttcct     1680 ttgtctggat ctttaatttt tggcaaacaa ggaactggaa gagacaacgt ggatgcggac    1740
gaagtcatga taaccaacga agaagaaatt aaaactacta acccggtagc aacggagtcc    1800
```

```
tatggacaag tggccataaa ccaccagagt gcccaagcac aggcgcagac cggctgggtt    1860
caaaaccaag gaatacttcc gggtatggtt tggcaggaca gagatgtgta cctgcaagga    1920
cccatttggg ccaaaattcc tcacacggac ggcaactttc accttctcc gctgatggga     1980 gggtttggaa tgaagcaccc gcctcctcag atcctcatca aaaacacacc tgtacctgcg    2040
gatcctccaa cggccttcaa caaggacaag ctgaactctt tcatcaccca gtattctact    2100
ggccaagtca gcgtggagat cgagtgggag ctgcagaagg aaaacagcaa cgctggaac     2160 ccggagatcc agtacacttc caactattac aagtctaata atgttgaatt tgctgttaat    2220
actgaaggtg tatatagtga accccgcccc attggcacca gatacctgac tcgtaatctg    2280
taa                                                                 2283

<210> SEQ ID NO 19
<211> LENGTH: 726
<212> TYPE: PRT
<213> ORGANISM: Artificial Sequence
<220> FEATURE:
<223> OTHER INFORMATION: Synthetic Polypeptide

<400> SEQUENCE: 19

Met Glu Val Gln Leu Gln Ala Ser Gly Gly Gly Leu Val Gln Ala Gly
1               5                   10                  15

Gly Ser Leu Arg Leu Ser Cys Ala Ala Ser Gly Phe Lys Ile Thr His
            20                  25                  30

Tyr Thr Met Gly Trp Phe Arg Gln Ala Pro Gly Lys Glu Arg Glu Phe
        35                  40                  45

Val Ser Arg Ile Thr Trp Gly Gly Asp Asn Thr Phe Tyr Ser Asn Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Asp Tyr Tyr
                85                  90                  95

Cys Ala Ala Gly Ser Thr Ser Thr Ala Thr Pro Leu Arg Val Asp Tyr
            100                 105                 110

Trp Gly Lys Gly Thr Gln Val Thr Val Ser Ser Gly Gly Gly Gly Ser
        115                 120                 125

Ala Pro Gly Lys Lys Arg Pro Val Glu Gln Ser Pro Gln Glu Pro Asp
    130                 135                 140

Ser Ser Ser Gly Ile Gly Lys Thr Gly Gln Gln Pro Ala Lys Lys Arg
145                 150                 155                 160

Leu Asn Phe Gly Gln Thr Gly Asp Ser Glu Ser Val Pro Asp Pro Gln
                165                 170                 175

Pro Leu Gly Glu Pro Pro Ala Ala Pro Ser Gly Leu Gly Pro Asn Thr
            180                 185                 190

Met Ala Ser Gly Gly Gly Ala Pro Met Ala Asp Asn Asn Glu Gly Ala
        195                 200                 205

Asp Gly Val Gly Asn Ser Ser Gly Asn Trp His Cys Asp Ser Thr Trp
    210                 215                 220

Leu Gly Asp Arg Val Ile Thr Thr Ser Thr Arg Thr Trp Ala Leu Pro
225                 230                 235                 240

Thr Tyr Asn Asn His Leu Tyr Lys Gln Ile Ser Asn Gly Thr Ser Gly
                245                 250                 255

Gly Ser Thr Asn Asp Asn Thr Tyr Phe Gly Tyr Ser Thr Pro Trp Gly
            260                 265                 270
```

```
Tyr Phe Asp Phe Asn Arg Phe His Cys His Phe Ser Pro Arg Asp Trp
        275                 280                 285

Gln Arg Leu Ile Asn Asn Trp Gly Phe Arg Pro Lys Arg Leu Asn
290                 295                 300

Phe Lys Leu Phe Asn Ile Gln Val Lys Glu Val Thr Thr Asn Glu Gly
305                 310                 315                 320

Thr Lys Thr Ile Ala Asn Asn Leu Thr Ser Thr Val Gln Val Phe Thr
                325                 330                 335

Asp Ser Glu Tyr Gln Leu Pro Tyr Val Leu Gly Ser Ala His Gln Gly
                340                 345                 350

Cys Leu Pro Pro Phe Pro Ala Asp Val Phe Met Val Pro Gln Tyr Gly
                355                 360                 365

Tyr Leu Thr Leu Asn Asn Gly Ser Gln Ala Leu Gly Arg Ser Ser Phe
370                 375                 380

Tyr Cys Leu Glu Tyr Phe Pro Ser Gln Met Leu Arg Thr Gly Asn Asn
385                 390                 395                 400

Phe Gln Phe Ser Tyr Thr Phe Glu Asp Val Pro Phe His Ser Ser Tyr
                405                 410                 415

Ala His Ser Gln Ser Leu Asp Arg Leu Met Asn Pro Leu Ile Asp Gln
                420                 425                 430

Tyr Leu Tyr Tyr Leu Val Arg Thr Gln Thr Thr Gly Thr Gly Gly Thr
                435                 440                 445

Gln Thr Leu Ala Phe Ser Gln Ala Gly Pro Ser Ser Met Ala Asn Gln
450                 455                 460

Ala Arg Asn Trp Val Pro Gly Pro Cys Tyr Arg Gln Gln Arg Val Ser
465                 470                 475                 480

Thr Thr Thr Asn Gln Asn Asn Asn Ser Asn Phe Ala Trp Thr Gly Ala
                485                 490                 495

Ala Lys Phe Lys Leu Asn Gly Arg Asp Ser Leu Met Asn Pro Gly Val
                500                 505                 510

Ala Met Ala Ser His Lys Asp Asp Asp Arg Phe Phe Pro Ser Ser
                515                 520                 525

Gly Val Leu Ile Phe Gly Lys Gln Gly Ala Gly Asn Asp Gly Val Asp
530                 535                 540

Tyr Ser Gln Val Leu Ile Thr Asp Glu Glu Ile Lys Ala Thr Asn
545                 550                 555                 560

Pro Val Ala Thr Glu Glu Tyr Gly Ala Val Ala Ile Asn Asn Gln Ala
                565                 570                 575

Ala Asn Thr Gln Ala Gln Thr Gly Leu Val His Asn Gln Gly Val Ile
                580                 585                 590

Pro Gly Met Val Trp Gln Asn Arg Asp Val Tyr Leu Gln Gly Pro Ile
                595                 600                 605

Trp Ala Lys Ile Pro His Thr Asp Gly Asn Phe His Pro Ser Pro Leu
610                 615                 620

Met Gly Gly Phe Gly Leu Lys His Pro Pro Gln Ile Leu Ile Lys
625                 630                 635                 640

Asn Thr Pro Val Pro Ala Asp Pro Pro Leu Thr Phe Asn Gln Ala Lys
                645                 650                 655

Leu Asn Ser Phe Ile Thr Gln Tyr Ser Thr Gly Gln Val Ser Val Glu
                660                 665                 670

Ile Glu Trp Glu Leu Gln Lys Glu Asn Ser Lys Arg Trp Asn Pro Glu
                675                 680                 685
```

```
Ile Gln Tyr Thr Ser Asn Tyr Tyr Lys Ser Thr Asn Val Asp Phe Ala
    690                 695                 700

Val Asn Thr Glu Gly Val Tyr Ser Glu Pro Arg Pro Ile Gly Thr Arg
705                 710                 715                 720

Tyr Leu Thr Arg Asn Leu
                725

<210> SEQ ID NO 20
<211> LENGTH: 729
<212> TYPE: PRT
<213> ORGANISM: Artificial Sequence
<220> FEATURE:
<223> OTHER INFORMATION: Synthetic Polypeptide

<400> SEQUENCE: 20

Met Glu Val Gln Leu Gln Ala Ser Gly Gly Gly Leu Val Gln Ala Gly
1               5                   10                  15

Gly Ser Leu Arg Leu Ser Cys Ser Ala Ser Val Arg Thr Phe Ser Ile
            20                  25                  30

Tyr Ala Met Gly Trp Phe Arg Gln Ala Pro Gly Lys Glu Arg Glu Phe
        35                  40                  45

Val Ala Gly Ile Asn Arg Ser Gly Asp Val Thr Lys Tyr Ala Asp Phe
50                  55                  60

Val Lys Gly Arg Phe Ser Ile Ser Arg Asp Asn Ala Lys Asn Met Val
65                  70                  75                  80

Tyr Leu Gln Met Asn Ser Leu Lys Pro Glu Asp Thr Ala Leu Tyr Tyr
                85                  90                  95

Cys Ala Ala Thr Trp Ala Tyr Asp Thr Val Gly Ala Leu Thr Ser Gly
            100                 105                 110

Tyr Asn Phe Trp Gly Gln Gly Thr Gln Val Thr Val Ser Ser Gly Gly
        115                 120                 125

Gly Gly Ser Ala Pro Gly Lys Lys Arg Pro Val Glu Gln Ser Pro Gln
130                 135                 140

Glu Pro Asp Ser Ser Ser Gly Ile Gly Lys Thr Gly Gln Gln Pro Ala
145                 150                 155                 160

Lys Lys Arg Leu Asn Phe Gly Gln Thr Gly Asp Ser Glu Ser Val Pro
                165                 170                 175

Asp Pro Gln Pro Leu Gly Glu Pro Pro Ala Ala Pro Ser Gly Leu Gly
            180                 185                 190

Pro Asn Thr Met Ala Ser Gly Gly Ala Pro Met Ala Asp Asn Asn
        195                 200                 205

Glu Gly Ala Asp Gly Val Gly Asn Ser Ser Gly Asn Trp His Cys Asp
210                 215                 220

Ser Thr Trp Leu Gly Asp Arg Val Ile Thr Thr Ser Thr Arg Thr Trp
225                 230                 235                 240

Ala Leu Pro Thr Tyr Asn Asn His Leu Tyr Lys Gln Ile Ser Asn Gly
                245                 250                 255

Thr Ser Gly Gly Ser Thr Asn Asp Asn Thr Tyr Phe Gly Tyr Ser Thr
            260                 265                 270

Pro Trp Gly Tyr Phe Asp Phe Asn Arg Phe His Cys His Phe Ser Pro
        275                 280                 285

Arg Asp Trp Gln Arg Leu Ile Asn Asn Asn Trp Gly Phe Arg Pro Lys
290                 295                 300

Arg Leu Asn Phe Lys Leu Phe Asn Ile Gln Val Lys Glu Val Thr Thr
305                 310                 315                 320
```

-continued

```
Asn Glu Gly Thr Lys Thr Ile Ala Asn Asn Leu Thr Ser Thr Val Gln
            325                 330                 335

Val Phe Thr Asp Ser Glu Tyr Gln Leu Pro Tyr Val Leu Gly Ser Ala
            340                 345                 350

His Gln Gly Cys Leu Pro Pro Phe Pro Ala Asp Val Phe Met Val Pro
            355                 360                 365

Gln Tyr Gly Tyr Leu Thr Leu Asn Asn Gly Ser Gln Ala Leu Gly Arg
            370                 375                 380

Ser Ser Phe Tyr Cys Leu Glu Tyr Phe Pro Ser Gln Met Leu Arg Thr
385                 390                 395                 400

Gly Asn Asn Phe Gln Phe Ser Tyr Thr Phe Glu Asp Val Pro Phe His
            405                 410                 415

Ser Ser Tyr Ala His Ser Gln Ser Leu Asp Arg Leu Met Asn Pro Leu
            420                 425                 430

Ile Asp Gln Tyr Leu Tyr Tyr Leu Val Arg Thr Gln Thr Thr Gly Thr
            435                 440                 445

Gly Gly Thr Gln Thr Leu Ala Phe Ser Gln Ala Gly Pro Ser Ser Met
            450                 455                 460

Ala Asn Gln Ala Arg Asn Trp Val Pro Gly Pro Cys Tyr Arg Gln Gln
465                 470                 475                 480

Arg Val Ser Thr Thr Thr Asn Gln Asn Asn Asn Ser Asn Phe Ala Trp
            485                 490                 495

Thr Gly Ala Ala Lys Phe Lys Leu Asn Gly Arg Asp Ser Leu Met Asn
            500                 505                 510

Pro Gly Val Ala Met Ala Ser His Lys Asp Asp Asp Arg Phe Phe
            515                 520                 525

Pro Ser Ser Gly Val Leu Ile Phe Gly Lys Gln Gly Ala Gly Asn Asp
            530                 535                 540

Gly Val Asp Tyr Ser Gln Val Leu Ile Thr Asp Glu Glu Glu Ile Lys
545                 550                 555                 560

Ala Thr Asn Pro Val Ala Thr Glu Glu Tyr Gly Ala Val Ala Ile Asn
            565                 570                 575

Asn Gln Ala Ala Asn Thr Gln Ala Gln Thr Gly Leu Val His Asn Gln
            580                 585                 590

Gly Val Ile Pro Gly Met Val Trp Gln Asn Arg Asp Val Tyr Leu Gln
            595                 600                 605

Gly Pro Ile Trp Ala Lys Ile Pro His Thr Asp Gly Asn Phe His Pro
            610                 615                 620

Ser Pro Leu Met Gly Gly Phe Gly Leu Lys His Pro Pro Gln Ile
625                 630                 635                 640

Leu Ile Lys Asn Thr Pro Val Pro Ala Asp Pro Pro Leu Thr Phe Asn
            645                 650                 655

Gln Ala Lys Leu Asn Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
            675                 680                 685

Asn Pro Glu Ile Gln Tyr Thr Ser Asn Tyr Tyr Lys Ser Thr Asn Val
            690                 695                 700

Asp Phe Ala Val Asn Thr Glu Gly Val Tyr Ser Glu Pro Arg Pro Ile
705                 710                 715                 720

Gly Thr Arg Tyr Leu Thr Arg Asn Leu
            725
```

```
<210> SEQ ID NO 21
<211> LENGTH: 651
<212> TYPE: PRT
<213> ORGANISM: Artificial Sequence
<220> FEATURE:
<223> OTHER INFORMATION: Synthetic Polypeptide

<400> SEQUENCE: 21
```

Met Pro Ser Ser Val Ile Asp Ala Leu Gln Tyr Lys Leu Glu Gly Thr
1               5                   10                  15

Thr Arg Leu Thr Arg Lys Arg Gly Leu Lys Leu Ala Thr Ala Leu Ser
            20                  25                  30

Leu Ser Asn Lys Phe Val Glu Gly Ser Pro Ser Gly Gly Gly Gly Ser
        35                  40                  45

Gly Gly Gly Gly Ser Ala Pro Gly Lys Lys Arg Pro Val Glu Gln Ser
    50                  55                  60

Pro Gln Glu Pro Asp Ser Ser Gly Ile Gly Lys Thr Gly Gln Gln
65                  70                  75                  80

Pro Ala Lys Lys Arg Leu Asn Phe Gly Gln Thr Gly Asp Ser Glu Ser
                85                  90                  95

Val Pro Asp Pro Gln Pro Leu Gly Glu Pro Pro Ala Ala Pro Ser Gly
            100                 105                 110

Leu Gly Pro Asn Thr Met Ala Ser Gly Gly Gly Ala Pro Met Ala Asp
        115                 120                 125

Asn Asn Glu Gly Ala Asp Gly Val Gly Asn Ser Ser Gly Asn Trp His
    130                 135                 140

Cys Asp Ser Thr Trp Leu Gly Asp Arg Val Ile Thr Thr Ser Thr Arg
145                 150                 155                 160

Thr Trp Ala Leu Pro Thr Tyr Asn Asn His Leu Tyr Lys Gln Ile Ser
                165                 170                 175

Asn Gly Thr Ser Gly Gly Ser Thr Asn Asp Asn Thr Tyr Phe Gly Tyr
            180                 185                 190

Ser Thr Pro Trp Gly Tyr Phe Asp Phe Asn Arg Phe His Cys His Phe
        195                 200                 205

Ser Pro Arg Asp Trp Gln Arg Leu Ile Asn Asn Trp Gly Phe Arg
    210                 215                 220

Pro Lys Arg Leu Asn Phe Lys Leu Phe Asn Ile Gln Val Lys Glu Val
225                 230                 235                 240

Thr Thr Asn Glu Gly Thr Lys Thr Ile Ala Asn Asn Leu Thr Ser Thr
                245                 250                 255

Val Gln Val Phe Thr Asp Ser Glu Tyr Gln Leu Pro Tyr Val Leu Gly
            260                 265                 270

Ser Ala His Gln Gly Cys Leu Pro Pro Phe Pro Ala Asp Val Phe Met
        275                 280                 285

Val Pro Gln Tyr Gly Tyr Leu Thr Leu Asn Asn Gly Ser Gln Ala Leu
    290                 295                 300

Gly Arg Ser Ser Phe Tyr Cys Leu Glu Tyr Phe Pro Ser Gln Met Leu
305                 310                 315                 320

Arg Thr Gly Asn Asn Phe Gln Phe Ser Tyr Thr Phe Glu Asp Val Pro
                325                 330                 335

Phe His Ser Ser Tyr Ala His Ser Gln Ser Leu Asp Arg Leu Met Asn
            340                 345                 350

Pro Leu Ile Asp Gln Tyr Leu Tyr Tyr Leu Val Arg Thr Gln Thr Thr
        355                 360                 365

Gly Thr Gly Gly Thr Gln Thr Leu Ala Phe Ser Gln Ala Gly Pro Ser

```
                370                 375                 380
Ser Met Ala Asn Gln Ala Arg Asn Trp Val Pro Gly Pro Cys Tyr Arg
385                 390                 395                 400

Gln Gln Arg Val Ser Thr Thr Thr Asn Gln Asn Asn Asn Ser Asn Phe
                405                 410                 415

Ala Trp Thr Gly Ala Ala Lys Phe Lys Leu Asn Gly Arg Asp Ser Leu
                420                 425                 430

Met Asn Pro Gly Val Ala Met Ala Ser His Lys Asp Asp Asp Asp Arg
                435                 440                 445

Phe Phe Pro Ser Ser Gly Val Leu Ile Phe Gly Lys Gln Gly Ala Gly
                450                 455                 460

Asn Asp Gly Val Asp Tyr Ser Gln Val Leu Ile Thr Asp Glu Glu Glu
465                 470                 475                 480

Ile Lys Ala Thr Asn Pro Val Ala Thr Glu Glu Tyr Gly Ala Val Ala
                485                 490                 495

Ile Asn Asn Gln Ala Ala Asn Thr Gln Ala Gln Thr Gly Leu Val His
                500                 505                 510

Asn Gln Gly Val Ile Pro Gly Met Val Trp Gln Asn Arg Asp Val Tyr
                515                 520                 525

Leu Gln Gly Pro Ile Trp Ala Lys Ile Pro His Thr Asp Gly Asn Phe
                530                 535                 540

His Pro Ser Pro Leu Met Gly Gly Phe Gly Leu Lys His Pro Pro Pro
545                 550                 555                 560

Gln Ile Leu Ile Lys Asn Thr Pro Val Pro Ala Asp Pro Pro Leu Thr
                565                 570                 575

Phe Asn Gln Ala Lys Leu Asn Ser Phe Ile Thr Gln Tyr Ser Thr Gly
                580                 585                 590

Gln Val Ser Val Glu Ile Glu Trp Glu Leu Gln Lys Glu Asn Ser Lys
                595                 600                 605

Arg Trp Asn Pro Glu Ile Gln Tyr Thr Ser Asn Tyr Tyr Lys Ser Thr
                610                 615                 620

Asn Val Asp Phe Ala Val Asn Thr Glu Gly Val Tyr Ser Glu Pro Arg
625                 630                 635                 640

Pro Ile Gly Thr Arg Tyr Leu Thr Arg Asn Leu
                645                 650

<210> SEQ ID NO 22
<211> LENGTH: 638
<212> TYPE: PRT
<213> ORGANISM: Artificial Sequence
<220> FEATURE:
<223> OTHER INFORMATION: Synthetic Polypeptide

<400> SEQUENCE: 22

Met Tyr Thr Ile Trp Met Pro Glu Asn Pro Arg Pro Gly Thr Pro Cys
1               5                   10                  15

Asp Ile Phe Thr Asn Ser Arg Gly Lys Arg Ala Ser Asn Gly Gly Gly
                20                  25                  30

Gly Gly Ser Gly Gly Gly Gly Ser Ala Pro Gly Lys Lys Arg Pro Val
            35                  40                  45

Glu Gln Ser Pro Gln Glu Pro Asp Ser Ser Gly Ile Gly Lys Thr
            50                  55                  60

Gly Gln Gln Pro Ala Lys Lys Arg Leu Asn Phe Gly Gln Thr Gly Asp
65                  70                  75                  80

Ser Glu Ser Val Pro Asp Pro Gln Pro Leu Gly Glu Pro Pro Ala Ala
```

```
                 85                  90                  95
Pro Ser Gly Leu Gly Pro Asn Thr Met Ala Ser Gly Gly Ala Pro
            100                 105                 110
Met Ala Asp Asn Asn Glu Gly Ala Asp Gly Val Gly Asn Ser Ser Gly
            115                 120                 125
Asn Trp His Cys Asp Ser Thr Trp Leu Gly Asp Arg Val Ile Thr Thr
            130                 135                 140
Ser Thr Arg Thr Trp Ala Leu Pro Thr Tyr Asn Asn His Leu Tyr Lys
145                 150                 155                 160
Gln Ile Ser Asn Gly Thr Ser Gly Ser Thr Asn Asp Asn Thr Tyr
                165                 170                 175
Phe Gly Tyr Ser Thr Pro Trp Gly Tyr Phe Asp Phe Asn Arg Phe His
                180                 185                 190
Cys His Phe Ser Pro Arg Asp Trp Gln Arg Leu Ile Asn Asn Asn Trp
                195                 200                 205
Gly Phe Arg Pro Lys Arg Leu Asn Phe Lys Leu Phe Asn Ile Gln Val
            210                 215                 220
Lys Glu Val Thr Thr Asn Glu Gly Thr Lys Thr Ile Ala Asn Asn Leu
225                 230                 235                 240
Thr Ser Thr Val Gln Val Phe Thr Asp Ser Glu Tyr Gln Leu Pro Tyr
                245                 250                 255
Val Leu Gly Ser Ala His Gln Gly Cys Leu Pro Pro Phe Pro Ala Asp
                260                 265                 270
Val Phe Met Val Pro Gln Tyr Gly Tyr Leu Thr Leu Asn Asn Gly Ser
            275                 280                 285
Gln Ala Leu Gly Arg Ser Ser Phe Tyr Cys Leu Glu Tyr Phe Pro Ser
            290                 295                 300
Gln Met Leu Arg Thr Gly Asn Asn Phe Gln Phe Ser Tyr Thr Phe Glu
305                 310                 315                 320
Asp Val Pro Phe His Ser Ser Tyr Ala His Ser Gln Ser Leu Asp Arg
                325                 330                 335
Leu Met Asn Pro Leu Ile Asp Gln Tyr Leu Tyr Tyr Leu Val Arg Thr
            340                 345                 350
Gln Thr Thr Gly Thr Gly Gly Thr Gln Thr Leu Ala Phe Ser Gln Ala
            355                 360                 365
Gly Pro Ser Ser Met Ala Asn Gln Ala Arg Asn Trp Val Pro Gly Pro
            370                 375                 380
Cys Tyr Arg Gln Gln Arg Val Ser Thr Thr Thr Asn Gln Asn Asn Asn
385                 390                 395                 400
Ser Asn Phe Ala Trp Thr Gly Ala Ala Lys Phe Lys Leu Asn Gly Arg
                405                 410                 415
Asp Ser Leu Met Asn Pro Gly Val Ala Met Ala Ser His Lys Asp Asp
                420                 425                 430
Asp Asp Arg Phe Phe Pro Ser Ser Gly Val Leu Ile Phe Gly Lys Gln
            435                 440                 445
Gly Ala Gly Asn Asp Gly Val Asp Tyr Ser Gln Val Leu Ile Thr Asp
            450                 455                 460
Glu Glu Glu Ile Lys Ala Thr Asn Pro Val Ala Thr Glu Glu Tyr Gly
465                 470                 475                 480
Ala Val Ala Ile Asn Asn Gln Ala Ala Asn Thr Gln Ala Gln Thr Gly
                485                 490                 495
Leu Val His Asn Gln Gly Val Ile Pro Gly Met Val Trp Gln Asn Arg
                500                 505                 510
```

```
Asp Val Tyr Leu Gln Gly Pro Ile Trp Ala Lys Ile Pro His Thr Asp
            515                 520                 525

Gly Asn Phe His Pro Ser Pro Leu Met Gly Gly Phe Gly Leu Lys His
        530                 535                 540

Pro Pro Pro Gln Ile Leu Ile Lys Asn Thr Pro Val Pro Ala Asp Pro
545                 550                 555                 560

Pro Leu Thr Phe Asn Gln Ala Lys Leu Asn Ser Phe Ile Thr Gln Tyr
                565                 570                 575

Ser Thr Gly Gln Val Ser Val Glu Ile Glu Trp Glu Leu Gln Lys Glu
            580                 585                 590

Asn Ser Lys Arg Trp Asn Pro Glu Ile Gln Tyr Thr Ser Asn Tyr Tyr
        595                 600                 605

Lys Ser Thr Asn Val Asp Phe Ala Val Asn Thr Glu Gly Val Tyr Ser
610                 615                 620

Glu Pro Arg Pro Ile Gly Thr Arg Tyr Leu Thr Arg Asn Leu
625                 630                 635

<210> SEQ ID NO 23
<211> LENGTH: 628
<212> TYPE: PRT
<213> ORGANISM: Artificial Sequence
<220> FEATURE:
<223> OTHER INFORMATION: Synthetic Polypeptide

<400> SEQUENCE: 23

Met Thr Phe Phe Tyr Gly Gly Ser Arg Gly Lys Arg Asn Asn Phe Lys
1               5                   10                  15

Thr Glu Glu Tyr Gly Gly Gly Ser Gly Gly Gly Ser Ala Pro
            20                  25                  30

Gly Lys Lys Arg Pro Val Glu Gln Ser Pro Gln Glu Pro Asp Ser Ser
        35                  40                  45

Ser Gly Ile Gly Lys Thr Gly Gln Gln Pro Ala Lys Lys Arg Leu Asn
    50                  55                  60

Phe Gly Gln Thr Gly Asp Ser Glu Ser Val Pro Asp Pro Gln Pro Leu
65                  70                  75                  80

Gly Glu Pro Pro Ala Ala Pro Ser Gly Leu Gly Pro Asn Thr Met Ala
                85                  90                  95

Ser Gly Gly Gly Ala Pro Met Ala Asp Asn Asn Glu Gly Ala Asp Gly
            100                 105                 110

Val Gly Asn Ser Ser Gly Asn Trp His Cys Asp Ser Thr Trp Leu Gly
        115                 120                 125

Asp Arg Val Ile Thr Thr Ser Thr Arg Thr Trp Ala Leu Pro Thr Tyr
    130                 135                 140

Asn Asn His Leu Tyr Lys Gln Ile Ser Asn Gly Thr Ser Gly Gly Ser
145                 150                 155                 160

Thr Asn Asp Asn Thr Tyr Phe Gly Tyr Ser Thr Pro Trp Gly Tyr Phe
                165                 170                 175

Asp Phe Asn Arg Phe His Cys His Phe Ser Pro Arg Asp Trp Gln Arg
            180                 185                 190

Leu Ile Asn Asn Asn Trp Gly Phe Arg Pro Lys Arg Leu Asn Phe Lys
        195                 200                 205

Leu Phe Asn Ile Gln Val Lys Glu Val Thr Asn Glu Gly Thr Lys
    210                 215                 220

Thr Ile Ala Asn Asn Leu Thr Ser Thr Val Gln Val Phe Thr Asp Ser
225                 230                 235                 240
```

Glu Tyr Gln Leu Pro Tyr Val Leu Gly Ser Ala His Gln Gly Cys Leu
            245                 250                 255

Pro Pro Phe Pro Ala Asp Val Phe Met Val Pro Gln Tyr Gly Tyr Leu
            260                 265                 270

Thr Leu Asn Asn Gly Ser Gln Ala Leu Gly Arg Ser Ser Phe Tyr Cys
            275                 280                 285

Leu Glu Tyr Phe Pro Ser Gln Met Leu Arg Thr Gly Asn Asn Phe Gln
            290                 295                 300

Phe Ser Tyr Thr Phe Glu Asp Val Pro Phe His Ser Ser Tyr Ala His
305                 310                 315                 320

Ser Gln Ser Leu Asp Arg Leu Met Asn Pro Leu Ile Asp Gln Tyr Leu
            325                 330                 335

Tyr Tyr Leu Val Arg Thr Gln Thr Thr Gly Thr Gly Thr Gln Thr
            340                 345                 350

Leu Ala Phe Ser Gln Ala Gly Pro Ser Ser Met Ala Asn Gln Ala Arg
            355                 360                 365

Asn Trp Val Pro Gly Pro Cys Tyr Arg Gln Gln Arg Val Ser Thr Thr
            370                 375                 380

Thr Asn Gln Asn Asn Ser Asn Phe Ala Trp Thr Gly Ala Ala Lys
385                 390                 395                 400

Phe Lys Leu Asn Gly Arg Asp Ser Leu Met Asn Pro Gly Val Ala Met
            405                 410                 415

Ala Ser His Lys Asp Asp Asp Arg Phe Phe Pro Ser Ser Gly Val
            420                 425                 430

Leu Ile Phe Gly Lys Gln Gly Ala Gly Asn Asp Gly Val Asp Tyr Ser
            435                 440                 445

Gln Val Leu Ile Thr Asp Glu Glu Ile Lys Ala Thr Asn Pro Val
            450                 455                 460

Ala Thr Glu Glu Tyr Gly Ala Val Ala Ile Asn Asn Gln Ala Ala Asn
465                 470                 475                 480

Thr Gln Ala Gln Thr Gly Leu Val His Asn Gln Gly Val Ile Pro Gly
            485                 490                 495

Met Val Trp Gln Asn Arg Asp Val Tyr Leu Gln Gly Pro Ile Trp Ala
            500                 505                 510

Lys Ile Pro His Thr Asp Gly Asn Phe His Pro Ser Pro Leu Met Gly
            515                 520                 525

Gly Phe Gly Leu Lys His Pro Pro Gln Ile Leu Ile Lys Asn Thr
            530                 535                 540

Pro Val Pro Ala Asp Pro Leu Thr Phe Asn Gln Ala Lys Leu Asn
545                 550                 555                 560

Ser Phe Ile Thr Gln Tyr Ser Thr Gly Gln Val Ser Val Glu Ile Glu
            565                 570                 575

Trp Glu Leu Gln Lys Glu Asn Ser Lys Arg Trp Asn Pro Glu Ile Gln
            580                 585                 590

Tyr Thr Ser Asn Tyr Tyr Lys Ser Thr Asn Val Asp Phe Ala Val Asn
            595                 600                 605

Thr Glu Gly Val Tyr Ser Glu Pro Arg Pro Ile Gly Thr Arg Tyr Leu
            610                 615                 620

Thr Arg Asn Leu
625

<210> SEQ ID NO 24
<211> LENGTH: 621

```
<212> TYPE: PRT
<213> ORGANISM: Artificial Sequence
<220> FEATURE:
<223> OTHER INFORMATION: Synthetic Polypeptide

<400> SEQUENCE: 24

Met Asn Asn Gln Lys Ile Val Asn Leu Lys Glu Lys Val Ala Gln Leu
1               5                   10                  15

Glu Ala Gly Gly Gly Gly Ser Ala Pro Gly Lys Lys Arg Pro Val Glu
            20                  25                  30

Gln Ser Pro Gln Glu Pro Asp Ser Ser Ala Gly Ile Gly Lys Ser Gly
            35                  40                  45

Ala Gln Pro Ala Lys Lys Arg Leu Asn Phe Gly Gln Thr Gly Asp Thr
    50                  55                  60

Glu Ser Val Pro Asp Pro Gln Pro Ile Gly Glu Pro Pro Ala Ala Pro
65                  70                  75                  80

Ser Gly Val Gly Ser Leu Thr Met Ala Ser Gly Gly Ala Pro Val
                85                  90                  95

Ala Asp Asn Asn Glu Gly Ala Asp Gly Val Gly Ser Ser Ser Gly Asn
                100                 105                 110

Trp His Cys Asp Ser Gln Trp Leu Gly Asp Arg Val Ile Thr Thr Ser
            115                 120                 125

Thr Arg Thr Trp Ala Leu Pro Thr Tyr Asn Asn His Leu Tyr Lys Gln
    130                 135                 140

Ile Ser Asn Ser Thr Ser Gly Gly Ser Ser Asn Asp Asn Ala Tyr Phe
145                 150                 155                 160

Gly Tyr Ser Thr Pro Trp Gly Tyr Phe Asp Phe Asn Arg Phe His Cys
                165                 170                 175

His Phe Ser Pro Arg Asp Trp Gln Arg Leu Ile Asn Asn Asn Trp Gly
            180                 185                 190

Phe Arg Pro Lys Arg Leu Asn Phe Lys Leu Phe Asn Ile Gln Val Lys
    195                 200                 205

Glu Val Thr Asp Asn Asn Gly Val Lys Thr Ile Ala Asn Asn Leu Thr
210                 215                 220

Ser Thr Val Gln Val Phe Thr Asp Ser Asp Tyr Gln Leu Pro Tyr Val
225                 230                 235                 240

Leu Gly Ser Ala His Glu Gly Cys Leu Pro Pro Phe Pro Ala Asp Val
                245                 250                 255

Phe Met Ile Pro Gln Tyr Gly Tyr Leu Thr Leu Asn Asp Gly Ser Gln
            260                 265                 270

Ala Val Gly Arg Ser Ser Phe Tyr Cys Leu Glu Tyr Phe Pro Ser Gln
    275                 280                 285

Met Leu Arg Thr Gly Asn Asn Phe Gln Phe Asn Tyr Glu Phe Glu Asn
290                 295                 300

Val Pro Phe His Ser Ser Tyr Ala His Ser Gln Ser Leu Asp Arg Leu
305                 310                 315                 320

Met Asn Pro Leu Ile Asp Gln Tyr Leu Tyr Tyr Leu Ser Lys Thr Ile
                325                 330                 335

Asn Asp Ser Gly Gln Asn Gln Gln Thr Leu Lys Phe Ser Val Ala Gly
            340                 345                 350

Pro Ser Asn Met Ala Val Gln Gly Arg Asn Tyr Ile Pro Gly Pro Ser
    355                 360                 365

Tyr Arg Gln Gln Arg Val Ser Thr Thr Val Thr Gln Asn Asn Asn Ser
370                 375                 380
```

```
Glu Phe Ala Trp Pro Gly Ala Ser Ser Trp Ala Leu Asn Gly Arg Asn
385                 390                 395                 400

Ser Leu Met Asn Pro Gly Pro Ala Met Ala Ser His Lys Glu Gly Glu
            405                 410                 415

Asp Arg Phe Phe Pro Leu Ser Gly Ser Leu Ile Phe Gly Lys Gln Gly
            420                 425                 430

Thr Gly Arg Asp Asn Val Asp Ala Asp Glu Val Met Ile Thr Asn Glu
            435                 440                 445

Glu Glu Ile Lys Thr Thr Asn Pro Val Ala Thr Glu Ser Tyr Gly Gln
    450                 455                 460

Val Ala Ile Asn His Gln Ser Ala Gln Ala Gln Thr Gly Trp
465                 470                 475                 480

Val Gln Asn Gln Gly Ile Leu Pro Gly Met Val Trp Gln Asp Arg Asp
            485                 490                 495

Val Tyr Leu Gln Gly Pro Ile Trp Ala Lys Ile Pro His Thr Asp Gly
            500                 505                 510

Asn Phe His Pro Ser Pro Leu Met Gly Gly Phe Gly Met Lys His Pro
            515                 520                 525

Pro Pro Gln Ile Leu Ile Lys Asn Thr Pro Val Pro Ala Asp Pro Pro
    530                 535                 540

Thr Ala Phe Asn Lys Asp Lys Leu Asn Ser Phe Ile Thr Gln Tyr Ser
545                 550                 555                 560

Thr Gly Gln Val Ser Val Glu Ile Glu Trp Glu Leu Gln Lys Glu Asn
            565                 570                 575

Ser Lys Arg Trp Asn Pro Glu Ile Gln Tyr Thr Ser Asn Tyr Tyr Lys
            580                 585                 590

Ser Asn Asn Val Glu Phe Ala Val Asn Thr Glu Gly Val Tyr Ser Glu
            595                 600                 605

Pro Arg Pro Ile Gly Thr Arg Tyr Leu Thr Arg Asn Leu
    610                 615                 620

<210> SEQ ID NO 25
<211> LENGTH: 633
<212> TYPE: PRT
<213> ORGANISM: Artificial Sequence
<220> FEATURE:
<223> OTHER INFORMATION: Synthetic Polypeptide

<400> SEQUENCE: 25

Met Tyr Thr Ile Trp Met Pro Glu Asn Pro Arg Pro Gly Thr Pro Cys
1               5                   10                  15

Asp Ile Phe Thr Asn Ser Arg Gly Lys Arg Ala Ser Asn Gly Gly Gly
            20                  25                  30

Gly Gly Ser Ala Pro Gly Lys Lys Arg Pro Val Glu Gln Ser Pro Gln
        35                  40                  45

Glu Pro Asp Ser Ser Ala Gly Ile Gly Lys Ser Gly Ala Gln Pro Ala
50                  55                  60

Lys Lys Arg Leu Asn Phe Gly Gln Thr Gly Asp Thr Glu Ser Val Pro
65                  70                  75                  80

Asp Pro Gln Pro Ile Gly Glu Pro Pro Ala Ala Pro Ser Gly Val Gly
            85                  90                  95

Ser Leu Thr Met Ala Ser Gly Gly Gly Ala Pro Val Ala Asp Asn Asn
            100                 105                 110

Glu Gly Ala Asp Gly Val Gly Ser Ser Gly Asn Trp His Cys Asp
        115                 120                 125
```

```
Ser Gln Trp Leu Gly Asp Arg Val Ile Thr Thr Ser Thr Arg Thr Trp
    130                 135                 140
Ala Leu Pro Thr Tyr Asn Asn His Leu Tyr Lys Gln Ile Ser Asn Ser
145                 150                 155                 160
Thr Ser Gly Gly Ser Ser Asn Asp Asn Ala Tyr Phe Gly Tyr Ser Thr
                165                 170                 175
Pro Trp Gly Tyr Phe Asp Phe Asn Arg Phe His Cys His Phe Ser Pro
                180                 185                 190
Arg Asp Trp Gln Arg Leu Ile Asn Asn Asn Trp Gly Phe Arg Pro Lys
            195                 200                 205
Arg Leu Asn Phe Lys Leu Phe Asn Ile Gln Val Lys Glu Val Thr Asp
        210                 215                 220
Asn Asn Gly Val Lys Thr Ile Ala Asn Asn Leu Thr Ser Thr Val Gln
225                 230                 235                 240
Val Phe Thr Asp Ser Asp Tyr Gln Leu Pro Tyr Val Leu Gly Ser Ala
                245                 250                 255
His Glu Gly Cys Leu Pro Pro Phe Pro Ala Asp Val Phe Met Ile Pro
                260                 265                 270
Gln Tyr Gly Tyr Leu Thr Leu Asn Asp Gly Ser Gln Ala Val Gly Arg
            275                 280                 285
Ser Ser Phe Tyr Cys Leu Glu Tyr Phe Pro Ser Gln Met Leu Arg Thr
        290                 295                 300
Gly Asn Asn Phe Gln Phe Asn Tyr Glu Phe Glu Asn Val Pro Phe His
305                 310                 315                 320
Ser Ser Tyr Ala His Ser Gln Ser Leu Asp Arg Leu Met Asn Pro Leu
                325                 330                 335
Ile Asp Gln Tyr Leu Tyr Tyr Leu Ser Lys Thr Ile Asn Asp Ser Gly
                340                 345                 350
Gln Asn Gln Gln Thr Leu Lys Phe Ser Val Ala Gly Pro Ser Asn Met
            355                 360                 365
Ala Val Gln Gly Arg Asn Tyr Ile Pro Gly Pro Ser Tyr Arg Gln Gln
        370                 375                 380
Arg Val Ser Thr Thr Val Thr Gln Asn Asn Asn Ser Glu Phe Ala Trp
385                 390                 395                 400
Pro Gly Ala Ser Ser Trp Ala Leu Asn Gly Arg Asn Ser Leu Met Asn
                405                 410                 415
Pro Gly Pro Ala Met Ala Ser His Lys Glu Gly Glu Asp Arg Phe Phe
                420                 425                 430
Pro Leu Ser Gly Ser Leu Ile Phe Gly Lys Gln Gly Thr Gly Arg Asp
            435                 440                 445
Asn Val Asp Ala Asp Glu Val Met Ile Thr Asn Glu Glu Glu Ile Lys
        450                 455                 460
Thr Thr Asn Pro Val Ala Thr Glu Ser Tyr Gly Gln Val Ala Ile Asn
465                 470                 475                 480
His Gln Ser Ala Gln Ala Gln Thr Gly Trp Val Gln Asn Gln
                485                 490                 495
Gly Ile Leu Pro Gly Met Val Trp Gln Asp Arg Asp Val Tyr Leu Gln
                500                 505                 510
Gly Pro Ile Trp Ala Lys Ile Pro His Thr Asp Gly Asn Phe His Pro
            515                 520                 525
Ser Pro Leu Met Gly Gly Phe Gly Met Lys His Pro Pro Gln Ile
        530                 535                 540
Leu Ile Lys Asn Thr Pro Val Pro Ala Asp Pro Pro Thr Ala Phe Asn
```

```
                545                 550                 555                 560
Lys Asp Lys Leu Asn Ser Phe Ile Thr Gln Tyr Ser Thr Gly Gln Val
                    565                 570                 575

Ser Val Glu Ile Glu Trp Glu Leu Gln Lys Glu Asn Ser Lys Arg Trp
                580                 585                 590

Asn Pro Glu Ile Gln Tyr Thr Ser Asn Tyr Lys Ser Asn Asn Val
            595                 600                 605

Glu Phe Ala Val Asn Thr Glu Gly Val Tyr Ser Glu Pro Arg Pro Ile
    610                 615                 620

Gly Thr Arg Tyr Leu Thr Arg Asn Leu
625                 630

<210> SEQ ID NO 26
<211> LENGTH: 623
<212> TYPE: PRT
<213> ORGANISM: Artificial Sequence
<220> FEATURE:
<223> OTHER INFORMATION: Synthetic Polypeptide

<400> SEQUENCE: 26

Met Thr Phe Phe Tyr Gly Gly Ser Arg Gly Lys Arg Asn Asn Phe Lys
1               5                   10                  15

Thr Glu Glu Tyr Gly Gly Gly Ser Ala Pro Gly Lys Lys Arg Pro
            20                  25                  30

Val Gln Ser Pro Gln Pro Asp Ser Ser Ala Gly Ile Gly Lys
        35                  40                  45

Ser Gly Ala Gln Pro Ala Lys Lys Arg Leu Asn Phe Gly Gln Thr Gly
    50                  55                  60

Asp Thr Glu Ser Val Pro Asp Pro Gln Pro Ile Gly Glu Pro Pro Ala
65                  70                  75                  80

Ala Pro Ser Gly Val Gly Ser Leu Thr Met Ala Ser Gly Gly Ala
                85                  90                  95

Pro Val Ala Asp Asn Asn Glu Gly Ala Asp Gly Val Gly Ser Ser Ser
            100                 105                 110

Gly Asn Trp His Cys Asp Ser Gln Trp Leu Gly Asp Arg Val Ile Thr
        115                 120                 125

Thr Ser Thr Arg Thr Trp Ala Leu Pro Thr Tyr Asn Asn His Leu Tyr
130                 135                 140

Lys Gln Ile Ser Asn Ser Thr Ser Gly Gly Ser Ser Asn Asp Asn Ala
145                 150                 155                 160

Tyr Phe Gly Tyr Ser Thr Pro Trp Gly Tyr Phe Asp Phe Asn Arg Phe
                165                 170                 175

His Cys His Phe Ser Pro Arg Asp Trp Gln Arg Leu Ile Asn Asn Asn
            180                 185                 190

Trp Gly Phe Arg Pro Lys Arg Leu Asn Phe Lys Leu Phe Asn Ile Gln
        195                 200                 205

Val Lys Glu Val Thr Asp Asn Asn Gly Val Lys Thr Ile Ala Asn Asn
    210                 215                 220

Leu Thr Ser Thr Val Gln Val Phe Thr Asp Ser Asp Tyr Gln Leu Pro
225                 230                 235                 240

Tyr Val Leu Gly Ser Ala His Glu Gly Cys Leu Pro Pro Phe Pro Ala
                245                 250                 255

Asp Val Phe Met Ile Pro Gln Tyr Gly Tyr Leu Thr Leu Asn Asp Gly
            260                 265                 270

Ser Gln Ala Val Gly Arg Ser Ser Phe Tyr Cys Leu Glu Tyr Phe Pro
```

```
                    275                 280                 285
Ser Gln Met Leu Arg Thr Gly Asn Asn Phe Gln Phe Asn Tyr Glu Phe
290                 295                 300
Glu Asn Val Pro Phe His Ser Ser Tyr Ala His Ser Gln Ser Leu Asp
305                 310                 315                 320
Arg Leu Met Asn Pro Leu Ile Asp Gln Tyr Leu Tyr Leu Ser Lys
                325                 330                 335
Thr Ile Asn Asp Ser Gly Gln Asn Gln Gln Thr Leu Lys Phe Ser Val
                340                 345                 350
Ala Gly Pro Ser Asn Met Ala Val Gln Gly Arg Asn Tyr Ile Pro Gly
                355                 360                 365
Pro Ser Tyr Arg Gln Gln Arg Val Ser Thr Thr Val Thr Gln Asn Asn
370                 375                 380
Asn Ser Glu Phe Ala Trp Pro Gly Ala Ser Ser Trp Ala Leu Asn Gly
385                 390                 395                 400
Arg Asn Ser Leu Met Asn Pro Gly Pro Ala Met Ala Ser His Lys Glu
                405                 410                 415
Gly Glu Asp Arg Phe Phe Pro Leu Ser Gly Ser Leu Ile Phe Gly Lys
                420                 425                 430
Gln Gly Thr Gly Arg Asp Asn Val Asp Ala Asp Glu Val Met Ile Thr
                435                 440                 445
Asn Glu Glu Glu Ile Lys Thr Thr Asn Pro Val Ala Thr Glu Ser Tyr
450                 455                 460
Gly Gln Val Ala Ile Asn His Gln Ser Ala Gln Ala Gln Ala Gln Thr
465                 470                 475                 480
Gly Trp Val Gln Asn Gln Gly Ile Leu Pro Gly Met Val Trp Gln Asp
                485                 490                 495
Arg Asp Val Tyr Leu Gln Gly Pro Ile Trp Ala Lys Ile Pro His Thr
                500                 505                 510
Asp Gly Asn Phe His Pro Ser Pro Leu Met Gly Gly Phe Gly Met Lys
                515                 520                 525
His Pro Pro Pro Gln Ile Leu Ile Lys Asn Thr Pro Val Pro Ala Asp
530                 535                 540
Pro Pro Thr Ala Phe Asn Lys Asp Lys Leu Asn Ser Phe Ile Thr Gln
545                 550                 555                 560
Tyr Ser Thr Gly Gln Val Ser Val Glu Ile Glu Trp Glu Leu Gln Lys
                565                 570                 575
Glu Asn Ser Lys Arg Trp Asn Pro Glu Ile Gln Tyr Thr Ser Asn Tyr
                580                 585                 590
Tyr Lys Ser Asn Asn Val Glu Phe Ala Val Asn Thr Glu Gly Val Tyr
                595                 600                 605
Ser Glu Pro Arg Pro Ile Gly Thr Arg Tyr Leu Thr Arg Asn Leu
                610                 615                 620

<210> SEQ ID NO 27
<211> LENGTH: 623
<212> TYPE: PRT
<213> ORGANISM: Artificial Sequence
<220> FEATURE:
<223> OTHER INFORMATION: Synthetic Polypeptide

<400> SEQUENCE: 27

Met Ala Ala Ala Ala Ala Ala Ala Ala Ala Ala Ala Ala Ala Ala Ala
1               5                   10                  15

Ala Ala Ala Ala Gly Gly Gly Gly Ser Ala Pro Gly Lys Lys Arg Pro
```

-continued

```
                20                  25                  30
Val Glu Gln Ser Pro Gln Glu Pro Asp Ser Ser Ala Gly Ile Gly Lys
            35                  40                  45
Ser Gly Ala Gln Pro Ala Lys Lys Arg Leu Asn Phe Gly Gln Thr Gly
        50                  55                  60
Asp Thr Glu Ser Val Pro Asp Pro Gln Pro Ile Gly Glu Pro Pro Ala
65                  70                  75                  80
Ala Pro Ser Gly Val Gly Ser Leu Thr Met Ala Ser Gly Gly Gly Ala
                85                  90                  95
Pro Val Ala Asp Asn Asn Glu Gly Ala Asp Gly Val Gly Ser Ser Ser
            100                 105                 110
Gly Asn Trp His Cys Asp Ser Gln Trp Leu Gly Asp Arg Val Ile Thr
        115                 120                 125
Thr Ser Thr Arg Thr Trp Ala Leu Pro Thr Tyr Asn Asn His Leu Tyr
    130                 135                 140
Lys Gln Ile Ser Asn Ser Thr Ser Gly Gly Ser Ser Asn Asp Asn Ala
145                 150                 155                 160
Tyr Phe Gly Tyr Ser Thr Pro Trp Gly Tyr Phe Asp Phe Asn Arg Phe
                165                 170                 175
His Cys His Phe Ser Pro Arg Asp Trp Gln Arg Leu Ile Asn Asn Asn
            180                 185                 190
Trp Gly Phe Arg Pro Lys Arg Leu Asn Phe Lys Leu Phe Asn Ile Gln
        195                 200                 205
Val Lys Glu Val Thr Asp Asn Asn Gly Val Lys Thr Ile Ala Asn Asn
    210                 215                 220
Leu Thr Ser Thr Val Gln Val Phe Thr Asp Ser Asp Tyr Gln Leu Pro
225                 230                 235                 240
Tyr Val Leu Gly Ser Ala His Glu Gly Cys Leu Pro Pro Phe Pro Ala
                245                 250                 255
Asp Val Phe Met Ile Pro Gln Tyr Gly Tyr Leu Thr Leu Asn Asp Gly
            260                 265                 270
Ser Gln Ala Val Gly Arg Ser Ser Phe Tyr Cys Leu Glu Tyr Phe Pro
        275                 280                 285
Ser Gln Met Leu Arg Thr Gly Asn Asn Phe Gln Phe Asn Tyr Glu Phe
    290                 295                 300
Glu Asn Val Pro Phe His Ser Ser Tyr Ala His Ser Gln Ser Leu Asp
305                 310                 315                 320
Arg Leu Met Asn Pro Leu Ile Asp Gln Tyr Leu Tyr Tyr Leu Ser Lys
                325                 330                 335
Thr Ile Asn Asp Ser Gly Gln Asn Gln Gln Thr Leu Lys Phe Ser Val
            340                 345                 350
Ala Gly Pro Ser Asn Met Ala Val Gln Gly Arg Asn Tyr Ile Pro Gly
        355                 360                 365
Pro Ser Tyr Arg Gln Gln Arg Val Ser Thr Thr Val Thr Gln Asn Asn
    370                 375                 380
Asn Ser Glu Phe Ala Trp Pro Gly Ala Ser Ser Trp Ala Leu Asn Gly
385                 390                 395                 400
Arg Asn Ser Leu Met Asn Pro Gly Pro Ala Met Ala Ser His Lys Glu
                405                 410                 415
Gly Glu Asp Arg Phe Phe Pro Leu Ser Gly Ser Leu Ile Phe Gly Lys
            420                 425                 430
Gln Gly Thr Gly Arg Asp Asn Val Asp Ala Asp Glu Val Met Ile Thr
        435                 440                 445
```

```
Asn Glu Glu Glu Ile Lys Thr Thr Asn Pro Val Ala Thr Glu Ser Tyr
            450                 455                 460

Gly Gln Val Ala Ile Asn His Gln Ser Ala Gln Ala Gln Ala Gln Thr
465                 470                 475                 480

Gly Trp Val Gln Asn Gln Gly Ile Leu Pro Gly Met Val Trp Gln Asp
                485                 490                 495

Arg Asp Val Tyr Leu Gln Gly Pro Ile Trp Ala Lys Ile Pro His Thr
            500                 505                 510

Asp Gly Asn Phe His Pro Ser Pro Leu Met Gly Gly Phe Gly Met Lys
        515                 520                 525

His Pro Pro Pro Gln Ile Leu Ile Lys Asn Thr Pro Val Pro Ala Asp
    530                 535                 540

Pro Pro Thr Ala Phe Asn Lys Asp Lys Leu Asn Ser Phe Ile Thr Gln
545                 550                 555                 560

Tyr Ser Thr Gly Gln Val Ser Val Glu Ile Glu Trp Glu Leu Gln Lys
                565                 570                 575

Glu Asn Ser Lys Arg Trp Asn Pro Glu Ile Gln Tyr Thr Ser Asn Tyr
            580                 585                 590

Tyr Lys Ser Asn Asn Val Glu Phe Ala Val Asn Thr Glu Gly Val Tyr
        595                 600                 605

Ser Glu Pro Arg Pro Ile Gly Thr Arg Tyr Leu Thr Arg Asn Leu
    610                 615                 620

<210> SEQ ID NO 28
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 28

Gly Gly Gly Gly Ser
1               5

<210> SEQ ID NO 29
<211> LENGTH: 57
<212> TYPE: DNA
<213> ORGANISM: Artificial Sequence
<220> FEATURE:
<223> OTHER INFORMATION: Synthetic Nucleic Acid

<400> SEQUENCE: 29
accttcttct acggcggcag caggggcaag aggaacaact tcaagaccga ggagtac      57

<210> SEQ ID NO 30
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 30

Met Ala Ala Ala Ala Ala Ala Ala Ala Ala Ala Ala Ala Ala Ala
1               5                   10                  15

Ala Ala Ala Ala Gly Gly Gly Gly Ser
            20                  25

<210> SEQ ID NO 31
<211> LENGTH: 20
<212> TYPE: PRT
```

```
<213> ORGANISM: Artificial Sequence
<220> FEATURE:
<223> OTHER INFORMATION: Synthetic Polypeptide

<400> SEQUENCE: 31

Met Ala Ala Ala Ala Ala Ala Ala Ala Ala Ala Ala Ala Ala Ala Ala
1               5                   10                  15

Ala Ala Ala Ala
            20

<210> SEQ ID NO 32
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 32

Ala Ala Ala Ala Ala Ala Ala Ala Ala Ala Ala Ala Ala Ala Ala Ala
1               5                   10                  15

Ala Ala Ala Gly Gly Gly Gly Ser
            20

<210> SEQ ID NO 33
<211> LENGTH: 134
<212> TYPE: DNA
<213> ORGANISM: Artificial Sequence
<220> FEATURE:
<223> OTHER INFORMATION: Synthetic Nucleic Acid

<400> SEQUENCE: 33
ctggaggctt gctgaaggct gtatgctgtt tagacttgtg tccttgacct gttttggcca        60
ctgactgact ggcaaagcac aagtctaaac aggacacaag gcctgttact agcactcaca       120
tggaacaaat ggcc                                                         134
```